(12) United States Patent
Söderberg et al.

(10) Patent No.: US 11,034,995 B2
(45) Date of Patent: Jun. 15, 2021

(54) PROXIMITY ASSAY WITH DETECTION BASED ON HYBRIDISATION CHAIN REACTION (HCR)

(71) Applicant: Olink Bioscience AB, Uppsala (SE)

(72) Inventors: Ola Söderberg, Österbybruk (SE); Björn Koos, Uppsala (SE); Cosimo Ducani, Årsta (SE); Björn Högberg, Spånga (SE)

(73) Assignee: NAVINCI DIAGNOSTICS AB, Uppsala (SE)

( * ) Notice: Subject to any disclaimer, the term of this patent is extended or adjusted under 35 U.S.C. 154(b) by 95 days.

(21) Appl. No.: 15/116,267

(22) PCT Filed: Feb. 4, 2015

(86) PCT No.: PCT/EP2015/052340
§ 371 (c)(1),
(2) Date: Aug. 3, 2016

(87) PCT Pub. No.: WO2015/118029
PCT Pub. Date: Aug. 13, 2015

(65) Prior Publication Data
US 2017/0009278 A1   Jan. 12, 2017

(30) Foreign Application Priority Data
Feb. 4, 2014 (GB) .................................... 1401885

(51) Int. Cl.
| | | |
|---|---|---|
| *C12Q 1/6813* | (2018.01) | |
| *C12Q 1/6804* | (2018.01) | |
| *C12Q 1/6876* | (2018.01) | |
| *C12Q 1/6818* | (2018.01) | |
| *C12Q 1/6841* | (2018.01) | |
| *C12Q 1/686* | (2018.01) | |
| *C07K 16/00* | (2006.01) | |
| *G01N 33/53* | (2006.01) | |
| *G01N 33/543* | (2006.01) | |

(52) U.S. Cl.
CPC ............ *C12Q 1/6818* (2013.01); *C07K 16/00* (2013.01); *C12Q 1/6804* (2013.01); *C12Q 1/686* (2013.01); *C12Q 1/6841* (2013.01); *G01N 33/5308* (2013.01); *G01N 33/54306* (2013.01); *G01N 2458/10* (2013.01)

(58) Field of Classification Search
None
See application file for complete search history.

(56) References Cited

U.S. PATENT DOCUMENTS

| | | |
|---|---|---|
| 4,883,867 A | 11/1989 | Lee et al. |
| 5,321,130 A | 6/1994 | Yue et al. |
| 5,340,716 A | 8/1994 | Ullman et al. |
| 5,410,030 A | 4/1995 | Yue et al. |
| 5,436,134 A | 7/1995 | Haugland et al. |
| 5,582,977 A | 12/1996 | Yue et al. |
| 5,658,751 A | 8/1997 | Yue et al. |
| 5,733,523 A | 3/1998 | Kuijpers et al. |
| 5,863,753 A | 1/1999 | Haugland et al. |

(Continued)

FOREIGN PATENT DOCUMENTS

| | | |
|---|---|---|
| EP | 1730161 B1 | 8/2010 |
| EP | 2369015 A1 | 9/2011 |

(Continued)

OTHER PUBLICATIONS

"Custom Antibody Services," (PrecisionAntibodies.com; accessed 2014). (Year: 2014).*
"List of sequenced bacterial genomes" (Wikipedia.com; accessed Jan. 24, 2014) (Year: 2014).*
"Oligonucleotide definition," Merriam-Webster.com; accessed Aug. 23, 2017. (Year: 2017).*
"Oligonucleotide", Wikipedia.com, accessed Feb. 17, 2019. (Year: 2019).*

(Continued)

*Primary Examiner* — Bradley L. Sisson
(74) *Attorney, Agent, or Firm* — Porter Wright Morris & Arthur LLP

(57) ABSTRACT

The present invention provides a method for detecting an analyte in a sample, said method comprising a) contacting said sample with a set of proximity probes comprising at least first and second proximity probes, which probes each comprise an analyte-binding domain capable of binding directly or indirectly to said analyte and a nucleic acid domain, such that the proximity probes can simultaneously bind, directly or indirectly, to the analyte, wherein i) the nucleic acid domains of said first and second proximity probes comprise regions capable of mediating an interaction involving said domains when under permissive conditions; and ii) the nucleic acid domain of one of said first and second probes comprises an HCR initiator region comprised within a metastable secondary structure such that it is unable to initiate an HCR reaction until released from said metastable secondary structure; b) introducing permissive conditions to allow the nucleic acid domains of said first and second probes to interact with each other when said probes have both bound directly or indirectly to the analyte, wherein said interaction results in unfolding of the metastable secondary structure of the nucleic acid domain of the first or second probe to release a single-stranded HCR initiator region; c) performing an HCR reaction using at least two HCR monomers, wherein the first HCR monomer comprises a region of complementarity to the HCR initiator region and hybridisation of the HCR initiator region to the first HCR polymer begins the HCR reaction to form a polymer; and d) detecting the polymer thereby to detect the analyte.

27 Claims, 35 Drawing Sheets

Specification includes a Sequence Listing.

(56) References Cited

U.S. PATENT DOCUMENTS

| | | | |
|---|---|---|---|
| 5,989,823 | A | 11/1999 | Jayasena et al. |
| 6,117,635 | A | 9/2000 | Nazarenko et al. |
| 6,248,526 | B1 | 6/2001 | Weimer |
| 6,326,145 | B1 | 12/2001 | Whitcombe et al. |
| 6,346,384 | B1 | 2/2002 | Pollner |
| 6,444,661 | B1 * | 9/2002 | Barton .................. C07F 15/008 514/185 |
| 6,511,809 | B2 | 1/2003 | Baez et al. |
| 7,632,641 | B2 | 12/2009 | Dirks et al. |
| 7,721,721 | B1 * | 5/2010 | Kronengold ............ F41B 5/105 124/16 |
| 7,727,721 | B2 * | 6/2010 | Pierce .................... C12Q 1/682 435/6.14 |
| 7,960,357 | B2 | 6/2011 | Dirks et al. |
| 8,105,778 | B2 | 1/2012 | Dirks et al. |
| 8,124,751 | B2 | 2/2012 | Pierce et al. |
| 8,198,031 | B2 | 6/2012 | Chan-Yui et al. |
| 8,241,854 | B2 | 8/2012 | Yin et al. |
| 8,507,204 | B2 | 8/2013 | Pierce et al. |
| 8,962,241 | B2 | 2/2015 | Yin et al. |
| 9,217,151 | B2 | 12/2015 | Yin et al. |
| 9,791,437 | B2 | 10/2017 | Egan et al. |
| 9,857,364 | B2 | 1/2018 | Jarhede et al. |
| 9,863,939 | B2 | 1/2018 | Wang et al. |
| 9,995,749 | B2 | 6/2018 | Song et al. |
| 10,048,256 | B2 | 8/2018 | Megede |
| 2006/0228733 | A1 | 10/2006 | Pierce et al. |
| 2006/0234261 | A1 | 10/2006 | Pierce et al. |
| 2009/0011943 | A1 * | 1/2009 | Drmanac ............... C12N 15/64 506/4 |
| 2018/0010166 | A1 | 1/2018 | Pierce et al. |
| 2018/0066303 | A1 | 3/2018 | Husain et al. |
| 2019/0002971 | A1 * | 1/2019 | Koslover ............... G01N 33/48 |

FOREIGN PATENT DOCUMENTS

| | | |
|---|---|---|
| WO | 97/00446 A1 | 1/1997 |
| WO | 01/61037 A1 | 8/2001 |
| WO | 03/044231 A1 | 5/2003 |
| WO | 2005/123963 A2 | 12/2005 |
| WO | 2007/044727 A2 | 4/2007 |
| WO | 2007/044903 A2 | 4/2007 |
| WO | 2011/022820 A1 | 3/2011 |
| WO | 2012/057689 A1 | 5/2012 |
| WO | 2012/152942 A1 | 11/2012 |
| WO | 2013/113699 A2 | 8/2013 |
| WO | 2017/089525 A1 | 11/2017 |
| WO | 2018/009463 A2 | 1/2018 |
| WO | 2018/044939 A1 | 3/2018 |

OTHER PUBLICATIONS

"Viruses", Wikipedia.com, accessed Nov. 24, 2012. (Year: 2012).*
"How many species of bacteria are there", wisegeek.com; accessed Jan. 21, 2014. (Year: 2014).*
"Fungi," Wikipedia.com; accessed Jun. 3, 2013. (Year: 2013).*
"Plant," Wikipedia.com; accessed Aug. 28, 2015. (Year: 2015).*
"Mammal," Wikipedia.com; accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
"Archaea," Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*
Teixeira and Cooper, "Using hominin introgression to trace modern human dispersals", PNAS, vol. 116, No. 31, Jul. 30, 2019, pp. 15327-15332. (Year: 2019).*
Forster et al., "A human gut bacterial genome and culture collection for improved metagenomic analyses", Nature Biotechnology, vol. 37, Feb. 2019, pp. 186-192. (Year: 2019).*
Zhu et al., "A Novel Coronavirus from Patients with Pneumonia in China, 2019", The New England Journal of Medicine, Jan. 24, 2020, 382:727-33. (Year: 2020).*
Kim et al., "The Architecture of SARS-CoV-2 Transcriptome", Cell, 181, 914-921, May 14, 2020. (Year: 2020).*
Chemeris, D. A. et al, 'Real-time hybridization chain reaction' (2008) Doklady Biochemistry and Biophysics 419: 53-55.
Choi, H. M. T. et al., 'Programmable in situ amplification for multiplexed imaging of mRNA expression' (published online Oct. 31, 2010), Nature Biotechnology, 28(11): 1208-1212.
Dirks, R. M. et al., 'Triggered amplification by hybridization chain reaction' (Oct. 26, 2004), Proc Natl Acad Sci USA, 101(43): 15275-15278.
Fredriksson, S. et al., 'Protein detection using proximity-dependent DNA ligation assays' (May 2002), Nature Biotechnology, 20:473-477.
Gullberg, M. et al., 'Cytokine detection by antibody-based proximity ligation' (Jun. 1, 2004), Proc Natl Acad Sci USA, 101(22):8420-8424.
Reid, C. A. et al., 'Real time quantitative PCR' (1996), Genome Res., 6:986-994.
Holland, P. M. et al., 'Detection of specific polymerase chain reaction product by utilizing the 5'—3' exonuclease activity of Thermus Aquaticus DNA polymerase' (Aug. 1991), Proc. Natl Acad. Sci. USA, 88(16): 7276-7280.
Jarvius, M. et al., 'In situ detection of phosphorylated platelet-derived growth factor receptor beta using a generalized proximity ligation method' (Jun. 12, 2007), Molecular & Cellular Proteomics 6(9): 1500-1509.
Lee, L. G. et al., 'Allelic discrimination by nick-translation PCR with fluorogenic probes' (Jun. 22, 1993) Nucleic Acids Research, 21(16): 3761-3766.
Marras, S. A. E. et al., 'Efficiencies of fluorescence resonance energy transfer and contact-mediated quenching in pligonucleotide probes' (Sep. 13, 2002), Nucleic Acids Research, 30(21): e122.
Nazarenko, I. A. et al., 'A closed tube format for amplification and detection of DNA based on energy transfer' (Apr. 28,1997), Nucleic Acids Research, 25(12): 2516-2521.
Niu, S. et al, 'Fluorescence detection for DNA using hybridization chain reaction with enzyme-amplification' (published online Mar. 20, 2010), Chem. Commun., 46: 3089-3091.
Söderberg, O. et al., 'Direct observation of individual endogenous protein complexes in situ by proximity ligation' (Dec. 2006), Nature Methods, 3(12): 995-1000.
Song et al, 'Hybridization chain reaction-based aptameric system for the highly selective and sensitive detection of protein' (Jan. 12, 2012), Analyst,137: 1396-1401.
Tyagi, S. et al., 'Molecular beacons: probes that fluoresce upon hybridization' (Mar. 1996), Nature Biotechnology, 14:303-308.
Whitcombe, D. et al., 'Detection of PCR products using self-probing amplicons and fluorescence' (May 21, 1999), Nature Biotechnology, 17: 804-807.
Schallmeiner, E. et al., 'Sensitive protein detection via triple-binder proximity ligation assays' (published online Dec. 17, 2006), Nature Methods, 4(2): 135-137.
Choi, J. et al., 'Immuno-hybridization chain reaction for enhancing detection of individual cytokine-secreting human peripheral mononuclear cells' (Sep. 1, 2011), Analytical Chemistry, 83(17): 6890-6895.
Tan, Y. et al., 'Proximity-dependent protein detection based on enzyme-assisted fluorescence signal amplification' (Published online Aug. 9, 2013), Biosensors and Bioelectronics, 51: 255-260.
Clausson, C. M., 'Making visible the proximity between proteins' (2014), Digital Comprehensive Summaries of Uppsala Dissertations from the Faculty of Medicine, 673:1-54.
Ang, Y. S et al., 'Engineering self-contained DNA circuit for proximity recognition and localized signal amplification of target biomolecules' (published online Jul. 23, 2014), Nucleic Acids Research, 42(14): 9523-9530.
Venkataraman, S. et al., 'An autonomous polymerization motor powered by DNA hybridization' (published online Jul. 29, 2007), Nature Nanotechnology, 2: 490-494.
Zhang, H. et al., 'Binding-induced DNA assembly and its application to yoctomole detection of proteins' (published online Dec. 20, 2011), Analytical Chemistry, 84: 877-884.
English Translation of Official Action dated Jan. 25, 2019 from corresponding Chinese Application No. 201580018764.6.

(56) References Cited

OTHER PUBLICATIONS

Ang, Yan Shan et al., Engineering a robust DNA split proximity circuit with minimized circuit leakage, Nucleic Acids Research, vol. 44, No. 14, pp. 1-9 (2016).
Förster resonance energy transfer, https://en.wikipedia.org/wiki/F%C3%B6rster_resonance_energy_transfer, Downloaded Nov. 14, 2018.
Decision dated Mar. 2, 2018 from U.S. Pat. No. 10,066,257 (U.S. Appl. No. 13/474,596).

* cited by examiner

Cont. On

Cont. On

PROXIMITY ASSAY WITH DETECTION BASED ON HYBRIDISATION CHAIN REACTION (HCR)

SEQUENCE LISTING

The Sequence Listing submitted herewith, entitled "August-3-2016-2015-02-04-sequence-listing_ST25.txt", created Aug. 3, 2016, and having a size of 3494 bytes, is incorporated herein by reference.

The present invention relates to a proximity-probe based detection assay ("proximity assay"), for an analyte in a sample. The analyte may be any molecule it is desired to detect, including proteins and nucleic acids, in any form or in any type of sample, e.g. whether in situ or in isolated form. The analyte is detected by the binding of at least two probes, which may bind to the analyte directly or indirectly and which, when brought into proximity by binding to the analyte, interact together to allow a signal to be generated. In the new method of the invention the signal is generated by a hybridisation chain reaction (HCR), which is triggered when the probes interact upon analyte binding. Also provided are kits and reagents for performing such an assay.

A proximity assay relies on the principle of "proximity probing", wherein an analyte is detected by the coincident binding of multiple (i.e. two or more, generally two, three or four) probes, which when brought into proximity by binding to the analyte (hence "proximity probes") allow a signal to be generated. Typically, at least one of the proximity probes comprises a nucleic acid domain (or moiety) linked to the analyte-binding domain (or moiety) of the probe, and generation of the signal involves an interaction between the nucleic acid domains/moieties and/or a further functional moiety which is carried by the other probe(s). Thus signal generation is dependent on an interaction between the probes, more particularly and typically between the nucleic acid domains/moieties of the proximity probes, and hence only occurs when both the necessary two (or more) probes have bound to the analyte, thereby improving specificity of the assay. The concept of proximity probing has been developed in recent years and many assays based on this principle are now well known in the art. For example, proximity ligation assays (PLAs) rely on proximal binding of proximity probes to an analyte to generate a signal from a ligation reaction involving or mediated by (e.g. between and/or templated by) the nucleic acid domains of the proximity probes. In a PLA the intra- or intermolecular ligation of at least one, and preferably two or more, nucleic acid molecules forms a detectable, preferably amplifiable, nucleic acid detection product by means of which said analyte may be detected.

Proximity-probe based detection assays, and particularly proximity ligation assays thus permit the sensitive, rapid and convenient detection or quantification of one or more analytes in a sample by converting the presence of such an analyte into a readily detectable or quantifiable nucleic acid-based signal, and can be performed in a homogeneous or heterogeneous format.

Proximity probes of the art are generally used in pairs, and individually consist of an analyte-binding domain with specificity to the target analyte or to a primary binder (e.g antibody) to the analyte, and a nucleic acid domain linked, coupled or conjugated thereto. The analyte-binding domain can be for example a nucleic acid "aptamer" (Fredriksson et al (2002) Nat Biotech 20:473-477) or can be proteinaceous, such as a monoclonal or polyclonal antibody (Gullberg et al (2004) Proc Natl Acad Sci USA 101:8420-8424). The respective analyte-binding domains of each proximity probe pair may have specificity for different binding sites on the analyte, which analyte may consist of a single molecule or a complex of interacting molecules, or may have identical specificities, for example in the event that the target analyte exists as a multimer. When a proximity probe pair come into close proximity with each other, which will primarily occur when both are bound to their respective sites on the analyte molecule or analyte complex, i.e. upon coincident binding of the probes to the target analyte, the functional domains (e.g. nucleic acid domains) are able to interact, directly or indirectly. For example, nucleic acid domains may be joined to form a new nucleic acid sequence generally by means of a ligation reaction, which may be templated by a splint oligonucleotide added to the reaction, said splint oligonucleotide containing regions of complementarity for the ends of the respective nucleic acid domains of the proximity probe pair. The new nucleic acid sequence thereby generated serves to report the presence or amount of analyte in a sample, and can be qualitatively or quantitatively detected, for example by realtime quantitative PCR (q-PCR).

Alternatively, rather than being ligated to each other, the nucleic acid domain(s) of the proximity probes when in proximity may template the ligation of one or more oligonucleotides to each other (which may be the nucleic acid domain of one or more proximity probes or added oligonucleotide(s)), including an intramolecular ligation to circularise an added linear oligonucleotide, for example based on the so-called padlock probe principle, wherein analogously to a padlock probe, the ends of the added linear oligonucleotide are brought into juxtaposition for ligation by hybridising to a template, here a nucleic acid domain of the proximity probe. In such assays strong signal amplication may be achieved by rolling circle amplification (RCA) of the generated circular nucleic acid molecule. Signal generation based on RCA is particularly advantageous when proximity assays are used for localised "in situ" detection of analytes. Various assay formats are described in WO 01/61037 and WO 97/00446.

WO 97/00446 and U.S. Pat. No. 6,511,809 disclose a heterogeneous format for proximity ligation assays, i.e. the analyte is first immobilised to a solid substrate by means of a specific analyte-binding reagent.

Homogeneous proximity ligation assays (i.e., in solution) are disclosed in WO 01/61037, WO 03/044231, WO 2005/123963, Fredriksson et al (2002) Nat Biotech 20:473-477 and Gullberg et al (2004) Proc Natl Acad Sci USA 101: 8420-8424.

Not all proximity assays are based on ligation. WO 2007/044903 discloses proximity probe-based assays for detecting analytes which rely on the formation and detection of a released nucleic acid cleavage product. Some of the described embodiments involve a probe comprised of an analyte-binding moiety and an attached enzyme, which enzyme acts on a nucleic acid moiety attached to the analyte-binding moiety of a second probe, resulting in the release of a detectable nucleic acid cleavage product. Other proximity assays rely on an extension reaction which can occur only when probes have bound in proximity.

Proximity-probe based detection assays, particularly proximity ligation assays, have proved very useful in the specific and sensitive detection of proteins in a number of different applications, e.g. the detection of weakly expressed or low abundance protein or for in situ detection of nucleic acids or proteins. Essentially any analyte for which a binder exists or may be generated may be detected, and there is an interest not only in detecting known proteins or other analytes in a diagnostic setting, but also in proteomic studies to detect not only particular proteins and their levels but also their activity. In many cases, protein activity may be dependent on post-translational modifications (PTMs) and protein-protein interactions (PPIs). Indeed interactions between proteins and nucleic acids (PNAIs) may also be important in the activity of cells and proteins and the analysis of PTMs and all such interactions, PNAIs and PPIs, as well as detection of the proteins themselves, may be important to determine the functional status of a cell or signalling pathway. Hence, selective and sensitive detection of proteins, PTMs and protein interactions, e.g. PPIs, is a major challenge in proteomic studies and in clinical diagnostics. Whilst proximity assays have many benefits rendering them particularly suitable for use in such applications, they have the disadvantage that enzymes are generally used, whether for mediating the interaction between the nucleic acid domains (e.g ligases) and/or in the signal generation or detection step (e.g. a polymerase). This makes the assay more expensive and puts demands on storage and stability of enzymes. For the development of point of care devices for detection of proteins, PTMs and protein interactions a more robust approach, without enzymatic steps would be beneficial.

To address this need, and the need more generally for a robust, simple and easy to use, yet specific and sensitive assay with reduced background (reduced non-specific signal generation) the present invention has been developed. The new assay method of the invention advantageously combines analyte detection by a proximity assay with signal generation by hybridisation chain reaction (HCR) to provide a method which can be used to detect proteins or protein modifications or interactions, or other analytes, selectively, or specifically, and sensitively, with strong signal amplification but without reliance on enzymes.

HCR is a recently developed technique for enzyme-free nucleic acid amplification based on a triggered chain of hybridisation of nucleic acid molecules starting from stable (more particularly metastable) monomer hairpins, or other metastable nucleic acid structures, which hybridise to one another to form a nicked nucleic acid polymer. HCR is described in detail in Dirks and Pierce, 2004, PNAS, 101 (43), 15275-15278 and in U.S. Pat. Nos. 7,632,641 and 7,727,721 which are hereby incorporated by reference in their entirety (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401, all of which are also incorporated by reference in their entirety).

In the simplest form of HCR, two different stable hairpin monomers undergo a chain reaction of hybridisation events to form a long nicked double-stranded DNA molecule when an "initiator" nucleic acid molecule is introduced. In the absence of the initiator the hairpin monomers are stable, or kinetically trapped ("metastable"), and remain as monomers (i.e. preventing the system from rapidly equilibrating). However, once introduced, the initiator is able to hybridise to the first hairpin monomer, and invades it, causing it to open up and hybridise to and invade the second hairpin monomer, in turn opening this up and allowing it to hybridise to and invade another molecule of the first monomer, and so on, until the monomers are exhausted, leading to the formation of a nicked chain of alternating units of the first and second monomer species. The hybridisation and invasion by the initiator thus triggers the HCR. A fundamental principle behind HCR is that short loops of nucleic acid are resistant to invasion by complementary single stranded nucleic acids. This stability allows for the storage of potential energy in the form of nucleic acid loops. Potential energy is released when a triggered conformational change allows the single stranded bases in the loops to hybridise with a complementary strand. HCR monomers thus contain such a loop, as well as a region of complementarity to another HCR monomer which is shielded or protected by the loop structure, such that it can only hybridise to the other HCR monomer when the loop structure is opened up. A first species of monomer also includes an accessible region of complementarity to an initiator molecule. Introduction of the initiator, which hybridises to and invades the first monomer species, opening it up, triggers a chain reaction of alternating kinetic escapes (loop structure openings) by the two monomer species, allowing them to hybridise and thereby corresponding to "polymerisation" into a nicked double helix.

Initially developed to detect a target nucleic acid or small biomolecules through use of aptamers, HCR has more recently been adapted for use in combination with antibodies (Choi et al, 2011, supra), enzymatic-assisted readout (Niu et al, 2010, supra) and real-time analysis (Chemeris et al. 2008, supra).

As noted above, the present invention combines the benefits of proximity probes with HCR. In work leading to the present invention, the inventors were able to develop systems, in which the interaction of the nucleic acid domains of proximity probes may lead to the release (i.e. generation or exposure) of an initiator for the HCR reaction. In this way, the reaction may be controlled such that HCR is not triggered, or initiated, unless and until the proximity probes have bound to the target analyte (directly or indirectly). Further, the interaction of the nucleic acid domains of the proximity probes can be controlled, such that only the nucleic acid domains of probes bound to the analyte in proximity are able to interact with one another. This leads to reduced signal resulting from non-specific probe binding and hence enhanced assay specificity. Thus the specificity and reduced background afforded by the proximity probes may advantageously be combined with the rapid and potent enzyme-free signal generation afforded by HCR.

In the new method of the invention, the nucleic acid domains of the proximity probes are designed to contain a region, or sequence, which is able to interact with a region (sequence) in the nucleic acid domain of another proximity probe, typically by hybridisation to one another. Thus the nucleic acid domains of two proximity probes may contain regions of mutual complementarity to one another, namely a region, or sequence, which is complementary to a region, or sequence in another proximity probe, such that when the probes are in proximity the nucleic acid domains are able to hybridise at said complementary sequences. One of the probes also contains in its nucleic acid domain a region, or sequence, which is able to act as the initiator of an HCR reaction (in other words it is or comprises a sequence which is complementary to an accessible sequence in a first HCR monomer i.e. to the initiator complement region of an HCR monomer). This HCR initiator region is "protected" or shielded from being able to hybridise to the HCR monomer and thereby initiate an HCR reaction by being contained in a metastable secondary structure (more particularly a double stranded metastable secondary structure, e.g a stem-loop structure akin to that of a HCR monomer). Interaction of the nucleic acid domains of the proximity probes, e.g. by hybridisation of the complementary regions thereof, causes the metastable secondary structure to be disrupted, or unfolded (namely "opened up"), thereby releasing the HCR initiator which is then free to hybridise to the first HCR monomer and set off, or trigger, the HCR reaction.

To add a further element of control to the system, the nucleic acid domains of the proximity probes may be designed such that they are not able to interact with one another, that is prevented from interacting (e.g. they are prevented from hybridising to one another) until the interaction is activated, or permitted, which will generally be once the probes have bound to their target molecule(s). Thus, despite the nucleic acid domains having interacting regions, the interacting region or "reactive element" of at least one of the proximity probe nucleic acid domains (that is the elements, or regions, which participate in the interaction between the nucleic acid domains), e.g. region of complementarity, is only made available for interaction once the probes have bound to their respective targets (and if desired any unbound probes have been removed, e.g. washed away). In other words, the interacting region of at least one of the nucleic acid domains may be protected, or shielded from interaction, or the regions may be able to interact only under certain, permissive conditions. The nucleic acid domains may be "activated" to interact, for example by removing the "protection" or introducing permissive conditions. This may be achieved in various ways, for example by use of blocking oligonucleotides which may be removed or displaced, or by protecting the interacting region within a metastable secondary structure which can be unfolded or disrupted to release, or expose, the interacting region, and make it accessible, or available for interaction, e.g. by introducing an activator or "initiator" oligonucleotide (akin to an HCR initiator) which is able to hybridise to the nucleic acid domain and invade the metastable secondary structure causing it to open up, or unfold.

By controlling the interaction of the nucleic acid domains, the assay method or reaction may be allowed to proceed sequentially, i.e. in discrete and/or separable stages. This can significantly improve the sensitivity and specificity of the assay. Moreover, in some embodiments this may simplify the assay protocol as it allows all potentially interacting components to be contacted with the sample simultaneously, without their interaction, i.e. the reactive elements of the nucleic acid domains of the proximity probes are prevented from interacting and hence the HCR reaction is not initiated. Hence, in the first instance the proximity probes are allowed to interact with the sample such that only the analyte-binding domain of the proximity probes may interact with the analyte in the sample. Following sufficient conditions to allow for binding of the proximity probes to the analyte (i.e. upon coincident binding of the probes to the analyte), the interaction of the nucleic acid domains of the proximity probes may be activated or permitted. This may reduce non-specific background signal in the assay.

Accordingly, at its broadest the invention can be seen to provide a method of detecting an analyte in a sample, said method comprising:

(a) contacting said sample with a set of proximity probes comprising at least first and second proximity probes, which probes each comprise an analyte-binding domain capable of binding directly or indirectly to said analyte and a nucleic acid domain, such that the proximity probes can simultaneously bind, directly or indirectly, to the analyte, wherein (i) the nucleic acid domains of said first and second proximity probes comprise regions capable of mediating an interaction involving said domains when under permissive conditions; and (ii) the nucleic acid domain of one of said first and second probes comprises an HCR initiator region comprised within a metastable secondary structure such that it is unable to initiate an HCR reaction until released from said metastable secondary structure;

(b) introducing permissive conditions to allow the nucleic acid domains of said first and second probes to interact with each other when said probes have both bound directly or indirectly to the analyte, wherein said interaction results in unfolding of the metastable secondary structure of the nucleic acid domain of the first or second probe to release a single-stranded HCR initiator region;

(c) performing an HCR reaction using at least two HCR monomers, wherein the first HCR monomer comprises a region of complementarity to the HCR initiator region and hybridisation of the HCR initiator region to the first HCR monomer begins the HCR reaction to form a polymer;

(d) detecting the polymer thereby to detect the analyte.

Advantageously, in step (a) the conditions are not permissive and the nucleic acid domains are not able to interact.

More particularly the interaction is an interaction between the nucleic acid domains, that is the domains interact with one another. Preferably the interaction comprises or involves, or indeed is, hybridisation between the domains. Thus, the nucleic acid domains may contain interacting regions which are mutually interacting e.g. regions capable of hybridising to one another. In other words the nucleic acid domain of a first proximity probe (first nucleic acid domain) may contain a region (i.e. sequence) of complementarity to a cognate region of complementarity in the nucleic acid domain of a second or other proximity probe (second, or other, nucleic acid domain). Such a complementary region in a nucleic acid domain may be viewed as a binding site for another nucleic acid domain.

The term "permissive conditions" is used broadly herein to refer to any state or condition in which the interacting regions of the nucleic acid domains are able to interact. "Non-permissive" conditions means conversely that the interacting regions are not able to interact, and this includes that an interacting region is protected (or shielded or masked), for example by a separately added blocking oligonucleotide or other molecule that hybridises or binds to it, or by a region of secondary structure in the nucleic acid domain. That is the nucleic acid domain may contain a region of self-complementarity. The self-complementary regions may hybridise to one another to form a region of secondary structure. Typically the region of secondary structure will contain a loop of single stranded nucleic acid, more particularly a stem-loop or hairpin structure comprising a double-stranded "stem" region and a single stranded loop. More particularly the secondary structure is a metastable secondary structure.

In preferred embodiments the metastable secondary structure is or comprises a stem-loop, or hairpin. The interacting region may be contained in the secondary structure, for example in the stem region. In this case it is protected from interacting by the stem structure. Alternatively it may lie in the loop region. To prevent interaction, it suffices that only one of the interacting regions is protected, although it is not precluded that more or all (e.g both) interacting regions are protected. Thus where an interacting domain of a first nucleic acid domain is protected, the interacting domain of a second nucleic acid domain may lie in an accessible region of the loop region of a secondary structure. In particular, in the case of two interacting nucleic acid domains, an interacting region may lie in the stem of a first nucleic acid domain, and the cognate interacting region may lie in the loop of a second nucleic acid domain, such that it is accessible to interaction with the first interacting region. In one embodiment the interacting region of a first nucleic acid domain may lie at the end of the nucleic acid domain, more particularly at an end involved in forming the stem of a stem-loop structure, or hairpin. The interacting region of a second nucleic acid domain may lie internally, particularly in the loop of a stem-loop structure, or hairpin. In this way the interacting region of the second domain may be accessible for interaction with the interacting region of the first domain, once the first interacting region is released, or exposed, by disrupting or unfolding the stem-loop or hairpin. It will be apparent however that the interacting region of a second nucleic acid domain may lie partially in the loop of a stem-loop structure, or hairpin, and partially in the stem of a stem-loop structure, or hairpin, i.e. the binding of the interacting region of the first nucleic acid domain to the portion of the interacting region of the second nucleic acid domain leads to strand invasion by the first nucleic acid domain and unfolding of the hairpin structure. Thus, where an interacting region lies in an area of a nucleic domain which is accessible to interaction (e.g. in the loop), it suffices that a part of the interacting region is accessible for interaction (i.e. for binding (hybridisation) to its cognate binding partner)—the whole of the interacting region does not have to be initially accessible, but may become fully accessible as a result of strand invasion and opening up of the metastable secondary structure. Thus the interacting region of a nucleic acid domain (and by analogy other binding domains/sites, or regions of complementarity, of the nucleic acid domain and/or HCR monomer) does not need to be accessible along the full length of the complementary region—it suffices that there is sufficient complementary sequence accessible to allow binding (or hybridisation) to occur.

Permissive conditions may be introduced by removing the blocking oligonucleotide or disrupting or unfolding the secondary structure, e.g disrupting or displacing or invading the double-stranded stem of a stem-loop or hairpin structure. This may include adding a further reagent or assay component, e.g an oligonucleotide (an activator or "initiator" oligonucleotide as discussed above) which is able to bind to the nucleic acid domain to "open up" the secondary structure e.g. to invade or otherwise displace the stem structure, or more broadly to induce a conformational change which exposes, and renders accessible for binding, the interacting region. Alternatively a reagent or component may be added, or conditions may be introduced, which cause or result in removal or displacement of a blocking oligonucleotide e.g. which cause or result in degradation or cleavage of the blocking oligonucleotide. To this end the blocking oligonucleotide may comprise one or more cleavage or degradable groups or nucleotides. For example the blocking oligonucleotide may comprise or be composed of ribonucleotides such that it may be digested by addition of a ribonuclease e.g Rnase.

In alternative embodiments, the blocking oligonucleotide may comprise uracil residues which may cleaved from the oligonucleotide using a uracil-DNA glycosylase (UNG) enzyme. Removal of one or more uracil bases may destabilise the hybridisation with the blocking oligonucleotide causing it to become displaced or released. Further alternatively the blocking oligonucleotide may comprise one or more cleavage recognition sites for a nickase enzyme. Cleavage of the blocking oligonucleotide by the nickase may cause destabilise its hybridisation causing it to be displaced or released.

Where a blocking oligonucleotide is used, it will be pre-hybridised to the nucleic acid domain before the probe is contacted with the sample.

In a further embodiment the nucleic acid domain of a first proximity probe may be designed such that the first interacting region is protected within a secondary structure when the probe is unbound to its target. However, upon target binding a conformational change may be induced which exposes the first interacting region, and makes it available for interaction with the second interacting region of the second proximity probe. For example, binding of the probe may result in a disruption, or unfolding, of the secondary structure to expose, or release, the first interacting region and make it available for interaction. This may be achieved for example with a proximity probe in which the binding domain is an aptamer which undergoes a conformational change on binding or in which binding of the aptamer causes a conformational change in the nucleic acid domain of the probe. In this case it will be seen that the permissive conditions are when the probe has bound to the analyte, directly or indirectly (i.e. when the probe has bound to its target) and non-permissive conditions are when the probe is not bound e.g. when the target or analyte is not present, or when specific binding of the probe to its target has not yet occurred, for example if the conditions are not appropriate or conducive to binding, or insufficient time for binding has been allowed. Such a system may be useful for example where the analyte is or comprised a nucleic acid. In other embodiments, the nucleic acid domain of a first proximity probe may be designed such that a change in physical or chemical conditions may induce or promote a conformational change which exposes or releases the first interacting region, for example a change in pH, temperature, magnetic field, conductivity or redox conditions, or the addition of a chemical reagent The proximity probe, or more particularly the nucleic acid domain, may comprise or be associated with a molecule or moiety which is responsive to the change in physical or chemical conditions, and which undergoes or causes a conformational change to occur in the nucleic acid domain.

For example in one such embodiment the interacting region may be protected by being contained in a secondary structure generated or retained in position by one or more disulphide bridges, or other covalent bridges. In other words, reversible chemical cross-links may be introduced into the nucleic acid domain(s). Thus, chemical groups or moieties may be introduced into the nucleic acid domain(s) which are capable of forming a covalent bond, By appropriately locating such groups (e.g. modifying groups on nucleotides) in the nucleic acid domain, a secondary structure may be generated, or fixed in position (if a secondary structure can form by hybridisation between self-complementary regions) in the proximity probe (e.g. before it is contacted with the analyte). For example, a disulphide bridge could be introduced into the stem of a hairpin structure, e.g. by incorporation of disulphide bond forming groups or moieties at the 5' and 3' ends of the nucleic acid domain. Such a covalent bridge may be disrupted or broken to unfold the secondary structure and to release (i.e. deprotect) the interacting region. This may be achieved for example by introducing an appropriate chemical reagent or appropriate conditions, for example by adding a reducing agent (e.g. DTT) in the case of a disulpide bond. A range of different groups forming reversible covalent bonds are known in the art which can be used to cross-link a nucleic acid domain and generate, or fix or hold in place, a secondary structure. As well as disulphide bonds, such bonds may be created using boronate-based linking technology, or other chemical reactions or methods known or used in the art to create chemical cross-links. Boronate conjugation chemistry works for example by reacting boronic acid groups with alcohol (e.g. diol) groups (Weith et al. 1970. Biochemistry 9, 4396-4401, U.S. Pat. No. 5,777,148).

In a more particularly defined aspect, the invention can be seen to provide a method of detecting an analyte in a sample, said method comprising:

(a) contacting said sample with a set of proximity probes comprising at least first and second proximity probes, which probes each comprise an analyte-binding domain capable of binding directly or indirectly to said analyte and a nucleic acid domain, such that the proximity probes can simultaneously bind, directly or indirectly, to the analyte, wherein (i) the nucleic acid domain of the first probe comprises a first region of complementarity to a cognate second region of complementarity in the nucleic acid domain of the second probe, and said first region of complementarity is protected such that the first and second complementary regions are not able to hybridise to one another;

(ii) the nucleic acid domain of the second probe comprises an HCR initiator region comprised within a metastable secondary structure such that it is unable to initiate an HCR reaction until released from said metastable secondary structure;

(b) deprotecting the first region of complementarity to allow the first and second complementary regions of the nucleic acid domains of said first and second probes to hybridise to each other when said probes have both bound directly or indirectly to the analyte, wherein said hybridisation results in unfolding of the metastable secondary structure of the nucleic acid domain of the second probe to release a single-stranded HCR initiator region;

(c) performing an HCR reaction using at least two HCR monomers, wherein the first HCR monomer comprises a region of complementarity to the HCR initiator region and hybridisation of the HCR initiator region to the first HCR monomer begins the HCR reaction to form a polymer;

(d) detecting the polymer thereby to detect the analyte.

The first region of complementarity may be protected by a blocking oligonucleotide or by a self-complementary region, e.g. by a secondary structure, more particularly a metastable secondary structure, as discussed above and may be deprotected as also discussed above, e.g. by removing (for example degrading or displacing) a blocking oligonucleotide or by unfolding, or disrupting, a secondary structure.

Thus, the nucleic acid domain of at least one proximity probe contains a metastable secondary structure and in one preferred embodiment the nucleic acid domains of both probes contain a metastable secondary structure, preferably a structure containing a loop, particularly a stem-loop structure or hairpin. In the nucleic acid domain of the first probe, the metastable secondary structure protects the first complementary region. In the nucleic acid domain of the second probe, the metastable secondary structure protects the HCR initiator region. In this embodiment, the second complementary region is in an accessible part of the nucleic acid domain of the second probe, and (as explained further below) a region complementary to an activator oligonucleotide may lie in an accessible region of the nucleic acid domain of the first probe.

As described above, and as widely known and reported in the literature, HCR monomers also contain a metastable secondary structure. An HCR monomer is a nucleic acid molecule (generally an oligonucleotide) that is able to assemble to form a polymer by hybridisation in hybridisation chain reaction initiated by an HCR initiator molecule.

"Metastable" means that the nucleic acid molecule in question, whether a nucleic acid domain of a proximity probe or a HCR monomer, is kinetically disfavored from associating with another molecule with which it is designed to associate (specifically, hybridise), be it the nucleic acid domain of another proximity probe (or more particularly the interacting/complementary region thereof), when under non-permissive conditions or in the absence of an initiator or activator for the reaction or interaction, i.e an HCR initiator in the case of HCR monomers or an initiator/activator for the proximity probe interaction (more particularly the interaction between the nucleic acid domains of the proximity probes). The nucleic acid domains or HCR monomers are kinetically trapped. That is, the nucleic acid domains or HCR monomers retain their secondary structure; they are stable under the non-permissive conditions or in the absence of initiator/activator, and the system is unable to equilibrate. When the permissive conditions are introduced, e.g. when the initiator/activator is added or present, it can disrupt (e.g. invade) the secondary structure of the nucleic acid domain (e.g of the first proximity probe) or of one of the HCR monomers (the first HCR monomer). This disruption, or unfolding, releases (or exposes) a reactive element, namely the interacting/complementary region of the nucleic acid domain, or the HCR initiator where the nucleic acid domain of a proximity probe is concerned, or region of complementarity to another HCR monomer species where an HCR monomer is concerned. Thus, the method of the present invention relies on changes in secondary structure induced in a metastable secondary structure by an initiator molecule or region.

The metastable secondary structure preferably comprises at least one loop, more particularly a single stranded nucleic acid loop, and at least one double-stranded region, more particularly a region of self-complementarity wherein two self-complementary regions or portions of the nucleic acid domain (or HCR monomer) hybridise together, e.g. to form a stem or stem-like structure. Thus in a preferred embodiment the metastable secondary structure is (e.g consists of) or comprises a stem-loop or hairpin. In a further preferred embodiment, where the secondary structure (e.g. hairpin) is in the nucleic acid domain of a proximity probe, it does not have a sticky end, that is it does not have a single-stranded end region. (In the case of HCR monomers, as is known in the art, these will generally have a sticky end, to which the HCR initiator binds and/or which is used in the hybridisation chain reaction). The absence of such a sticky end in the nucleic acid domains of the proximity probes helps to ensure that nucleic acid domains do not interact in the absence of probe binding and/or permissive conditions, thereby reducing background signal and improving specificity of the assay.

In many embodiments of the assay, the secondary structure will be, or will comprise, a single stem-loop or hairpin structure, particularly where nucleic acid domains are concerned. However, as is known in the art (especially in the context of HCR) other secondary structures can be designed and envisaged. Thus for example the secondary structure can contain two or more loops, e.g. two loops. For example, a hairpin structure may be modified to include a second loop in one "strand" of the stem one of the self-complementary regions which hybridise to form the stem of the hairpin may contain a stretch of non-complementary nucleotides, that is nucleotides which are not complementary and hence do not hybridise to the other self-complementary region which make up the stem, and which consequently "bulge" out to form a loop (a so-called "bulge-loop"). A hairpin structure may also be modified to include regions of mismatch between the two strands of the stem. In another embodiment, two hairpin structures may be connected by a single-stranded region. Such secondary structures are commonly used in the design of HCR monomers designed to achieve greater than linear HCR amplification, as discussed further below (see e.g. U.S. Pat. No. 7,727,721, particularly FIGS. 3 and 4 thereof).

As noted above, the nucleic acid domains of one or both of the proximity probes preferably comprise, or take the form of, hairpins. In the nucleic acid domain of the first probe, the stem preferably protects the first complementary region. In the nucleic acid domain of the second probe, the stem preferably protects the HCR initiator region. The second complementary region lies in the loop, however this may extend into the stem, i.e. the strand complementary to the HCR initiator region. Accordingly it is accessible for binding by the first complementary region ("accessible" means that the region is available for binding (hybridisation) when the secondary structure is in its kinetically stable ("metastable") state). In such an embodiment, the first complementary region preferably lies at or near the free end of the nucleic acid domain (that is the end that is not attached to the binding domain of the probe), e.g. the 3' end, and this end is hybridised in the stem of the hairpin. However, in an alternative embodiment the first complementary region may lie near, or towards the end of the nucleic acid domain which is attached to the binding domain, or indeed anywhere in the nucleic acid domain. The HCR initiator preferably region lies at the free end of the second nucleic acid domain, e.g. the 3' end, which end is hybridised in the stem of the hairpin. When the first complementary region is deprotected, or released, it is able to hybridise to the second complementary region in the loop (and stem) of the second nucleic acid domain. This causes the hairpin of the second nucleic acid domain to unfold and to open up the stem structure, releasing, or exposing, the HCR initiator region, which is then free to initiate an HCR reaction in the presence of HCR monomers. More particularly, binding of the first complementary region to the second complementary region results in invasion of the stem structure of the hairpin of the second nucleic acid domain by the released hairpin of the first nucleic acid domain, causing the hairpin of the second nucleic acid domain to open to expose, or release, the HCR initiator region. In a preferred embodiment, where first complementary region hybridises to the second complementary region, the resulting nucleic acid duplex structure may comprise one or more mismatches (such as two, three, four or more mismatches). In a further preferred embodiment, the cognate complement sequence of the second complementary region (i.e. the sequence forming a strand of the hairpin in the nucleic acid domain of the second proximity probe) may comprise one or more mismatches (such as two, three, four or more mismatches) relative to the sequence of the activator oligonucleotide. In other words, in a preferred embodiment, the activator oligonucleotide may not bind to this region with 100% complementarity. Furthermore, in yet another preferred embodiment, the first complementary region may comprise one or more mismatches (such as two, three, four or more mismatches) relative to the complement of a sequence present in the HCR monomers. In other words, in this embodiment the first complementary region may not bind to the HCR monomers with 100% complementarity. The mismatches reduce the stability of the complex formed, which may make the system less efficient. However, the mismatches prevent the activator oligonucleotide from binding to the second complementary region, and prevent the HCR monomers from binding to the complex between the activator oligonucleotide and the nucleic acid domain of the first proximity probe (i.e. the first complementary region). In other words, whilst not an essential feature of proximity-HCR detection, this may help to reduce non-specific signal.

In a further preferred embodiment, the sequence of the HCR initiator region is not present in the nucleic acid domain of the first proximity probe, and the sequence complementary to the activator oligonucleotide is not present in the nucleic acid domain of the second proximity probe.

To deprotect the first complementary region (i.e. to introduce permissive conditions) an activator or initiator oligonucleotide is preferably used. This is an initiator for the proximity probe interaction (i.e. a proximity or interaction initiator) and is distinct from the HCR initiator. For convenience, the term "activator oligonucleotide" is hereinafter used. Thus a separate activator oligonucleotide may be introduced, or contacted with the bound proximity probes (e.g. added to the sample, or reaction mix). In such an embodiment the first nucleic acid domain of the first proximity probe further comprises a binding site for the activator oligonucleotide, that is a region complementary to a cognate complementary region in the activator oligonucleotide, namely an "activator complement region". The activator complement region is located at an accessible site in the first nucleic acid domain, such that it is available for hybridisation with the activator (i.e. when the secondary structure of the first nucleic acid domain is in its kinetically stable "metastable" state). Conveniently, the activator complement region may be contained in the loop of the hairpin of the first nucleic acid domain, though may also also extend into the stem of the first nucleic acid domain, i.e. the strand complementary to the first complementary region. (As noted and explained above, it suffices that at least part of the activator complement region is accessible (i.e. lies in an accessible part of the nucleic acid domain)).

The activator oligonucleotide thus comprises a cognate region of complementarity to the activator complement region of the first nucleic acid domain.

In carrying out the method, an activator oligonucleotide may be added to the sample, or to a reaction mixture containing the proximity probes bound to the analyte. This may for example after a step of contacting the probes with the sample, and incubating the probes with the sample to allow the probes to bind. Advantageously, after the probes have been allowed to bind, there may be a washing step, or other step to remove or separate any unbound probes. Following this the activator oligonucleotide may be added (or, analogously another step of introducing permissive conditions, e.g. deprotecting the first complementary region may be performed).

Upon binding of the activator oligonucleotide to the activator complement region, the activator oligonucleotide may invade, or otherwise displace, the stem region of the hairpin of the first nucleic acid domain, causing it to open up i.e. to release the hairpin. This exposes, or releases, i.e. deprotects, the first complementary region, rendering it available to hybridise to the second complementary region.

The design of metastable secondary structures such as hairpins etc is known in the art and can be carried out based on known principles. For the present invention the secondary structure of the nucleic acid domain(s) is designed to be stable enough so that it is not unfolded, or opened up, until activated, or permitted to do so, for example so that the hairpin(s) do not open up by themselves. This can be achieved by taking into account known parameters such as size/length of loop or stem etc, and C/G ratios of the stems (double-stranded regions) etc. The strength of the stem needs to be balanced with the size of the loop etc taking account of the assay design e.g. balancing reaction time against stability to reduce non-specific signals etc. Such design considerations are within the routine skill of the skilled artisan in this field. Accordingly the length of the loop and stem or double-stranded regions can be varied or adjusted to ensure kinetic stability in particular conditions and/or to control or adjust the rate of reaction.

To improve specificity of the method, various options are available to ensure that an unwanted binding (hybridisation) site for the activator oligonucleotide is not present in the nucleic acid domain of the "other" proximity probe, and further that unwanted sequences corresponding to (i.e. equivalent or identical to) to an HCR initiator are not present, for example that a sequence equivalent (i.e. identical) to the HCR initiator is not present in a nucleic acid domain of a first proximity probe and that an activator complement region (i.e. hybridisation site for the activator) is not present in a nucleic acid domain of a second nucleic acid domain).

Accordingly, inn a preferred embodiment of the present invention, the invading strand (the activator oligonucleotide, the first complementary region or the HCR initiator region) is not identical to a sequence of a nucleic acid domain which is within a double stranded region in a metastable secondary structure (e.g. which forms a stem). Thus, the invading strand is not able to bind (hybridise) to a complementary sequence in the double-stranded (e.g. stem) structure in the nucleic acid domain. This may be achieved in different ways, for example by shifting the sequence of the cognate complementary region (complementary to the invading strand) so that it is accessible in the nucleic acid domain of one probe (e.g. located in the loop) and hidden in a double-stranded structure of the other, by designing the sequences such that the invading strand does not hybridise to the end of a stem region, and by introducing mismatches, as discussed above, so that the sequences in question are different and unwanted (non-specific) hybridisation is avoided or minimised, or a combination of any of these approaches. Thus, the invading strand may a) bind to a sequence within a single-stranded loop of a stem-loop structure in addition to a portion of a stem region; and/or b) not bind to the full length of a stem region; and/or c) comprise one or more mismatches relative to the nucleic acid sequence of the stem region. Any combination of these features may be included when designing nucleic acids of the invention, such as (a), (b) or (c) alone, (a) and (b), (a) and (c), (b) and (c), or (a), (b) and (c).

A further possibility to improve specificity is to reduce the length of the activator oligonucleotide—this may allow unwanted hybridisation of the activator oligonucleotide to the nucleic acid domain of the second proximity probe to be reduced or minimised, but without having a significant negative impact on signal generation. For example, an activator oligonucleotide may typically be 44 nt long—reducing this by 6 nt may still permit sufficient initiation of HCR but may reduce hybridisation of the activator oligonucleotide to the nucleic acid domain of the second probe. This may be combined with any one of more of the options above (e.g. (a), (b) and/or (c)).

As described in the Examples below, for example, in a system using two proximity probes with hairpins and an activator oligonucleotide of 44 nt, the first hairpin is designed with a stem of 30 bp and a loop of 18 nt and the second hairpin has a stem of 24 bp and a loop of 19 nt. Thus by way of representative example the stem to loop ratio of a stem-loop structure in a nucleic acid domain may be in region of 1.0 to 2.0, preferably 1.2 to 1.8, or more particularly 1.24 to 1.70, or about 1.25 to about 1.67, e.g. 1.3 to 1.6. For example the first hairpin may have a ratio of about 1.3 and the second hairpin may have a ratio of about 1.6. However, different ratios may be used, depending upon the exact system, structure design and/or reaction conditions employed.

A representative loop size for a nucleic acid domain may for example be 9 to 30 nt, more particularly from any one of 10, 11, 12, 15, 16, 17, or 18 to any one of 30, 28, 25, 24, 23, 22, 21, 20 or 19 e.g 15 to 20, 16 to 20, 17 to 20, 16 to 19 or 17-19. As noted above, this may however be varied depending on the system.

A representative stem length for a nucleic acid domain may be for example 10 to 50 nt, more particularly from any one of 12, 15, 18, 19, 20, 21, 22, 23 or 24 to any one of 45, 40, 35, 34, 33, 32, 31, 30, 29, 28, 27, 26, 25, or 24, e.g. 15 to 32, 15-30, 18-32, 18-30 etc.

As noted above, the analyte-binding domain of the proximity probe may be any binding partner for the target analyte, and it may be a direct or indirect binding partner therefor. Thus it may bind to the target analyte directly, or indirectly via an intermediary molecule or binding partner which binds to the target analyte, the analyte-binding domain binding to said intermediary molecule (binding partner). In such a situation the intermediary binding partner which binds directly to the analyte may be viewed as a primary binding partner or the analyte and the proximity probe will be a secondary binding partner. Particularly, the analyte-binding domain or the intermediary binding partner is a specific binding partner for the analyte. A binding partner is any molecule or entity capable of binding to its target, e.g. target analyte, and a specific binding partner is one which is capable of binding specifically to its target (e.g. the target analyte), namely that the binding partner binds to the target (e.g. analyte) with greater affinity and/or specificity than to other components in the sample. Thus binding to the target analyte may be distinguished from non-target analytes; the specific binding partner either does not bind to non-target analytes or does so negligibly or non-detectably or any such non-specific binding, if it occurs, may be distinguished. The binding between the target analyte and its binding partner is typically non-covalent.

In some embodiments where the proximity probe binds to the analyte via an intermediary molecule, the proximity probe may be pre-incubated with the intermediary molecule. In other embodiments the sample may be contacted first with the intermediary molecule, and incubated to allow the molecule to bind. Following an optional washing step, the proximity probes may then be contacted with the sample.

The analyte binding domain may be selected to have a high binding affinity for is target, e.g a target analyte or an intermediary molecule. By high binding affinity is meant a binding affinity of at least about $10^{-4}$ M, usually at least about $10^{-6}$ M or higher, e.g., $10^{-9}$ M or higher. The analyte binding domain may be any of a variety of different types of molecules, so long as it exhibits the requisite binding affinity for the target molecule when present as part of the proximity probe. In other embodiments, the analyte binding domain may be a ligand that has medium or even low affinity for its target, e.g. less than about $10^{-4}$ M.

Hence, the analyte binding domain of the proximity probe may be any molecule capable of selectively binding to a target molecule. For example, the binding domain may be selected from a protein, such as a monoclonal or polyclonal antibody, lectin, soluble cell surface receptor, combinatorially derived protein from phage display or ribosome display, peptide, carbohydrate, nucleic acid, such as an aptamer or a nucleic acid molecule comprising the complementary sequence for a target nucleic acid, or combinations thereof. In a preferred embodiment of the invention, the analyte binding domain is a protein, preferably an antibody or derivative or fragment thereof.

In another preferred embodiment of the analyte-binding domain of the proximity probe is a nucleic acid molecule. The analyte-binding domains of the proximity probes may be made up of ribonucleotides and/or deoxyribonucleotides as well as synthetic nucleotide residues that are capable of participating in Watson-Crick type or analogous base pair interactions. Thus, the nucleic acid domains may be DNA and/or RNA or any modification thereof e.g. PNA or other derivatives containing non-nucleotide backbones.

The term "detecting" is used broadly herein to include any means of determining the presence of the analyte (i.e. if it is present or not) or any form of measurement of the analyte. Thus "detecting" may include determining, measuring, assessing or assaying the presence or absence or amount or location of analyte in any way. Quantitative and qualitative determinations, measurements or assessments are included, including semi-quantitative. Such determinations, measurements or assessments may be relative, for example when two or more different analytes in a sample are being detected, or absolute. As such, the term "quantifying" when used in the context of quantifying a target analyte(s) in a sample can refer to absolute or to relative quantification. Absolute quantification may be accomplished by inclusion of known concentration(s) of one or more control analytes and/or referencing the detected level of the target analyte with known control analytes (e.g., through generation of a standard curve). Alternatively, relative quantification can be accomplished by comparison of detected levels or amounts between two or more different target analytes to provide a relative quantification of each of the two or more different analytes, i.e., relative to each other.

The "analyte" may be any substance (e.g. molecule) or entity it is desired to detect by the method of the invention. The analyte is the "target" of the assay method of the invention. The analyte may accordingly be any biomolecule or chemical compound it may be desired to detect, for example a peptide or protein, or nucleic acid molecule or a small molecule, including organic and inorganic molecules. The analyte may thus be or may comprise a nucleic acid molecule, which may be any nucleic acid, e.g RNA or DNA or any modification thereof. Included are molecules consisting solely of nucleic acid, or chimeric molecules or complexes comprising nucleic acid and another component. The nucleic acid may be in native form e.g. in situ in a sample, or it may be isolated, or a synthetic nucleic acid molecule e.g a cloned molecule or amplicon etc. The analyte may be a cell or a microorganism, including a virus, or a fragment or product thereof. It will be seen therefore that the analyte can be any substance or entity for which a specific binding partner (e.g. an affinity binding partner) can be developed. All that is required is that the analyte is capable of simultaneously binding at least two binding partners (more particularly, the analyte-binding domains of at least two proximity probes). Proximity probe-based assays, such as that of the present invention, have found particular utility in the detection of proteins or polypeptides. Analytes of particular interest may thus include proteinaceous molecules such as peptides, polypeptides, proteins or prions or any molecule which includes a protein or polypeptide component, etc., or fragments thereof. The analyte may be a single molecule or a complex that contains two or more molecular subunits, e.g. including but not limited to protein-protein and protein-nucleic acid (e.g. protein-DNA) complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA. Of particular interest may be the interactions between proteins and nucleic acids, e.g. regulatory factors, such as transcription factors, and DNA or RNA. In other representative embodiments, the analyte may be a nucleic acid molecule or region thereof. Hence, the analyte may be DNA (e.g. genomic, mitochondrial) or RNA (e.g. messenger RNA, ribosomal RNA, microRNA etc). Advantageously, the nucleic acid may be detected in situ, i.e. without removing or extracting the nucleic acid from the cell.

All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared or they may be prior-treated in any convenient way e.g. for storage.

Representative samples thus include any material which may contain a biomolecule, or any other desired or target analyte, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, blood cells, urine, faeces, cerebrospinal fluid or any other body fluids (e.g. respiratory secretions, saliva, milk, etc), tissues, biopsies, cell cultures, cell suspensions, conditioned media or other samples of cell culture constituents, etc. The sample may be pre-treated in any convenient or desired way to prepare for use in the method of the invention, for example by cell lysis or purification, isolation of the analyte, etc.

The binding sites on the analyte for the respective analyte-binding domains of the proximity probes in a set may be the same or different. Thus, for example in the case of a homomeric protein complex or aggregate comprising two or more identical subunits or protein constituents, the analyte-binding domains of two or more probes may be the same. Where the analyte is a single molecule or comprises different sub-units or constituents (e.g. a heteromeric complex or an aggregate of different proteins or an interaction between different molecules), the analyte-binding domains will be different.

Since the length of the nucleic acid domain of the proximity probes can be constructed to span varying molecular distances, binding sites on the analyte for the analyte-binding domain need not be on the same molecule. They may be on separate, but closely positioned, molecules. For example, the multiple binding domains of an organism, such as a bacterium or cell, or a virus, or of a protein complex or interaction can be targeted by the methods of the present invention.

The proximity probes for use in the detection method of the invention comprise an analyte-binding domain and a nucleic acid domain. Proximity probes are in effect detection probes which bind to the analyte (via the analyte-binding domain), the binding of which may be detected (to detect the analyte) by means of detecting the interaction which occurs between the nucleic acid domains thereof upon such binding. The nucleic acid domain is coupled to the analyte-binding domain and this "coupling" or connection may be by any means known in the art, and which may be desired or convenient and may be direct or indirect, e.g. via a linking group. Where the analyte-binding domain is also a nucleic acid, it is preferred that the domains are coupled by a nucleotide bond, i.e. a phosphodiester bond. Examples of the way in which a protein may be coupled to a nucleic acid are described in detail below. Preferably, where the proximity probes do not comprise only nucleic acids the linker or the means used to couple the analyte-binding domain and the nucleic acid domain of the proximity probe is same for each proximity probe.

In a preferred aspect of the methods of the invention, the analyte-binding domain of at least one proximity probe (further preferably of at least two, or more preferably of all the proximity probes) is a proteinaceous molecule. Thus, the analyte-binding domain may be a small peptide molecule or a larger polypeptide or protein. A peptide may, for example range in size from about 5 to about 100 amino acid residues, usually from about 5 to about 50 residues and more usually from about 10 to about 30 residues. By large polypeptide or protein is meant a molecule ranging in size from about 100 amino acid residues or greater. As noted above, of particular interest as analyte-binding domains are antibodies, as well as binding fragments and derivatives or mimetics thereof. Where antibodies are the analyte-binding domain, they may be derived from polyclonal compositions, such that a heterogeneous population of antibodies differing by specificity are each "tagged" with the same tag nucleic acid (nucleic acid domain) or monoclonal compositions, in which a homogeneous population of identical antibodies that have the same specificity for the target analyte are each tagged with the same nucleic acid. As such, the analyte-binding domain may be either a monoclonal or polyclonal antibody. In yet other embodiments, the affinity-binding domain is an antibody fragment or derivative or mimetic thereof, where these fragments, derivatives and mimetics have the requisite binding affinity for the target analyte. Examples of antibodies, antibody fragments, mimetics and derivatives thereof are described above and the present invention contemplates the affinity-binding domain may be any type of these molecules, provided they have the requisite binding affinity for the target analyte.

The term "antibody" as used herein can mean an antibody binding fragment or derivative or mimetic thereof, where these fragments, derivatives and mimetics possess the binding affinity for the target analyte. For example, antibody fragments, such as Fv, F(ab)$_2$ and Fab may be prepared by cleavage of the intact protein, e.g. by protease or chemical cleavage. Also of interest are recombinantly or synthetically produced antibody fragments or derivatives, such as single chain antibodies or scFvs, or other antibody derivatives such as chimeric antibodies or CDR-grafted antibodies, where such recombinantly or synthetically produced antibody fragments retain the binding characteristics of the above antibodies, i.e. that they are capable of binding specifically to the target analyte. Such antibody fragments or derivatives generally include at least the $V_H$ and $V_L$ domains of the subject antibodies, so as to retain the binding characteristics of the subject antibodies. Such antibody fragments, derivatives or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments, derivatives and mimetics thereof may be obtained from commercial sources and/or prepared using any convenient technology, where methods of producing polyclonal antibodies, monoclonal antibodies, fragments, derivatives and mimetics thereof, including recombinant derivatives thereof, are known to those of the skill in the art.

In other preferred embodiments, as described above, the analyte-binding domain of one or more (preferably two or more or all) of the proximity probes may be a nucleic acid molecule.

Importantly, the analyte-binding domain will be one that includes a moiety that can be covalently attached to the nucleic acid domain without substantially abolishing the binding affinity of the analyte-binding domain to its target analyte.

In one embodiment of the method of the present invention the proximity probes may be multivalent proximity probes. Such multivalent proximity probes comprise at least two, analyte binding domains conjugated to at least one, and preferably more than one, nucleic acid(s). Thus, multivalent proximity probes may comprise at least 5, 10, 20, 50, 100, 200, 500 or 1000 analyte-binding domains conjugated to at least one, and preferably more than one, nucleic acid(s).

The "coupling" or connection as described above may be by any means known in the art, and which may be desired or convenient and may be direct or indirect e.g. via a linking group. For example, the domains may be associated with one another by covalent linkage (e.g. chemical cross-linking) or by non-covalent association e.g., via streptavidin-biotin based coupling (biotin being provided on one domain and streptavidin on the other).

The two components of the proximity probes may be joined together either directly through a bond or indirectly through a linking group. Where linking groups are employed, such groups may be chosen to provide for covalent attachment of the binding domain and nucleic acid domain through the linking group. Linking groups of interest may vary widely depending on the nature of the component domains. The linking group, when present, is in many embodiments biologically inert. A variety of linking groups are known to those of skill in the art and find use in the subject proximity probes. In representative embodiments, the linking group is generally at least about 50 daltons, usually at least about 100 daltons and may be as large as 1000 daltons or larger, for example up to 1000000 daltons if the linking group contains a spacer, but generally will not exceed about 500 daltons and usually will not exceed about 300 daltons. Generally, such linkers will comprise a spacer group terminated at either end with a reactive functionality capable of covalently bonding to the nucleic acid domain or protein component. Spacer groups of interest may include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject markers include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like. The proximity probes employed in the subject methods may be prepared using any convenient method. In representative embodiments, the analyte-binding domains and the nucleic acid domains may be coupled, either directly or through a linking group. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used in covalently bonding the components together to produce the proximity probe include: hydroxy, sulfhydryl, amino, and the like. The particular portion of the different components that are modified to provide for covalent linkage may be chosen so as not to substantially adversely interfere with that component's binding affinity for its target. In other words, the covalent linkage should not inhibit the analyte-binding domain of the proximity probe from binding the target analyte and should not encourage the nucleic acid domain to bind to the target analyte. Where necessary and/or desired, certain moieties on the components may be protected using blocking groups, as is known in the art, see e.g. Green & Wuts, Protective Groups in Organic Synthesis (John Wiley & Sons) (1991). Methods for producing nucleic acid/antibody conjugates are well known to those of skill in the art. See e.g. U.S. Pat. No. 5,733,523, the disclosure of which is herein incorporated by reference.

In other embodiments, the proximity probes may be produced using in vitro protocols that yield nucleic acid-protein conjugates, i.e. molecules having nucleic acids, e.g. coding sequences, covalently bonded to a protein, i.e. where the analyte-binding domain or protein component is produced in vitro from vectors which encode the proximity probe. Examples of such in vitro protocols of interest include: RepA based protocols (see e.g., Fitzgerald, Drug Discov. Today (2000) 5:253-258 and WO 98/37186), ribosome display based protocols (see e.g., Hanes et al., Proc. Natl Acad. Sci. USA (1997) 94:4937-42; Roberts, Curr Opin Chem Biol (1999) June; 3: 268-73; Schaffitzel et al., J Immunol Methods (1999) December 10; 231: 119-35; and WO 98/54312), etc.

As noted above, the analyte-binding domain may bind to the analyte directly or indirectly. In the case of indirect binding, the target analyte may first be bound by a specific binding partner (or affinity ligand), and the analyte-binding domain of the proximity probe may bind to the specific binding partner. In such as situation, the proximity probe may be viewed as a secondary binding partner. This enables the design of proximity probes as universal reagents. For example the analyte-specific binding partner may be an antibody, and a universal proximity probe set may be used to detect different analytes by binding to the Fc regions of the various different analyte-specific antibodies.

In a particular embodiment, a nucleic acid-based spacer (i.e an oligonucleotide spacer, or spacer sequence) may be used to provide additional length and/or flexibility to a nucleic acid domain. This is particularly useful in the context of proteinaceous analyte-binding domains such as antibodies, and especially when the proximity probe is used as a secondary binding reagent (e.g. secondary antibody). Such a spacer may consist of a number of nucleotides according to choice or requirement, and will of course be selected or designed not to interfere or compete with other binding sites (hybridisation regions/complementary regions) present in the nucleic acid domains. Typically, it will be a homopolymeric sequence, e.g. a stretch of adenine (A) residues. The length may depend on the precise system and sequences used (nucleic acid domains, analyte binding domains etc.) and may readily be determined by routine experiments. For example a oligonucleotide sequence (e.g. oligoA) of 3 to 12 nucleotides may be used, e.g. 3 to 10, 4 to 10, 4 to 8, or 4 to 6, for example 5. Thus, for example, the sequences for the proximity probe nucleic acid domain sequences (proximity probe hairpins) shown in Tables 2-5 in the Examples below are shown with an additional 5 A residues at their 5' ends. The HCR step of the method of the invention may be performed as known and described in the art, for example as described in U.S. Pat. No. 7,727,721 or any of the other US patents cited herein. HCR monomers may be contacted with the sample e.g. added to the sample. Depending on assay design they may be added to the sample with the proximity probes, e.g. together with the probes or at substantially the same time. Alternatively, they may be added after the probe binding step, for example after the probes have been allowed to bind, optionally after unbound probes have been washed away. They may be added before, after or simultaneously with an activator oligonucleotide, if used, or analogously before, after or during introduction of other permissive conditions. In one representative embodiment they may be added after the activator oligonucleotide has been added and allowed to incubate, and optionally after a subsequent washing step.

A HCR reaction requires at least two HCR monomers, namely at least two species of HCR monomer. The HCR monomers comprise a metastable secondary structure, as defined and described above. They also generally comprise a sticky end. The secondary structure (e.g. the stem-loop or hairpin structure) protects a binding site for (or region of complementarity to) a cognate binding site (or region of complementarity) in a different (other) HCR monomer (species). The first HCR monomer (species) comprises a region of complementarity to the HCR initiator region, that is an "HCR initiator complement region". This region lies in an accessible region (site, location or portion) of the HCR monomer, such that it may be bound by the HCR initiator when the first HCR monomer is in a kinetically stable state (i.e. a monomer which is in the monomer, not unfolded, state). As noted above, the HCR initiator complement region generally lies in a sticky end of an HCR monomer. Such a sticky end may thus be regarded as an "input" region of the HCR monomer. Hybridisation of the HCR initiator causes it to invade the secondary structure and to open or unfold it and to release, or make available for binding, a so-called "output" region, namely a region comprising the binding site for another, e.g. second HCR monomer species. This output region in turn hybridises to its cognate binding site, which (as for the first HCR monomer) lies in the sticky end of the second (or further) HCR monomer. The sticky end of the second or other HCR monomer may thus be regarded as analagous to the initiator complement region of the first HCR monomer i.e. as an input region. Thus the output region of one (e.g. first) HCR monomer (which is protected or sequestered in the monomer in its kinetically stable state) hybridises, when the monomer is opened up, to the input region of another (e.g second) HCR monomer (which is accessible in the monomer in its kinetically stable state). This first (unfolded) HCR monomer then invades the secondary structure of the second HCR monomer causing it to open up (unfold) releasing its output region. This in turn hybridises to the input region of another member of the first HCR monomer species and invades it, opening it up, and so the HCR reaction continues, until all the monomers are used up. This hybridisation of alternating HCR monomer units results in the build-up of a polymer made up of the monomer units (i.e. a polymerisation). The resulting polymer may be detected.

The output region, or binding site for another HCR monomer ("HCR monomer binding site"), may lie in the loop and/or stem region of a hairpin. Generally it lies in the loop or comprises at least a loop portion. In a representative embodiment the binding site lies partly in the loop region and partly in the stem region of a monomer hairpin. Similarly the HCR monomers may be designed such that the input region comprises not just the sticky end, but also lies partly in the stem region. Thus a part of the input region may be complementary to a part of the output region. The stem regions of different HCR monomers may be identical.

Modifications of the basic HCR reaction are possible. More than two (species of) HCR monomers may be used, e.g. 3, 4, 5 or 6 or more. Such modifications may be used to achieve more than linear amplification e.g assembly into a branched structure leading to quadratic growth or assembly into a dendritic structure leading to exponential amplification, as described for example in U.S. Pat. No. 7,727,721. Typically each HCR monomer comprises at least one region that is complementary to at least one other HCR monomer. For non-linear amplification schemes typically at least 3 or more preferably at least 4 HCR monomers are used. In such systems the HCR monomer may comprise two or more loops, for example the hairpin may comprise a bulge-loop and/or two linked hairpins as described above. Alternatively, to achieve more than linear amplification a HCR monomer may be provided with a "tag" sequence which is released when the monomer is unfolded and is able to act as an initiator for a further round of HCR.

In a classical HCR the sequences of two HCR monomers are completely complementary to each other such the resulting polymer has a nicked structure. In such an embodiment the nicks in one or both strands of the double-stranded polymer may be ligated, e.g. using a ligase enzyme. This may be advantageous, for example to create a nucleic acid polymer which is covalently attached to the HCR initiator of the second proximity probe, and therefore firmly attached, or tethered, to the analyte. This may be useful for localised or in situ detection for example. It may be advantageous also to have a more rigid, or stable, HCR product. This may readily be achieved by providing one or more of the HCR monomers with a 5' phosphate group for ligation. However, the HCR reaction is not limited to producing a nicked product, and by appropriate design of HCR monomers a HCR product may be produced which contains single-stranded regions. For example, the HCR monomers may be designed so that they hybridise to one another leaving a gap, rather than a nick, between hybridised ends. In such a case, HCR monomer may include a sequence, for example as part of a loop, or in the loop region, which is not complementary to another (e.g. the second) HCR monomer. Single-stranded regions might also be introduced using modified HCR monomers, for example an HCR monomer which comprises two hairpins linked by a single-stranded region. Such a single-stranded region may be, for example, 5-30 e.g. 10-25, 10-30, 15-30, 15-25 nt long. This may allow the binding of a further type of probe, e.g detection probe thereto (see further below).

The HCR product may be further manipulated after the HCR reaction, for example by ligation as discussed above, or by incorporating a polymerase extension reaction, e.g. using the HCR product as template, for example to extend across a single-stranded gap region in the HCR product. The HCR reaction may accordingly be combined with other signal generation or signal amplification procedures. One possibility may be to combine the signal generation by HCR with a rolling circle amplification (RCA) step. RCA is a known procedure for amplifying a circular nucleic acid template molecule using a strand-displacing polymerase (e.g. a polymerase such as phi29) to produce a long linear concatemeric product comprising multiple complementary copies of the template circle. Such a RCA product may readily be detected and RCA has in recent years formed the basis of a number of nucleic-acid based detection techniques, including techniques using proximity probes where either nucleic acid molecules from the nucleic acid domains are circularised or the nucleic acid domain(s) of the probe template the circularisation of added oligonucleotide(s) to form a circular template for RCA. More generally a circularisable oligonucleotide (e.g a probe) may be used to generate a circulate template for RCA, for example detection probes which are circularised (by ligation) as part of the detection reaction, e.g. padlock probes or molecular inversion probes. Accordingly in one embodiment, a circularisable probe may be used in combination with the method, after the HCR step. In other words, the method of the invention may comprise a further step of carrying out an RCA step using the HCR polymer product. For example, a circularisable probe may be hybridised to the HCR product, more particularly an HCR product comprising single stranded regions. The probe may be designed to have complementary ends which hybridise to the single stranded regions in juxtaposition for ligation, directly or indirectly, to each other. Ligation of the ends results in the generation of a circular molecule which may be used as the template for a RCA reaction. If the ends hybridise adjacently to one another they may be ligated directly. Alternatively if they hybridise with an intervening gap, the gap may be filled with a gap oligonucleotide or by gap-filling polymerase extension of the hybridised 3' end prior to ligation, in which case the ends are indirectly ligated to one another. The RCA product may be detected (e.g. using hybridisable detection probes which hybridise it, or by incorporating labelled nucleotides into the RCA product, by tag/barcode sequences incorporated into the RCA product etc). As noted above, single stranded regions may be incorporated into the HCR product by appropriate design of HCR monomers.

As discussed above in relation to the nucleic acid domains, the HCR monomers may be designed using principles known in the art, for example selecting appropriate loop sizes, stem lengths, stem C/G ratios, sticky end lengths etc., having regard to achieving the desired metastable secondary structure (i.e having a stable secondary structure at equilibrium), hybridisation kinetics, sequence symmetry minimisation etc.

Other than to achieve the desired hybridisations for formation of the secondary structure and for binding to the HCR initiator or another HCR monomer the sequence of HCR monomers is not critical. However, the sequences should be chosen to avoid the occurrence of hybridization events other than those desired.

The length of the loops, stems and/or sticky ends can be adjusted to ensure kinetic stability in particular reaction conditions and to adjust the rate of polymerisation in the presence of HCR initiator. In some embodiments the loops may be the same length as the sticky ends. In some embodiments the loops are shorter than the stems, for example the stems may be twice or three times as long as the loops. However, in other embodiments, including as exemplified in the Examples below, much lower stem to loop ratios may be used, for example in the ranges discussed in the context of the nucleic domains above.

By way of representative example, the loops may be 3 to 100 nt, e.g. 3 to 50, 3 to 40, 3 to 30, 3 to 20, 3-18, 3-15, or 3 to 12; or more particularly from any one of 4, 5, 6, 7 or 8 to any one of 20, 18, 15, 13, 14, 13, 12, 11, 10 or 9. However, in a preferred embodiment, the loop is at least 6 nt in length, such as 7, 8, 9, 10 or 11 nt in length.

By way of representative example the stems may be from for example 8 to 50 nt, more particularly from any one of 9, 10, 11, 12, 15, 18, 19 or 20 to any one of 45, 40, 35, 30, 25, 20 or 18, e.g. 8-20, 8-18, 9-20, 9-18, 10-20, 10-18, 12-18 etc. However, in a preferred embodiment the stems are less than 18 bp in length, such as 17, 16 or 15 bp in length.

Thus by way of representative example, the stem to loop ratio of the HCR monomers may preferably be from 1.0 to 2.0, preferably 1.2-1.8, or more particularly 1.4-1.7. This allows the amplification rate to proceed at a reasonable rate, whilst providing a stable amplification product.

The nucleic acid domain of the proximity probes or the HCR monomers may be made up of ribonucleotides and/or deoxyribonucleotides as well as synthetic nucleotide residues that are capable of participating in Watson-Crick type or analogous base pair interactions. Thus, the nucleic acid domain and.or the HCR monomers may be DNA or RNA or any modification thereof e.g. PNA or other derivatives containing non-nucleotide backbones. The HCR monomers may also include chemical modifications of the nucleotides or other, non-nucleotide chemical groups. For example, analogously to the modification discussed above in the context of the nucleic acid domains of the proximity probes, the HCR monomers may include disulphide bonds, or other covalent bridges, or more particularly groups which allow such bonds or bridges to form. Thus, HCR monomers may include disulphide bond-forming groups or moeities, or other groups or moieties forming other cleavable covalent bonds, which may be used to form bonds or bridges which stabilise the secondary structure of the monomers and which may cleaved or disrupted (i.e. broken) to destabilise the secondary structure and allow the monomer to unfold.

Once the sequences of the nucleic acid domains and HCR monomers is selected or identified, they may be synthesized using any convenient method.

The term "hybridisation" or "hybridises" as used herein refers to the formation of a duplex between nucleotide sequences which are sufficiently complementary to form duplexes via Watson-Crick base pairing. Two nucleotide sequences are "complementary" to one another when those molecules share base pair organization homology. Hence, a region of complementarity in a nucleic acid domain of a proximity probe refers to a portion of that nucleic acid domain that is capable of forming an intra- or intermolecular duplex, i.e. either a duplex within the same molecule (a hairpin structure) or a duplex with a different molecule. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule. The regions of complementarity (i.e. hybridisation regions) may have a length in the range of 4-30 bp e.g. 6-20, 6-18, 7-15 or 8-12 bp.

To carry out the method of the invention, the sample may be contacted with a blocking reagent prior to contact with at least one set of probes to reduce non-specific proximity probe interactions.

In certain embodiments a sample may be assayed for two or more different target analytes. In such embodiments, the sample is contacted with a set of proximity probes for each target analyte, such that the number of sets contacted with the sample may be two or more, e.g., three or more, four or more etc. (i.e. multiple sets of proximity probes may be used). Such methods find particular use in multiplex and high-throughput applications. In this respect, the methods of the invention are particularly advantageous for the detection of multiple analytes in a sample, both in homogeneous and heterogeneous formats. In some embodiments, e.g. for the detection of highly mutable analytes such as viral sequences, multiple probe sets may be used for the same analyte (e.g. transcript) to optimise the efficiency of the detection. In other representative embodiments, the analyte-binding domain may be designed to encompass tolerance for some mismatches, e.g. the where the analyte-binding domain and analyte are both nucleic acids the sequences do not need to be 100% complementary, e.g. the sequences may share at least 85, 90 or 95% sequence identity. Each different probe set may be used with its own set of HCR monomers, which may be designed to result in the formation of distinguishable polymers (e.g. the monomers may be differently labelled, for example with distinguishable labels, or may be designed to have different detectable sequences, e.g. a tag sequence which may bind to a distinguishable detection probe etc).

The amount of proximity probes that is added to a sample may be selected to provide a sufficiently low concentration of proximity probe in the reaction mixture to ensure that the proximity probes will not randomly come into close proximity with one another in the absence of binding to a target analyte, at least not to any great or substantial degree. As such, it is intended that only when the proximity probes bind the analyte through the binding interaction between the analyte-binding domains of the proximity probes and the binding sites of the analyte, do the proximity probes come into close proximity to one another (i.e. upon coincident binding of the proximity probes to the analyte). In representative embodiments, the concentration of the proximity probes in the reaction mixture following combination with the sample ranges from about 1 fM to 1 µM, such as from about 1 µM to about 1 nM, including from about 1 µM to about 100 nM.

Following combination of the sample and set(s) of proximity probes, the reaction mixture may be incubated for a period of time sufficient for the proximity probes to bind target analyte, if present, in the sample. Once the proximity probes have bound to the analyte, permissive conditions may be introduced, as discussed above, for example by adding, or contacting with an activator oligonucleotide. This step may include an incubation step. This allows the nucleic acid domains to interact, to release the HCR initiator. As discussed above, HCR monomers may then be added to initiate the HCR reaction, or they may be added at an earlier stage, for example with the permissive conditions (e.g. with the activator oligonucleotide. In some embodiments, there may be an initial first step of contacting the sample with a primary binding partner (intermediary molecule) and then contacting with the proximity probes. Alternatively the primary binding partners and proximity probes may be contacted with the sample together. In some representative embodiments, e.g. in situ assays or other assays in which the analyte is immobilised, wash steps may be included between the various contacting steps/additions, e.g. after one or more of contacting with primary binding partners, proximity probes, activator oligonucleotide (or other permissive conditions) etc. In this way unbound or non-specifically bound probes, or activator oligonucleotide etec may be removed or separated.

In representative embodiments, the proximity probes and sample may be incubated for a period of time ranging from 5 minutes to about 24 hours, e.g from about 20 minutes to 12 hours, at a temperature ranging from 4 to about 50° C., e.g. at room temperature, for example 18-30° C., or at 37° C. Conditions under which the reaction mixture is maintained should be optimized to promote specific binding of the proximity probe to the analyte, while suppressing non-specific binding.

Following the introduction of permissive conditions, the reaction mixture may be incubated for a period of time ranging from about 5 minutes to about 48 hours, including from about 20 or 30 minutes to about 12 hours, at a temperature ranging from about 4 to about 50° C., including from about 20 to about 37° C. Conditions should allow for efficient and specific interaction (e.g. hybridization) between the nucleic acid domains as described above.

In certain embodiments, the effective volume of the incubation mixture is reduced, at least during the portion of the incubation step in which the proximity probes are binding to target analyte, if present in the sample. In these embodiments, the effective volume of the incubation mixture may be reduced for a number of different reasons. In certain embodiments, the effective volume of the incubation mixture is reduced in order to allow for the use of medium and low affinity analyte-binding domains and/or increase the sensitivity of the assay. For example, in certain embodiments where the effective volume of the incubation mixture is reduced, the analyte-binding domains may be medium or low affinity binders, by which is meant that the analyte-binding domains may have a binding affinity for their target analyte that is less than about $10^{-4}$ M, such as about 1 mM $K_d$. In certain embodiments, the sensitivity of the assay may be increased such that the assay can detect as few as about 100 or fewer target analytes in a 1 µl sample, including as few as about 75 or fewer target analytes in a 1 µl sample, including as few as about 50 or fewer target analytes in a 1 µl sample.

In certain embodiments, a "crowding agent" or "volume excluder" is included in the mixture during the incubation step reviewed above, e.g., to reduce the effective volume of the incubation mixture during binding of the proximity probes to their target analyte. Typically, the "crowding agent" is a water soluble macromolecular material. Suitable macromolecular materials broadly comprise biocompatible natural or synthetic polymers having an average molecular weight of from about 1500 to several million, which do not specifically interact with the other reagents in the mixture, or the product. Such polymers are known in the art as "volume-excluders", as their primary function is to occupy volume in the in vitro reaction medium and provide a highly concentrated environment for biochemical reactions, e.g., approximating in vivo conditions. The volume-excluding polymers must of course be sufficiently soluble to provide the required concentration. Suitable exemplary polymers include, but are not limited to: commercially available polyethylene glycol (PEG) polymers, e.g., having an average molecular weight greater than about 2000, FICOLL polymers such as those having an average molecular weight of about 70,000, bovine plasma albumin, glycogen, polyvinylpyrrolidone, dextran, etc. PEG polymers of higher molecular weights, especially, PEG 1450, PEG 3350, PEG 6000 (also sold as PEG 8000), and PEG 20,000, having average molecular weights of about 1450, 3000-3700, 6000-7500, and 15,000-20,000, respectively, are employed in representative embodiments. PEG 6000 and PEG 8000 are employed in representative embodiments. The concentration of the volume-excluding polymers in the incubation reaction in representative embodiments falls within a range of about 5% w/v to about 45% w/v, depending upon the type of polymer and its molecular weight. In general, it is expected that a given type of polymer of higher molecular weight need be present in lower concentration than the same type of polymer of lower molecular weight to achieve the same effect on enzyme activity.

In those embodiments where a volume excluder is employed, prior to the next step of the method, the incubation mixture may be diluted to account for the presence of the volume excluder, e.g., by at least about 2-fold or more, such as at least about 5-fold or more, including at least about 10-fold or more, depending on the amount of volume excluder that is present, the nature of the dilution fluid, etc., where in representative embodiments the dilution fluid is water or some other suitable aqueous fluid of water and one or more solutes, e.g., salts, buffering agents, etc.

Instead of, or in addition to, the use of a volume excluder, the incubation mixture may be reduced in volume during incubation by removing a portion of the water from the incubation mixture, e.g., via evaporation. In these embodiments, the volume of the fluid may be reduced by at least about 2-fold or more, such as at least about 5-fold or more, including at least about 10-fold or more, as desired. Importantly, not all of the water is removed from the incubation mixture in these embodiments. Any convenient protocol may be employed for reducing the volume of the incubation mixture by removing a select portion of the water therefrom.

An instrument for controlling evaporation rate by monitoring and adjusting humidity and temperature may be employed, where in certain embodiments the volume of the incubation mixture is monitored, e.g., by continuously measuring the volume of the incubation mixture, where when appropriately evaporated, further reagents, e.g, HCR monomers, may be added, as described above. As desired, a heating block could be used to enhance the evaporation. Alternatively, the volume of the incubation mixture may be reduced by filtrating out water. In representative embodiments, a size exclusion filter is used to selectively contain molecules of sizes larger than a cut off limit while smaller molecules and water is removed by passage through the filter. The force placed on the solution to move it through the filter may be by either centrifugation or vacuum suction.

Upon binding of the analyte-binding domains of the proximity probes to the analyte, the nucleic acid domains of the proximity probes come into close proximity to one another. However, the nucleic acid domains will not be capable of interacting until permissive conditions have been introduced.

Interaction of the domains releases the HCR initiator and the HCR reaction may then be allowed to take place. This may be performed according to procedures and conditions well known in the art and described in the literature.

Generation of the HCR reaction product, namely the polymer, may then be detected in order to detect the presence of the target analyte in the sample being assayed.

The HCR product may, in the broadest sense, be detected using any convenient protocol. The particular detection protocol may vary depending on the sensitivity desired and the application in which the method is being practiced. The resulting polymer HCR product may be detected in a number of different ways. Any method known for the detection of nucleic acids may be used, for example based on size separation, e.g various forms of electrophoresis, nucleic acid staining techniques, light scattering spectroscopy, such as dynamic light scattering (DLS), viscosity measurement, mass changes determined by e.g surface plasmon resonance and spectrophotometric techniques based on detection of colorimetric or fluorescent labels etc. In this regard the HCR polymer may be directly labelled by incorporating a label into it, or it may be indirectly labelled e.g by hybridising or otherwise binding a labelled detection probe to it. For example a detection probe may be designed to hybridise to a particular sequence (e.g. a tag sequence) present in one or more HCR monomers. For example, both HCR monomers may be labelled. In an alternative embodiment, one monomer may be labelled, and the second monomer may be provided with a 5' phosphate group such that it may be ligated.

Conveniently, one or more of the HCR monomers may be directly labelled, e.g., fluorescently, or otherwise spectrophotometrically, or radioisotopically labelled or with any signal-giving label, such that the polymer product is directly labelled. Alternatively, the HCR monomers may be labelled, akin to conformationally selective probes such as molecular beacons, such that the signal (e.g fluorescence) is quenched when the HCR monomers are in monomer form, but detectable when the monomers have been unfolded, i.e when hybridised in the polymer. Thus for example the HCR monomer may be labelled at one end of a stem with a quencher molecule and with a fluorophore at the opposing side of the duplex region, such that when the stem structure is present in the monomer the fluorescent signal is quenched. Upon polymerisation the fluorophore and quencher are spatially separated in the polymer, and quenching is relieved, allowing a fluorescent signal to be detected. Thus an HCR monomer may be labelled in a conformationally sensitive way. In an alternative embodiment the acceptor and donor molecules for an energy transfer reaction may be provided on different monomers, which upon unfolding and hybridisation to one another allow a FRET-pair to form, and thus generate signal. In a still further format, the acceptor and donor molecules may be provided as described in e,g, LOCI (U.S. Pat. Nos. 5,340,716, 6,346,384) or as described in U.S. Pat. No. 8,198,031 and detecting the cleaved moiety. HCR may thus accordingly monitored, or the presence of an HCR product determined by an energy transfer reaction such as FRET.

Various dyes or stains may be used to selectively detect double stranded DNA products, e.g., via intercalation. Representative detectable molecules include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. Alternatively, the nucleic acid stain is or incorporates an acridine dye, or a homo- or heterodimer thereof, such as acridine orange, acridine homodimer, ethidium-acridine heterodimer, or 9-amino-6-chloro-2-methoxyacridin, or an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). The nucleic acid stain may also be a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR Green, EvaGreen, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In terms of embodiments in which the signal producing system is specific for the polymer product, as opposed to double stranded molecules in general the signal producing system may, as noted above, include a detection probe (e.g.

detection oligonucleotide) that specifically binds to a sequence found in the polymer product, where the probe nucleic acid may be labelled with a directly or indirectly detectable label, or an HCR monomer itself may be provided with such a label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probe nucleic acids include, but are not limited to: fluorescein, the cyanine dyes, such as Cy3, Cy5, Alexa 555, Bodipy 630/650, and the like. Other labels, such as those described above, may also be employed as are known in the art.

In certain embodiments, as also noted above the HCR monomers may be labelled with "energy transfer" labels. As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. As used herein, "energy transfer pair" refers to any two molecules that participate in energy transfer. Typically, one of the molecules acts as a fluorescent group, and the other acts as a fluorescence-modifying group. "Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. Non-fluorescent groups may also be used as acceptors or donors, e.g non-fluorescent quenching groups include nucleotides e.g. guanine bases (see for example Marras et al., 2002, Nucleic Acids Research, 30(21), e122. In cases where there are multiple fluorescent groups and/or multiple quenching groups, the individual groups may be different from one another. As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly. As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others' electronic structure. If the fluorescence-modifying group is a quenching group, this will result in the quenching group preventing the fluorescent group from even emitting light.

As an alternative to labelling the HCR monomer, an energy transfer labelled detection probe e.g., oligonucleotide, may be used. Specific examples of such labelled oligonucleotide probes include the Taq Man® type probes, as described in U.S. Pat. No. 6,248,526, the disclosure of which is herein incorporated by reference (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). Other types of probe structures include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference).

The next step in the subject methods is signal detection from the labelled polymer products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the target nucleic acid via detection of the pseudotarget nucleic acid and/or amplification products thereof. Depending on the particular label employed, detection of a signal may indicate the presence or absence of the target nucleic acid.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter, or where the sample is a tissue sample on a microscope slide, fluorescence may be detected using a fluorescence microscope. Fluorescence is suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time. Thus, in some embodiments multiple analytes may be detected in parallel, whereas in other embodiments multiple analytes may be detected sequentially, e.g. one analyte at a time or one group of analytes at a time.

Where the detection protocol is a real time protocol, data may be collected in this way at frequent intervals, for example once every 3 minutes, throughout the reaction. By monitoring the fluorescence of the reactive molecule from the sample the progress of the polymerisation reaction can be monitored in various ways.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other.

The data generated as described above can be interpreted in various ways. For example, simply the presence or absence of analyte may be determined by detecting the polymer. However, since the size of the HCR product is inversely related to the amount of target analyte in a sample, quantitative measurements may be possible. Accordingly, the concentration of analyte may be determined. This may conveniently be done by determining the average molecular weight of the HCR polymer product, which may be done using standard techniques. Standard curves and control samples may be used.

In this manner, a reaction mixture may readily be screened (or assessed or assayed etc.) for the presence of target analyte(s). The methods are suitable for detection of a single target analyte as well as multiplex analyses, in which two or more different target analytes are assayed in the sample. In these latter multiplex situations, the number of different sets of probes that may be employed typically ranges from about 2 to about 20 or higher, e.g., as up to 100 or higher, 1000 or higher, etc. wherein the multiple analytes in a sample may be detected in parallel or sequentially.

In the case of detecting an analyte with proximity-probes of low affinity and slow binding kinetics, the proximity-probes may be contacted with the sample and incubated at a sufficiently high concentration to promote binding of the proximity probes to the analyte. This incubation step may be quickly diluted in a large volume of cold buffer (e.g., buffer that does not include the analyte or the proximity probes), and a portion of this dilution subsequently used in the further steps of the method.

Problems associated with complex samples may be further addressed by diluting the complex sample prior to the analysis.

The method of the present invention may be employed homogeneously (i.e. in solution) as described above, or alternatively heterogeneously, using a solid phase, for example, in which analyte becomes immobilised on a solid phase, permitting the use of washing steps. The use of solid phase assays offers advantages, particularly for the detection of difficult samples: washing steps can assist in the removal of inhibiting components, and analytes can be enriched from an undesirably large sample volume. Higher concentrations and greater amounts of proximity probes can be used, as unbound analytes and probes can be removed by washing. The ability to remove unbound probes, or probes which have not interacted, by washing also means that the solid phase assay tolerates lower purity proximity probes by comparison with the homogeneous assay Immobilisation of the analyte on a solid phase may be achieved in various ways. Accordingly, several embodiments of solid phase proximity probe assays are contemplated. In one such embodiment, one (or more) of the first or second proximity probes may be (or may be capable of being) immobilised on a solid phase (or solid support). The analyte can firstly be captured by the one (or more) immobilised (or immobilisable) probes and secondly be bound by subsequently added probe(s). Alternatively, an analyte may first be captured by an immobilised capture probe, and then contacted with the proximity probes. Further alternatively, the analyte may be immobilised by other means, e.g. the sample may be fixed on a solid support such as a slide. This is particularly applicable to in situ detection procedures.

The immobilised proximity probe or capture probe may be immobilised, i.e. bound to the support, in any convenient way. Thus the manner or means of immobilisation and the solid support may be selected, according to choice, from any number of immobilisation means and solid supports as are widely known in the art and described in the literature. Thus, the probe may be directly bound to the support, for example via the analyte-binding domain (e.g. chemically cross-linked), it may be bound indirectly by means of a linker group, or by an intermediary binding group(s) (e.g. by means of a biotin-streptavidin interaction). Thus, a proximity probe or capture probe may be provided with means for immobilisation (e.g. an affinity binding partner, e.g. biotin or a hapten or a nucleic acid molecule, capable of binding to its binding partner, i.e. a cognate binding partner, e.g. streptavidin or an antibody or a nucleic acid molecule) provided on the support. The probe may be immobilised before or after binding to the analyte. Further, such an "immobilisable" probe may be contacted with the sample together with the support.

The solid support may be any of the well known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc.

The support may be made of glass, silica, latex or a polymeric material. Suitable are materials presenting a high surface area for binding of the analyte. Such supports may have an irregular surface and may be for example porous or particulate e.g. particles, fibres, webs, sinters or sieves. Particulate materials e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10, and e.g. not more than 6 µm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, i.e. paramagnetic, and thus is displaceable under the action of that field. In other words, a support comprising magnetic particles may readily be removed by magnetic aggregation, which provides a quick, simple and efficient way of separating the particles following the analyte binding steps.

As noted above, in one embodiment the analyte is first captured by the immobilised or immobilisable capture probe which serves only to immobilise the analyte on the solid phase, and subsequently the immobilised analyte is incubated with the proximity probes. In such an embodiment, the capture probe may be any binding partner capable of binding the analyte, directly or indirectly (e.g. as discussed above in relation to the analyte-binding domain of the proximity probe). More particularly, such a capture probe binds specifically to the analyte. Since this embodiment of the method requires the simultaneous binding of at least three probes (binding domains) to the analyte or analyte complex, potentially at least three different epitopes can be interrogated, conferring high specificity on the assay.

In a further embodiment, the analyte itself may be immobilised (or immobilisable) on the solid phase e.g. by non-specific absorption. In a particular such embodiment, the analyte may be present within cells, being optionally fixed and/or permeabilised, which are (capable of being) attached to a solid support, e.g. a tissue sample comprising analyte may be immobilised on a microscope slide.

The above-described methods result in detection of proximity dependent interactions that are present in the reaction mixture, which in turn provides a measure of the amount of target analyte in the sample being assayed. The measure may be qualitative or quantitative.

Accordingly, the above described methods of detecting the presence of one or more target analytes in a sample finds use in a variety of different applications.

The subject methods may be used to screen a sample for the presence or absence of one or more target analytes in a sample. As indicated above, the invention provides methods of detecting the presence or quantifying the amount of one or more target analytes in a sample.

The subject methods can be employed to detect the presence of one or more target analytes in a variety of different types of samples, including complex samples having large amounts of non-target entities. The subject methods are highly sensitive methods of detecting one or more target analytes in a simple or complex sample. The sample that is assayed in the subject methods is, in many embodiments, from a physiological source, as discussed in more detail above.

In addition to detecting a wide variety of analytes, the subject methods may also be used to screen for compounds that modulate the interaction between the analyte binding domain of the proximity probe with the binding region of the analyte i.e. the binding of the analyte-binding domain to the analyte. The term modulating includes both decreasing (e.g., inhibiting) and enhancing the interaction between the two molecules.

As noted above, the methods of the invention find particular utility in the detection of proteins and protein interactions, for example in proteomic studies. Since they may be provided in an enzyme-free format, they are particularly useful for clinical or diagnostic application, particularly for point of care use. For such use, kits may conveniently be provided for practicing the methods of the invention.

Accordingly, in a further aspect, the invention also provides kits for use in the methods of the invention as hereinbefore defined. For example, in some embodiments, a kit will include at least one set of first and second proximity probes, as described above, together with at least one set of HCR monomers for performing an HCR reaction. Such kits may comprise further components, e.g. an activator oligonucleotide, or other means for introducing permissive conditions, and/or other reaction reagents. Such additional components or reagents include, but are not limited to one or more of the following: means for introducing permissive conditions (e.g. an activator oligonucleotide, or an enzyme or combination of enzymes such as a RNAase, nickase or uracil-DNA glycosylase enzyme), solid support for immobilisation, means for immobilisation, capture probe, detection means e.g. detection probes or reagents required to detect a labelled HCR monomer when polymerised, buffers, cations, etc. and the like. In certain embodiments, the kits may include elements employed in reducing the effective volume of an incubation mixture, as reviewed above, e.g., a volume excluder. The kit components may be present in separate containers, or one or more of the components may be present in the same container, where the containers may be storage containers and/or containers that are employed during the assay for which the kit is designed.

In addition to the above components, the kits may further include instructions for practicing the methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Accordingly, in a further aspect the present invention provides a kit for use in method for detecting an analyte in a sample, said kit comprising:

(a) at least one set of proximity probes comprising at least first and second proximity probes, which probes each comprise an analyte-binding domain capable of simultaneously binding directly or indirectly to said analyte and a nucleic acid domain, wherein (i) the nucleic acid domains of said first and second proximity probes comprise regions capable of mediating an interaction involving said domains when under permissive conditions; and (ii) the nucleic acid domain of one of said first and second probes comprises an HCR initiator region comprised within a metastable secondary structure such that it is unable to initiate an HCR reaction until released from said metastable secondary structure;

(b) optionally, means for introducing permissive conditions to allow the nucleic acid domains of said first and second probes to interact with each other when said probes have both bound directly or indirectly to the analyte, wherein said interaction results in unfolding of the metastable secondary structure of the nucleic acid domain of the second probe to release a single-stranded HCR initiator region;

(c) means for performing an HCR reaction, said means comprising at least two HCR monomers, wherein the first HCR monomer comprises a region of complementarity to the HCR initiator region; and (d) optionally, means for detecting the polymer.

In a more particular embodiment, in (a), the nucleic acid domain of the first probe comprises a first region of complementarity to a cognate second region of complementarity in the nucleic acid domain of the second probe, and said first region of complementarity is protected such that the first and second complementary regions are not able to hybridise to one another; and in (b) the means for introducing permissive conditions comprises means for deprotecting the first region of complementarity to allow the first and second complementary regions of the nucleic acid domains of said first and second probes to hybridise to each other when said probes have both bound directly or indirectly to the analyte, wherein said hybridisation results in unfolding of the metastable secondary structure of the nucleic acid domain of the second probe to release a single-stranded HCR initiator region. Preferably the deprotecting means is a an activator oligonucleotide.

The kit may further optionally comprise an immobilised capture probe for the analyte, or a capture probe provided with means for immobilisation. Alternatively, the kit may comprise a solid phase for capture of, or binding to, the analyte, or one or more of said first or second proximity probes may be immobilised or provided with means for immobilisation.

Also provided as part of the invention is a set of proximity probes comprising at least first and second proximity probes, which probes each comprise an analyte-binding domain capable of simultaneously binding directly or indirectly to an analyte to be detected, and a nucleic acid domain, wherein (i) the nucleic acid domains of said first and second proximity probes comprise regions capable of mediating an interaction involving said domains when under permissive conditions; and (ii) the nucleic acid domain of one of said first and second probes comprises an HCR initiator region comprised within a metastable secondary structure such that it is unable to initiate an HCR reaction until released from said metastable secondary structure.

In preferred embodiments, the nucleic acid domains of both proximity probes contains a metastable secondary structure, as discussed above, and in particular both proximity probes comprise a nucleic acid domain comprising (or with) a hairpin structure.

In a still further aspect the present invention also provides an antibody capable of binding directly or indirectly to an analyte to be detected, and having a nucleic acid domain attached thereto, wherein said nucleic acid domain comprises a region capable of interacting with (e.g. hybridising with) another nucleic acid molecule, and said interacting region is contained within a metastable secondary structure in said domain, which structure is capable of being unfolded to release said interacting region, said unfolding not being mediated by cleavage of the nucleic acid domain.

Thus, in this aspect of the invention, the nucleic acid domain is unfolded by a conformational change in the secondary structure of nucleic acid domain which results in release of the interacting domain. More particularly, the secondary structure itself is released, or unfolded, without a cleavage of a phosphodiester bond in said nucleic acid domain, i.e without the domain itself being cleaved. The antibody is preferably a proximity probe and the interacting region will preferably be a complementary region capable of hybridising to a cognate complementary region in the nucleic acid domain of another proximity probe.

In an alternative embodiment, the interacting region comprises an HCR initiator (or alternatively expressed, the interacting region comprises a sequence capable of acting as the initiator of an HCR reaction, or said interacting region is a HCR initiator region.

The invention will be further described with reference to the following non-limiting Examples with reference to the following drawings in which:

FIG. 1 shows the principle underlying prox-HCR. In this embodiment the first region of complementarity of the first probe is protected by a metastable hairpin structure, and the first and second probes are unable to interact. Upon addition of the activator oligonucleotide, which contains a region of complementarity to a cognate region of complementarity in the nucleic acid domain of the first probe, the first probe unfolds. The unfolded domain interacts with a region of complementarity in the nucleic acid domain of the second probe and exposes the HCR initiator sequence which subsequently initiates HCR.

Figure 5A:
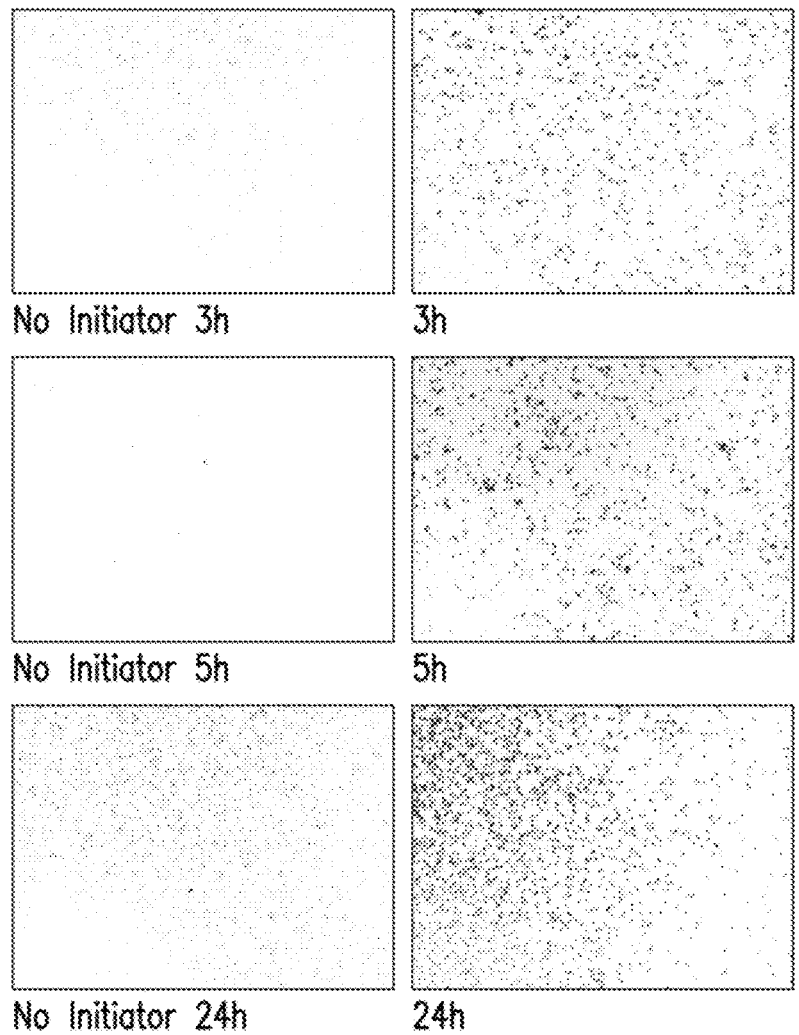
Figure 5B:
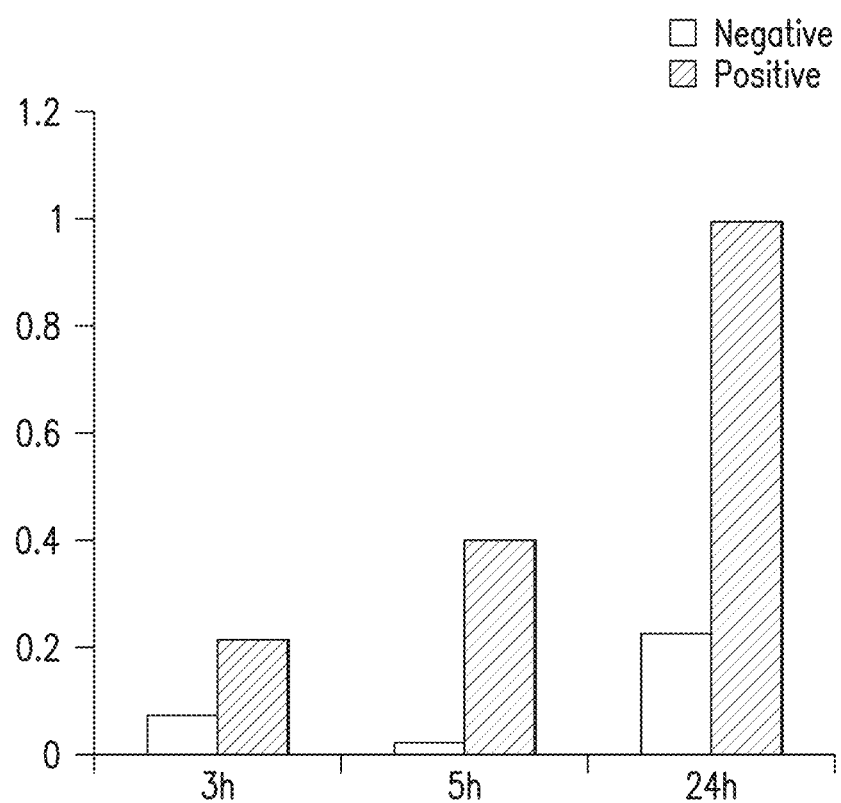

FIGS. 5A and 5B show the stability of the prox-HCR product over time using the reaction conditions of FIG. 2. FIG. 5A shows that up to 24 hours after addition of the HCR oligonucleotides the fluorescent signal is still detectable, and is higher for the (+) sample than the (−) sample. FIG. 5B shows the fluorescence intensity of the (+) and (−) samples after 2, 5 and 24 hours.

Figure 6:
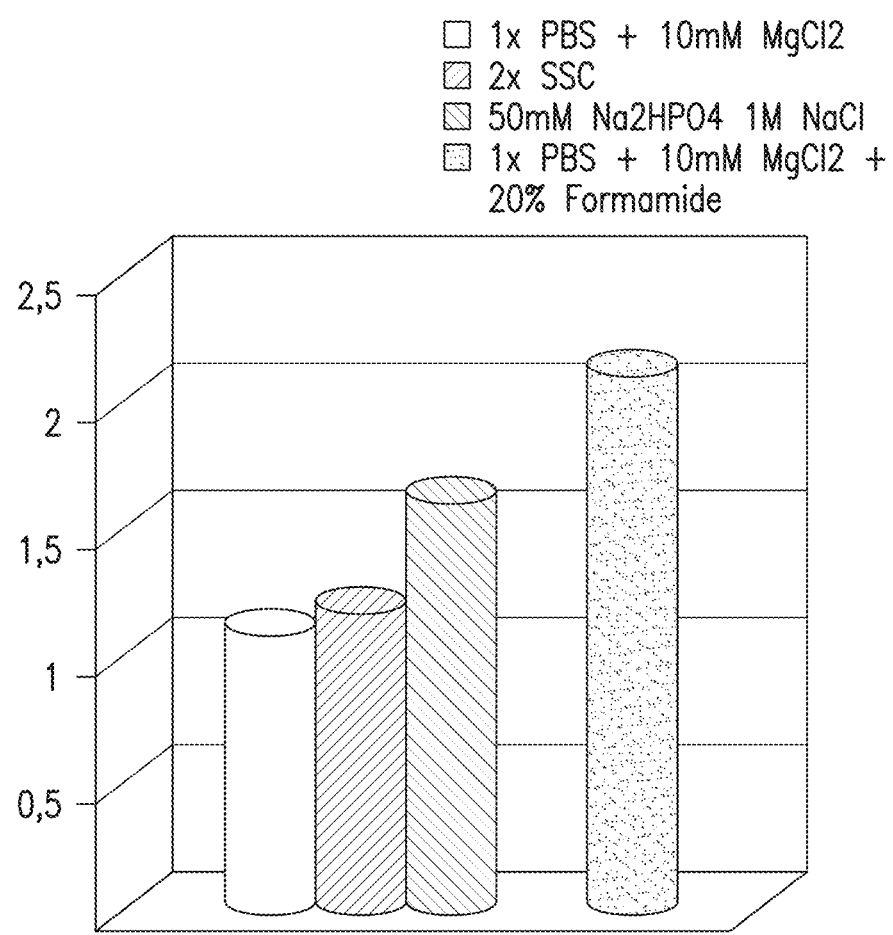

FIG. 6 shows the signal/noise ratios for a variety of the buffer conditions to test the effect of ionic strength on HCR.

Figure 7:
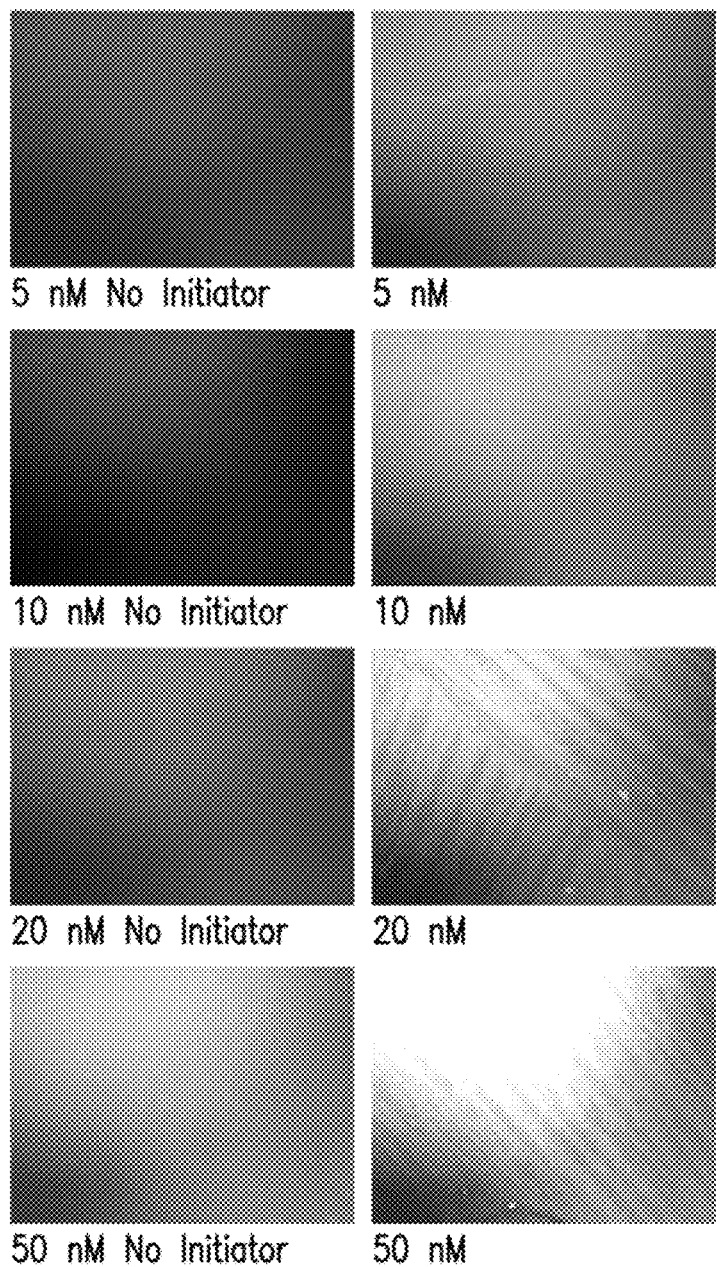

FIG. 7 shows the detection of streptavidin immobilised on microscopy slides via prox-HCR using biotinylated proximity hairpins. This shows that HCR can be used to specifically detect an analyte in a solid-phase assay.

Figure 8A:
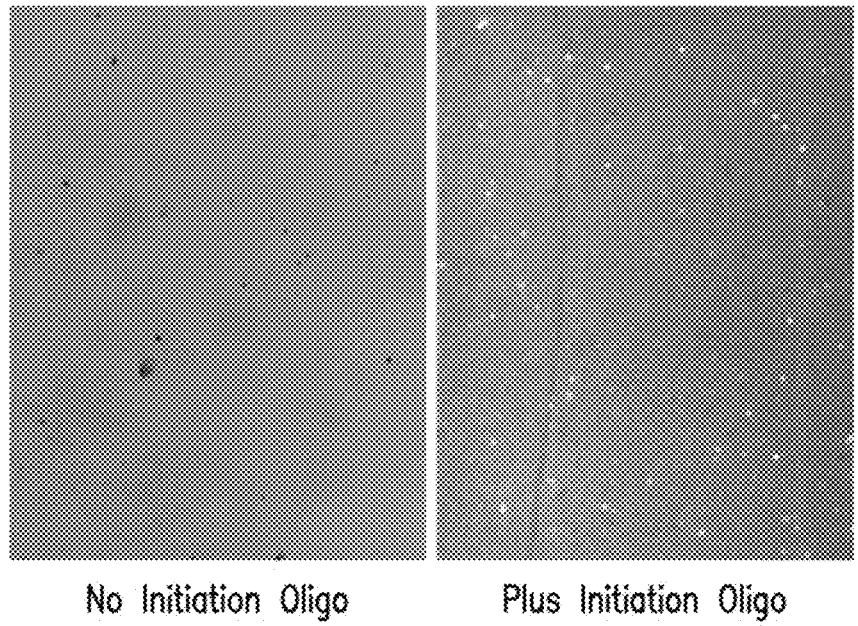
Figure 8B:
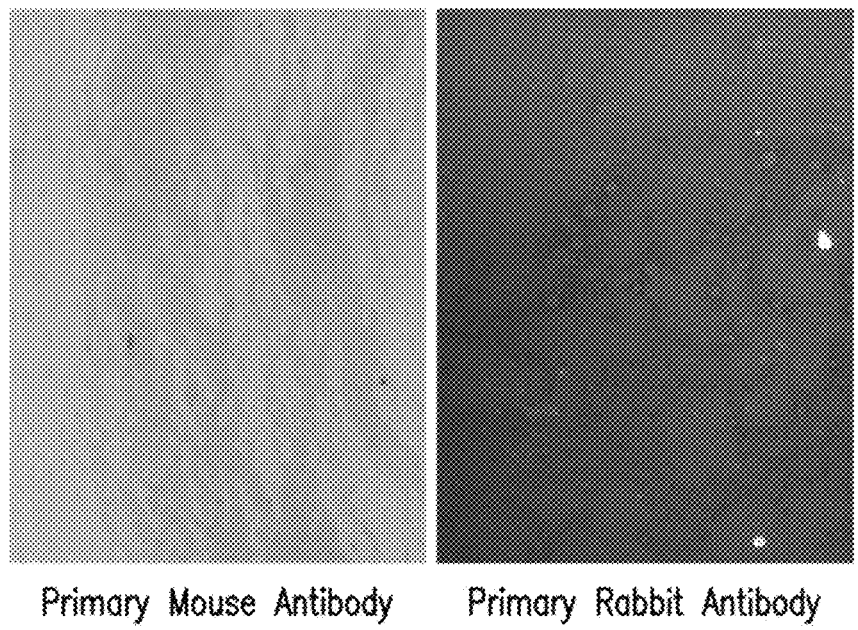

FIGS. 8A and 8B show the detection of a specific analyte using antibody-conjugated proximity hairpins. FIG. 8A shows that dried-in rabbit antibody can be detected via HCR. FIG. 8B shows that detection is dependent on the specific recognition of the analyte by the analyte-binding domain.

Figure 9A:
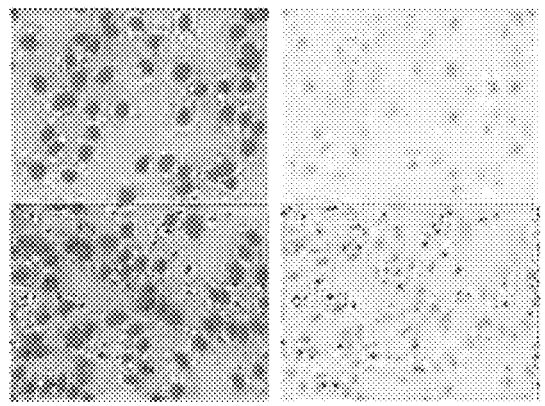
Figure 9B:
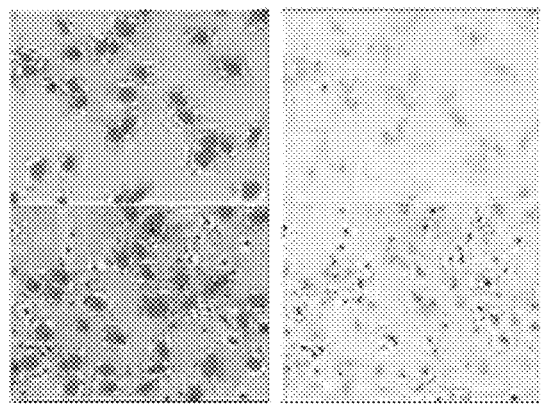
Figure 9C:
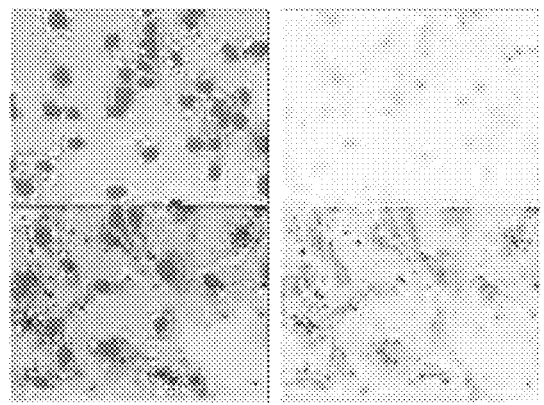

FIGS. 9A-9C show the detection of specific analytes within a cell sample using prox-HCR. This shows that a range of different analytes can be detected within a cell sample.

Figure 10:
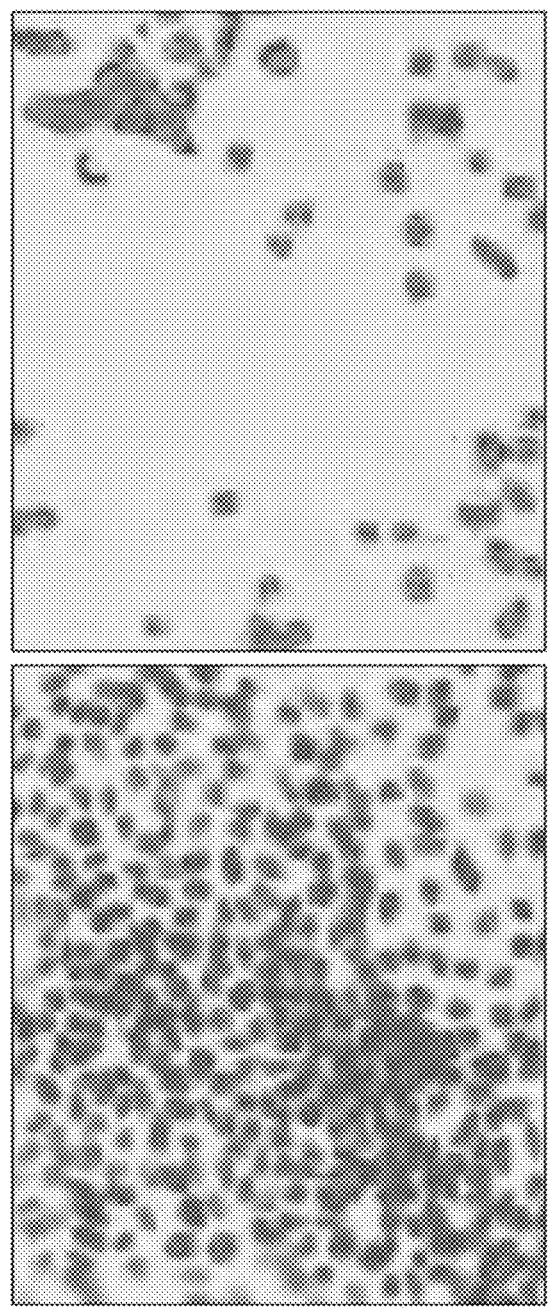

FIG. 10 shows the detection of a protein-protein complex in a cell sample. This shows that prox-HCR can be used to detect a protein-protein complex within a sample using proximity hairpins conjugated to antibodies targeting different components of the complex.

Figure 11A:
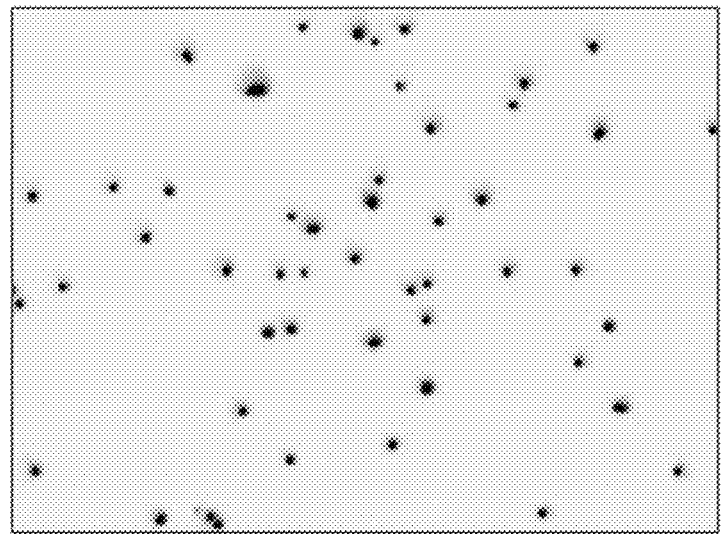
Figure 11B:
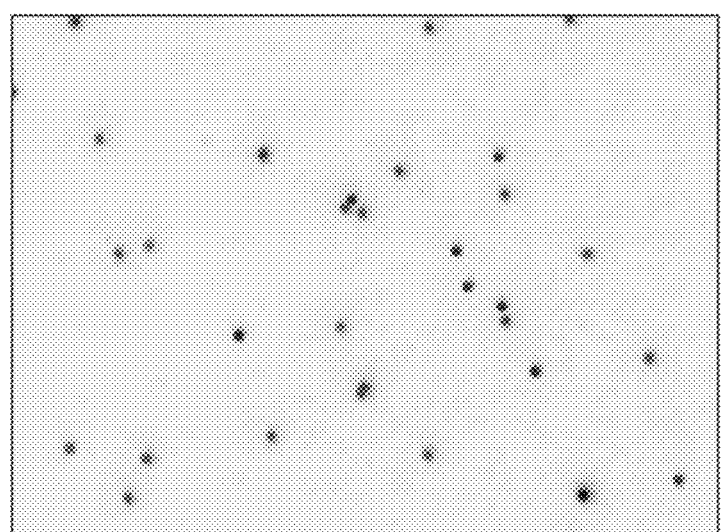

FIGS. 11A and 11B show the effect of introducing a mismatch into the second complementary region on nonspecific activation. FIG. 11A: The second complementary region in PH2 is complementary to the sequence in the activator oligonucleotide. FIG. 11B: The second complementary region in PH2 is complementary to the sequence in the activator oligonucleotide, but contains 2 mismatches. The presence of the mismatches reduces the false-positive activation by the activator oligonucleotide in the absence of the PH1 sequence.

Figure 12A:
Figure 12B:
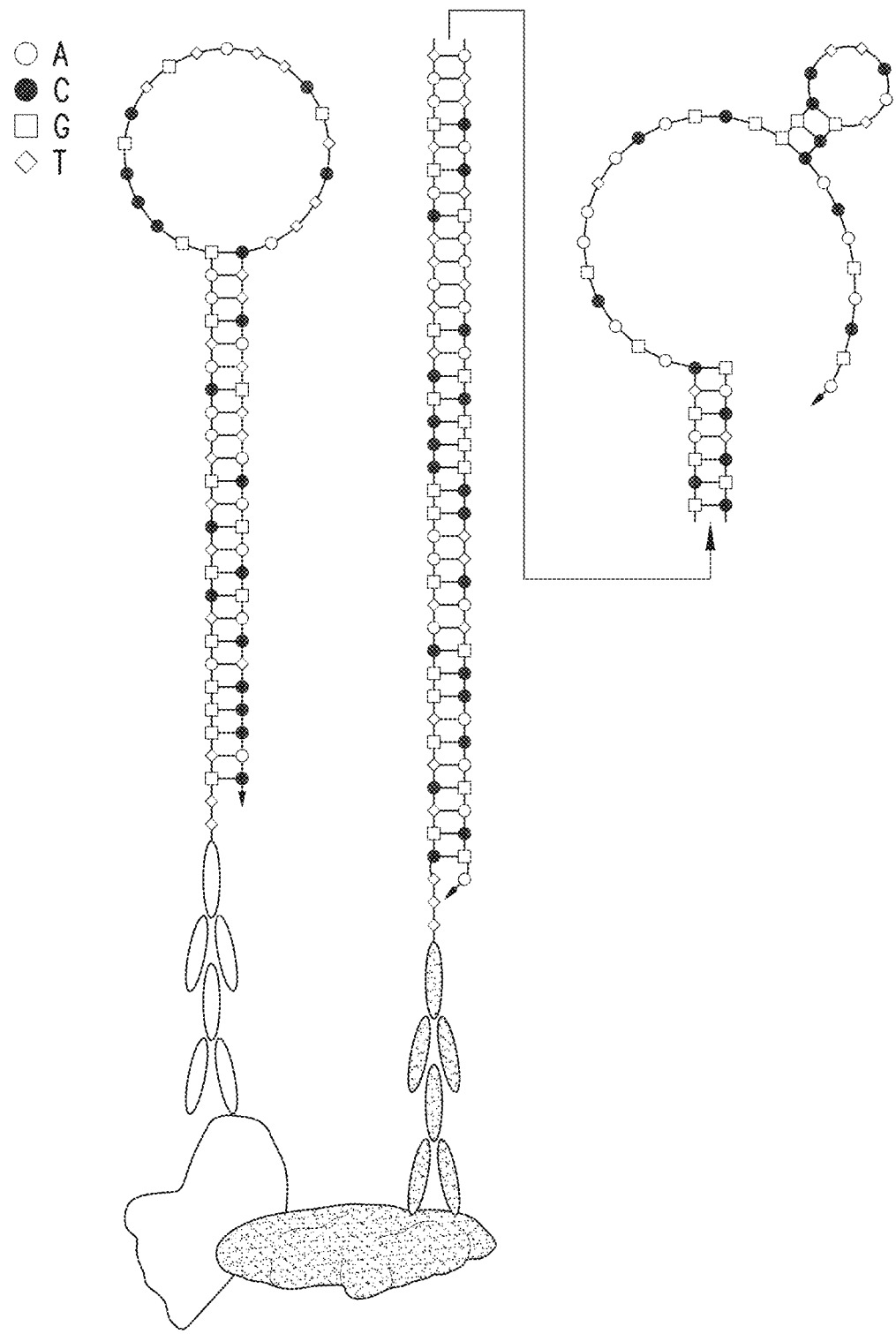
Figure 12C:
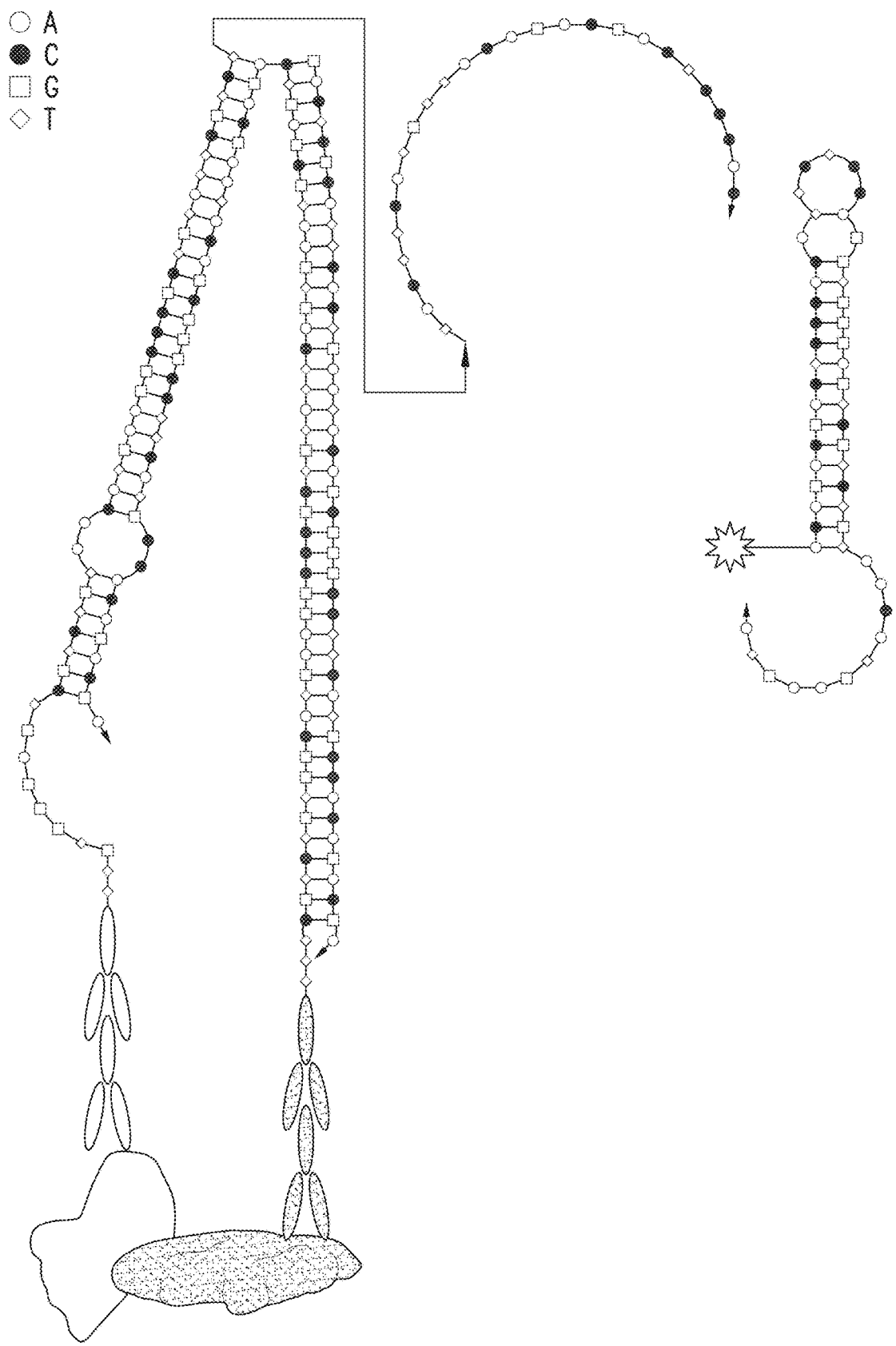
Figures 12D, 12E:
Figure 12E:
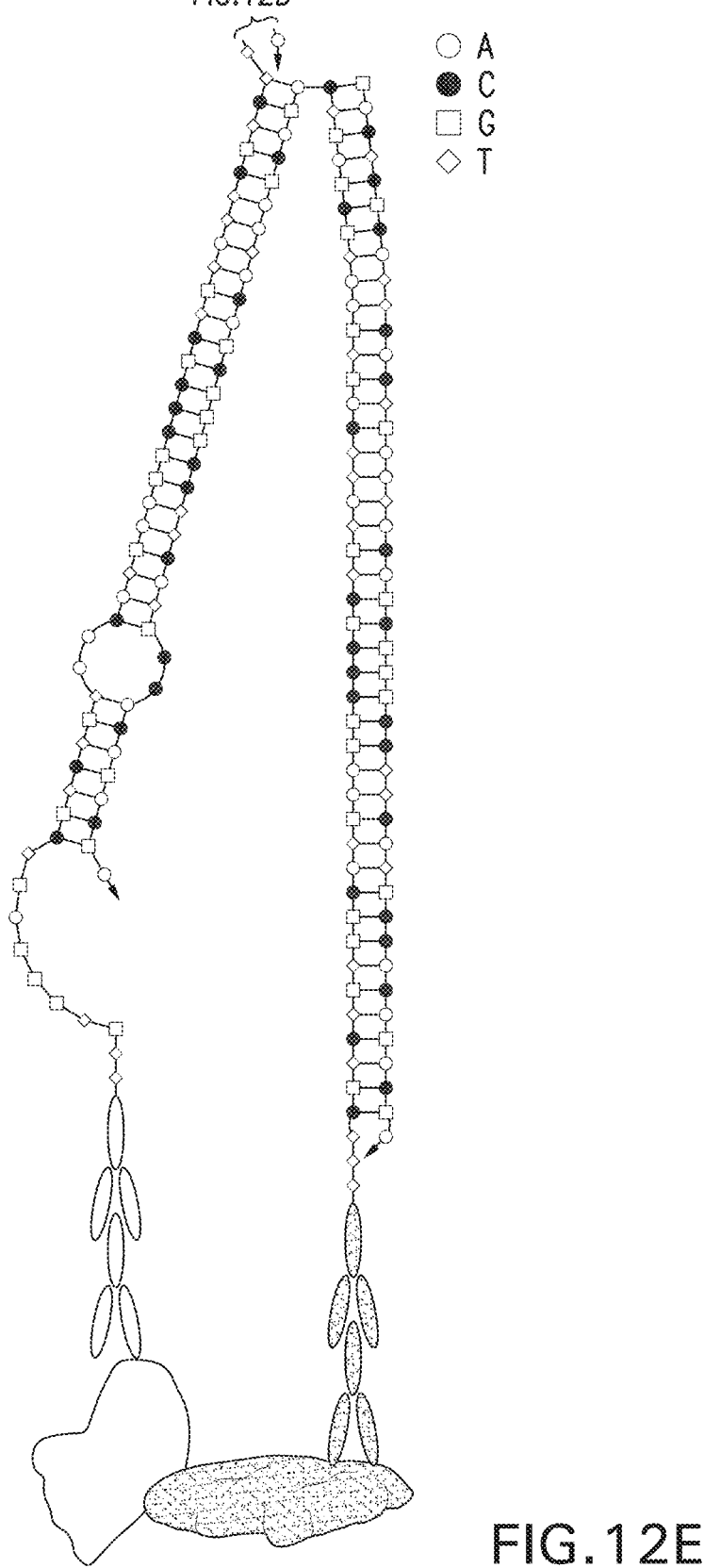
Figures 12F, 12G:
Figure 12G:
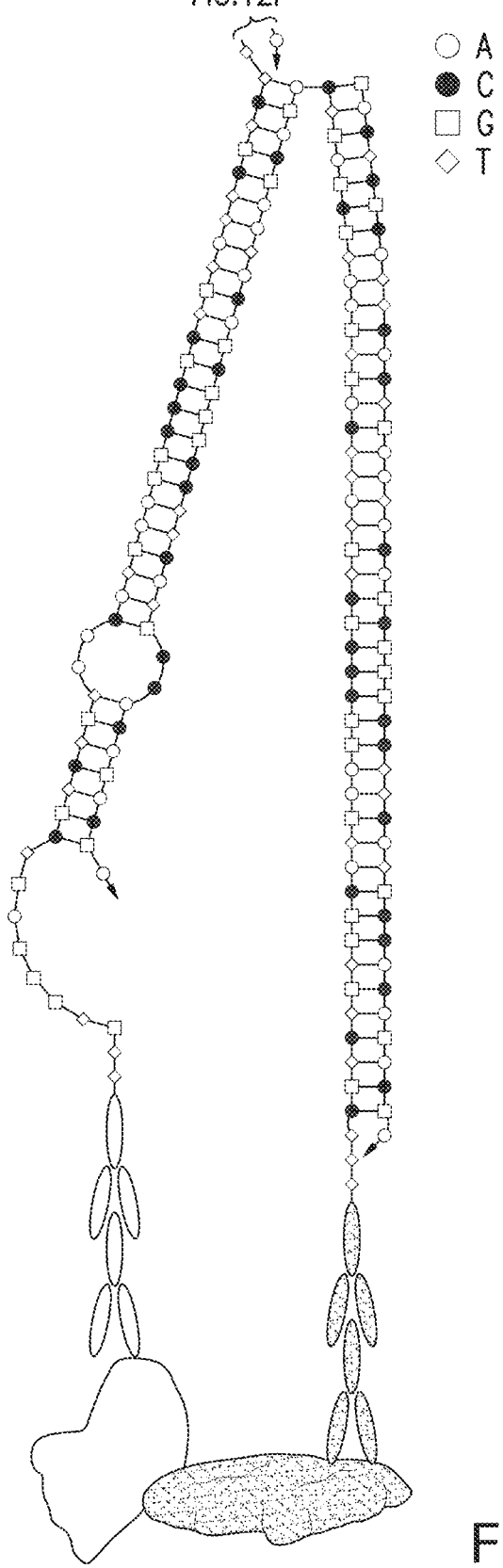
Figure 12H:
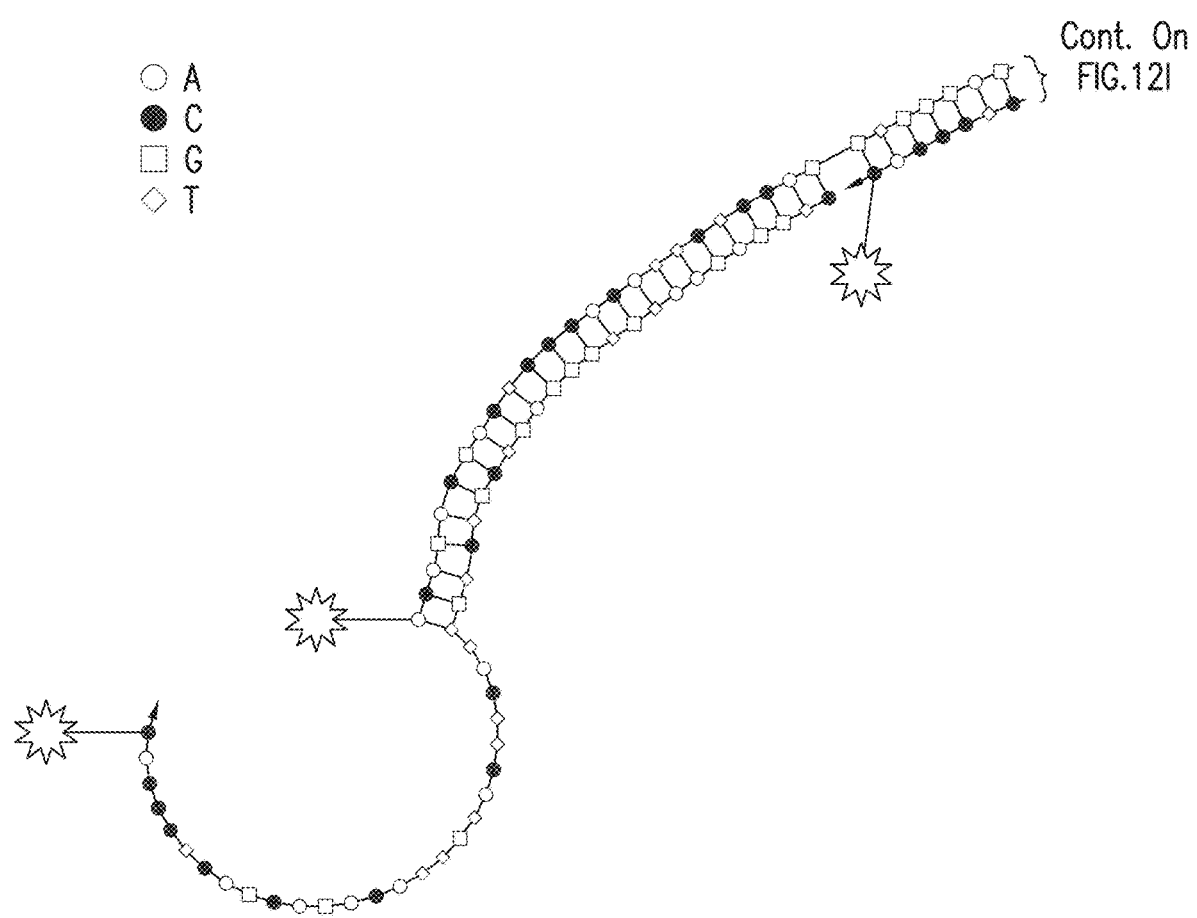
Figure 12I:
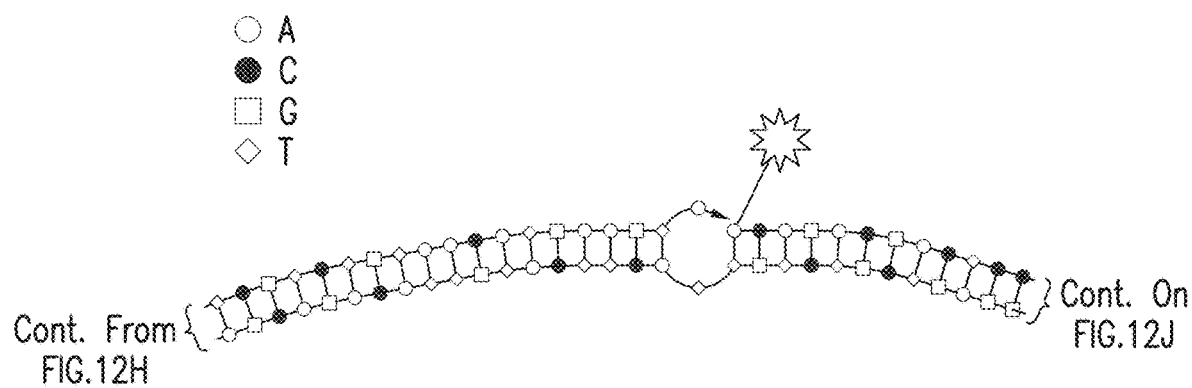
Figure 12J:
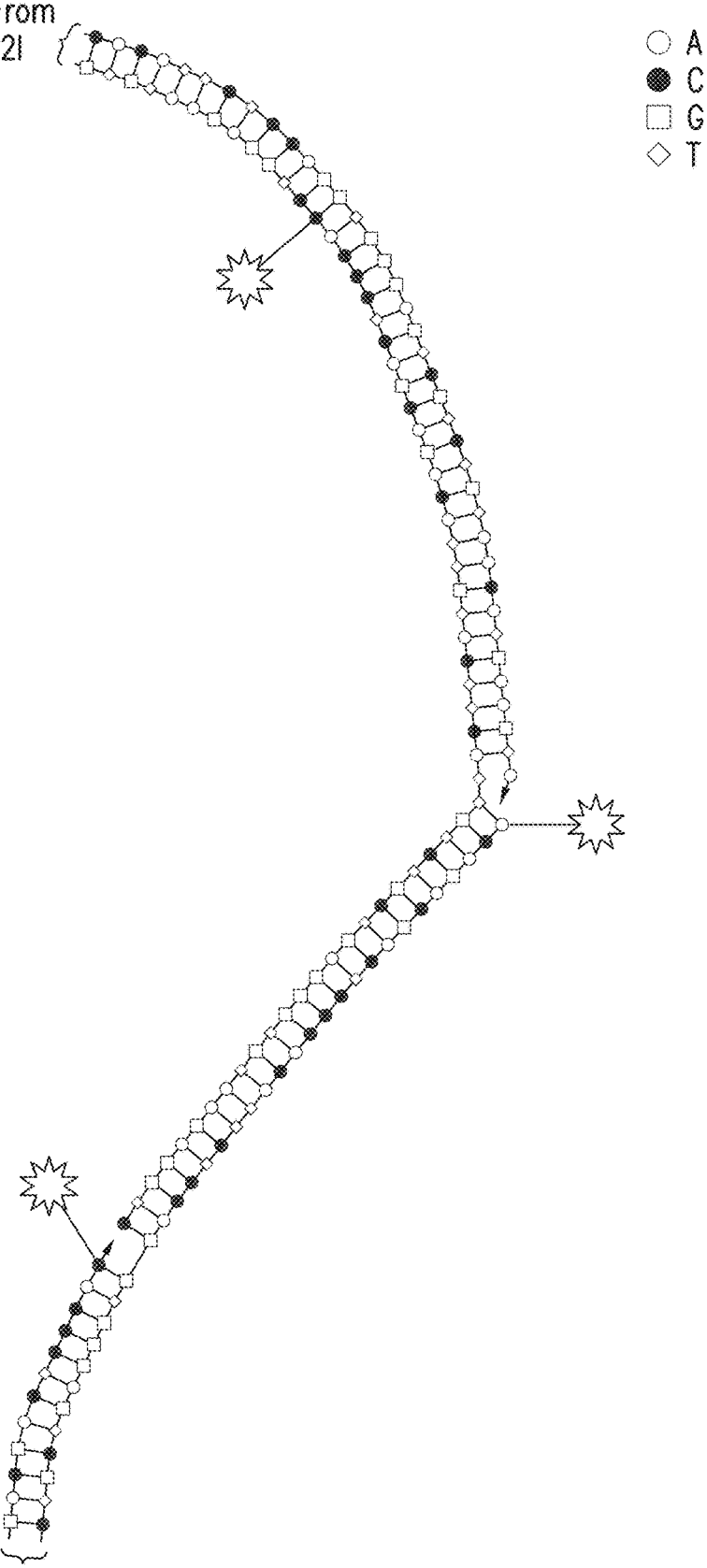
Figure 12K:
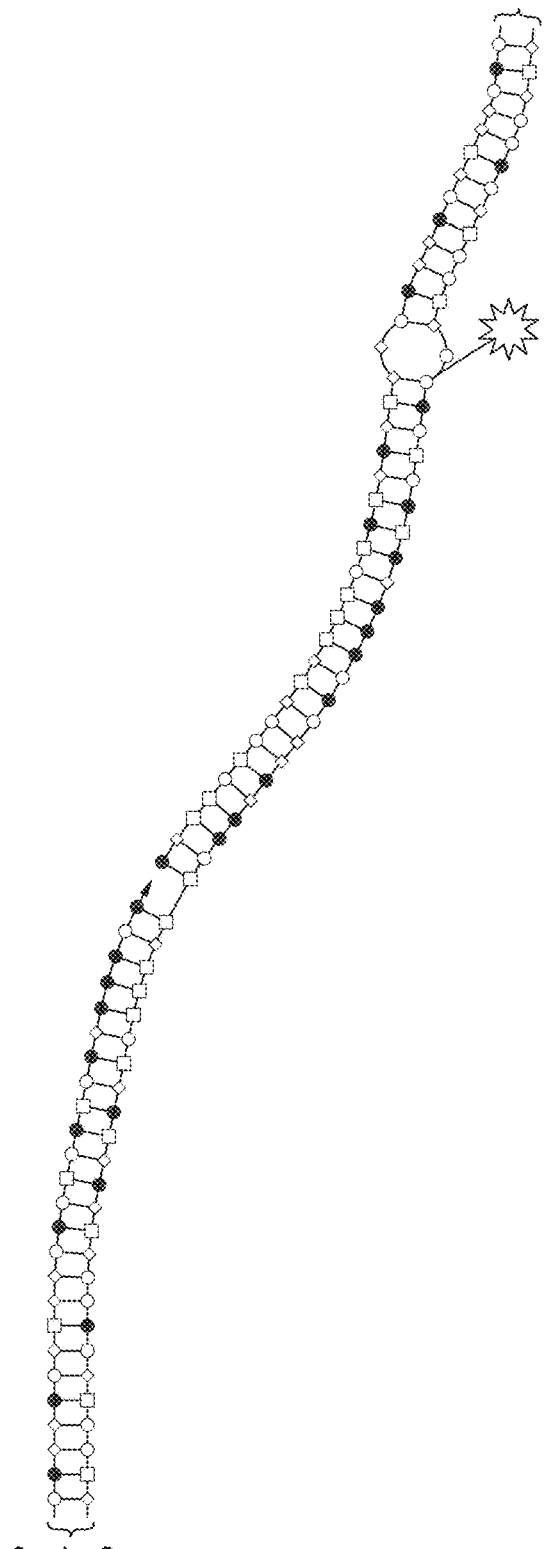
Figure 12L:
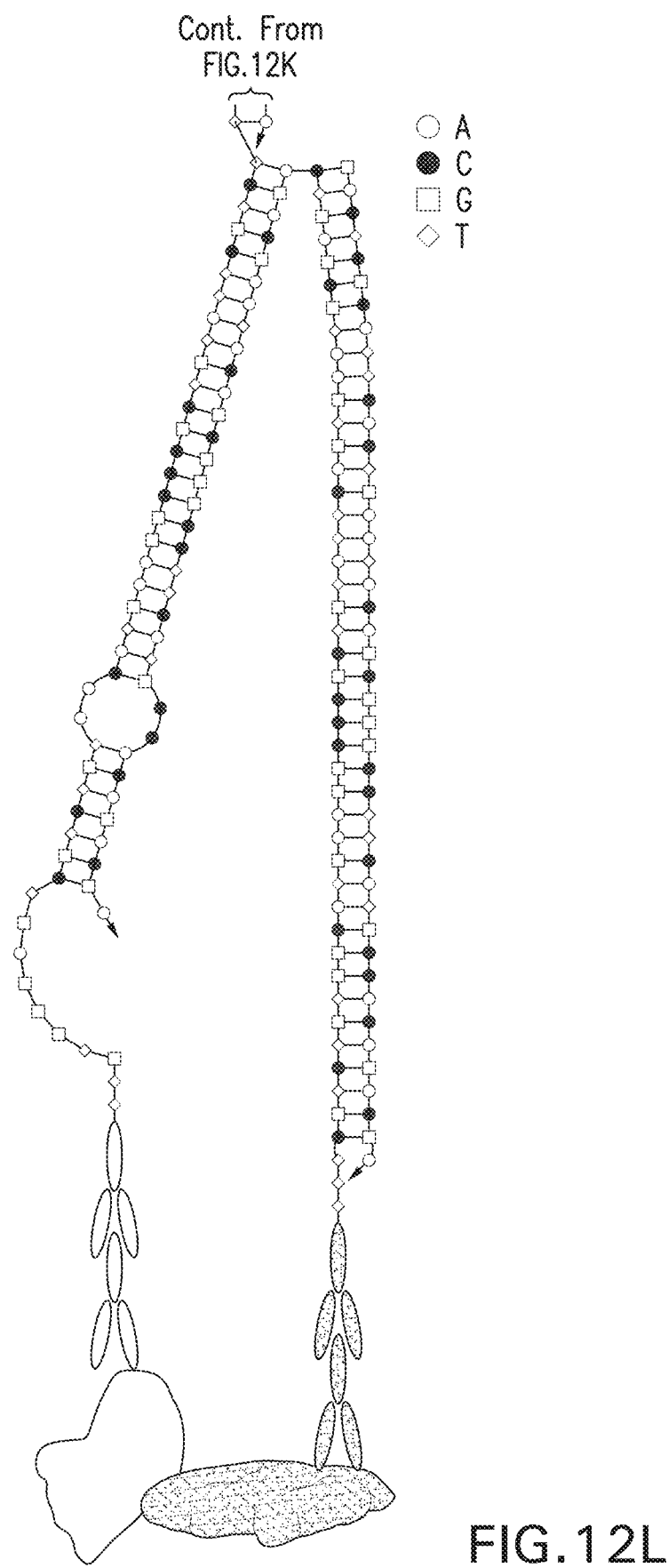

FIGS. 12A-12F show the principle underlying prox-HCR in more detail. FIG. 12A: Primary antibodies bind to their respective targets and are bound by proximity probes. FIG. 12B: The activator oligonucleotide binds in the loop of the hairpin of the nucleic acid domain of the first proximity probe and invades the stem, thereby releasing the first region of complementarity. FIG. 12C: The first region of complementarity binds to the loop of the hairpin of the nucleic acid domain of the second proximity probe, releasing the HCR initiator region. FIGS. 12D-12E: The HCR initiator region binds to the first HCR monomer. FIGS. 12F-12G: The first HCR monomer binds to the second HCR monomer. FIGS. 12H-L: Successive binding of the first and second HCR monomer forms an HCR polymer.

Figure 13A:
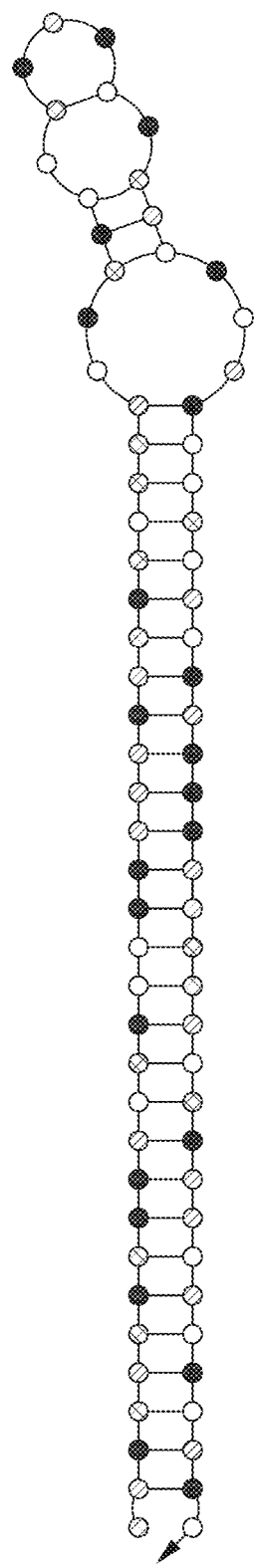
Figure 13B:
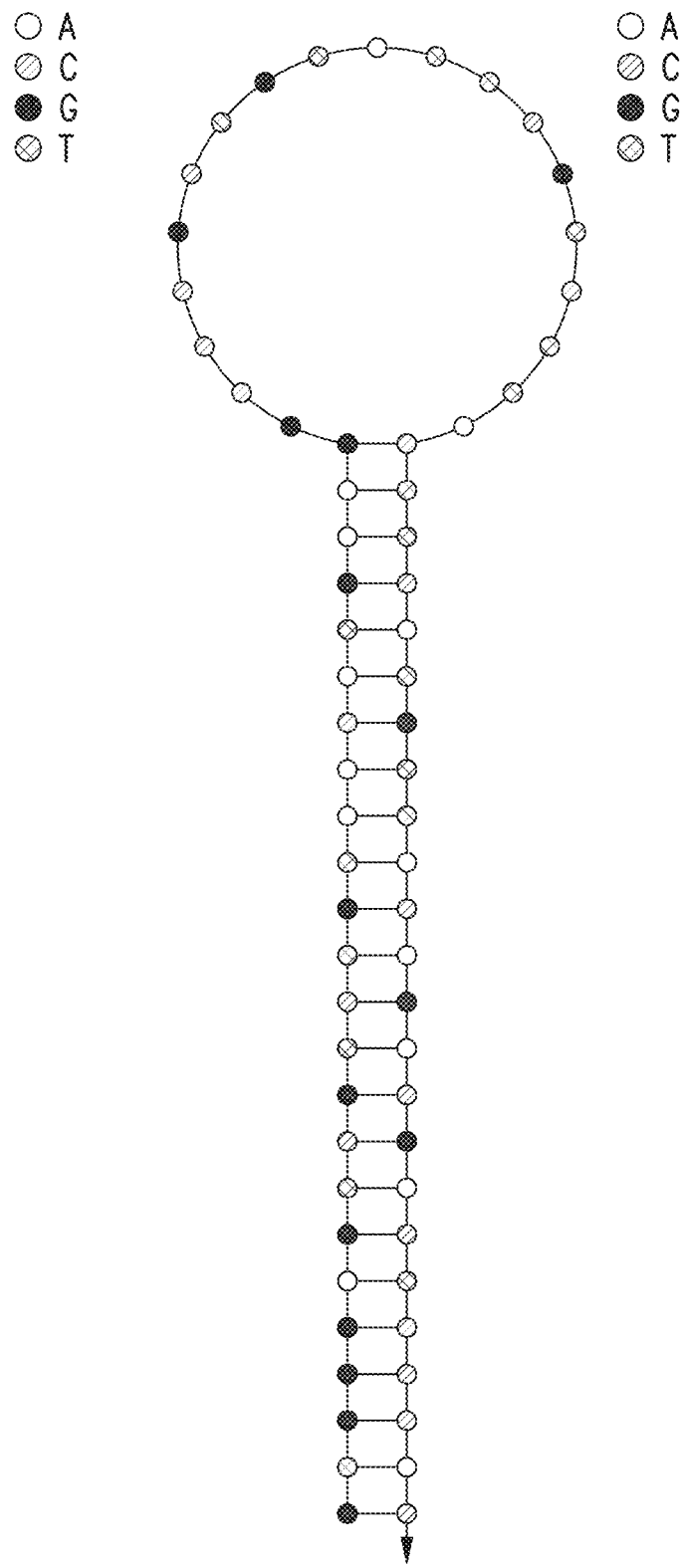
Figure 13C:
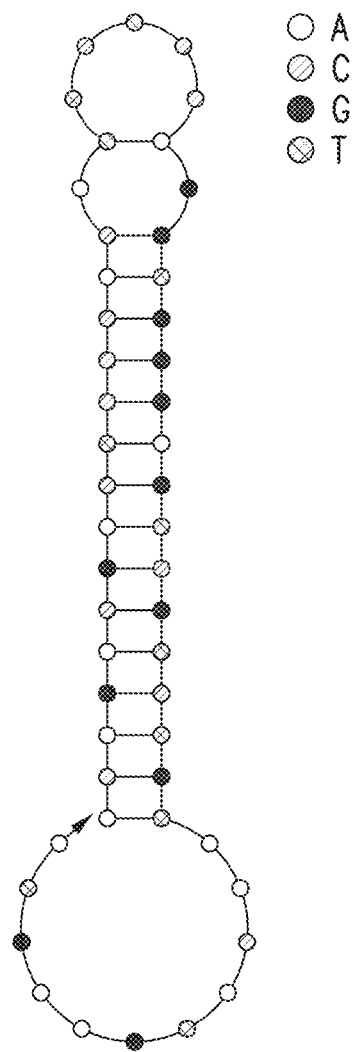
Figure 13D:
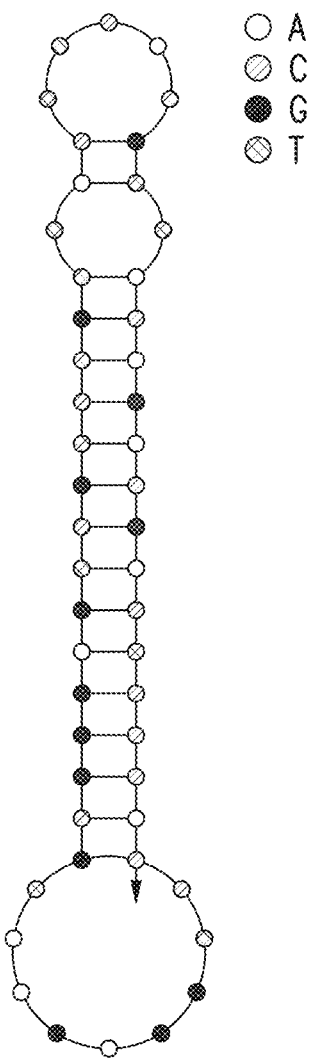

FIGS. 13A-13D show representative oligonucleotide molecules suitable for use in the prox-HCR method of the invention. FIGS. 13A and 13B show representative nucleic acid domains of the first and second proximity probes, having 30 bp stem and 18 nt loop, and 24 bp stem and 19 nt loops respectively. FIGS. 13C and 13D show representative HCR monomers having a short sticky end, stem, and loop structures (9 nt 5' end, 15 bp stem and 11 nt loop; and 11 nt 3', 15 bp stem and 9 nt loop respectively). The oligonucleotide sequences are shown in Table 2.

Figure 14A:
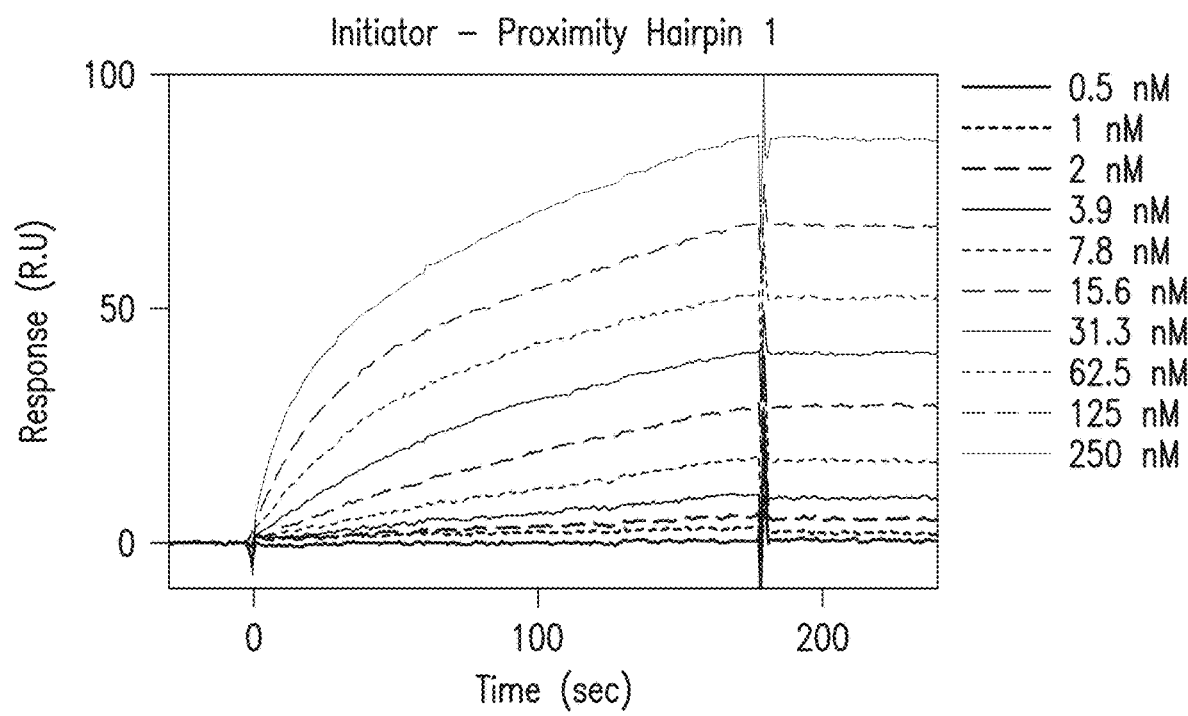
Figure 14B:
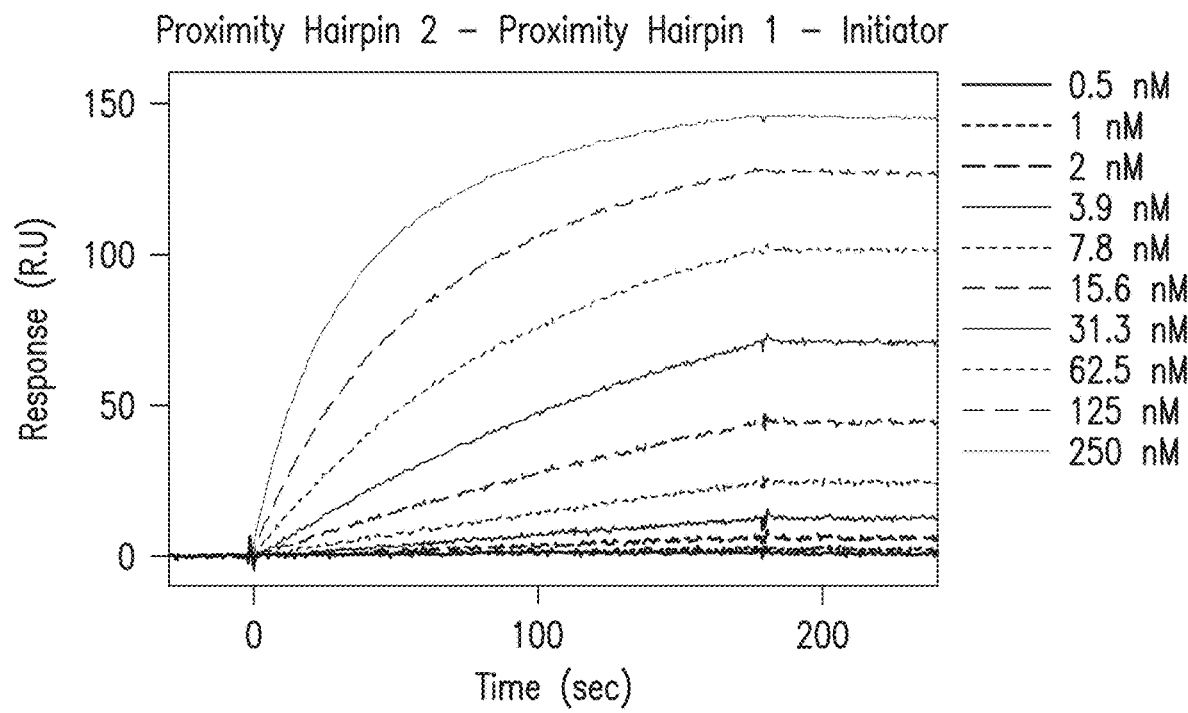
Figure 14C:
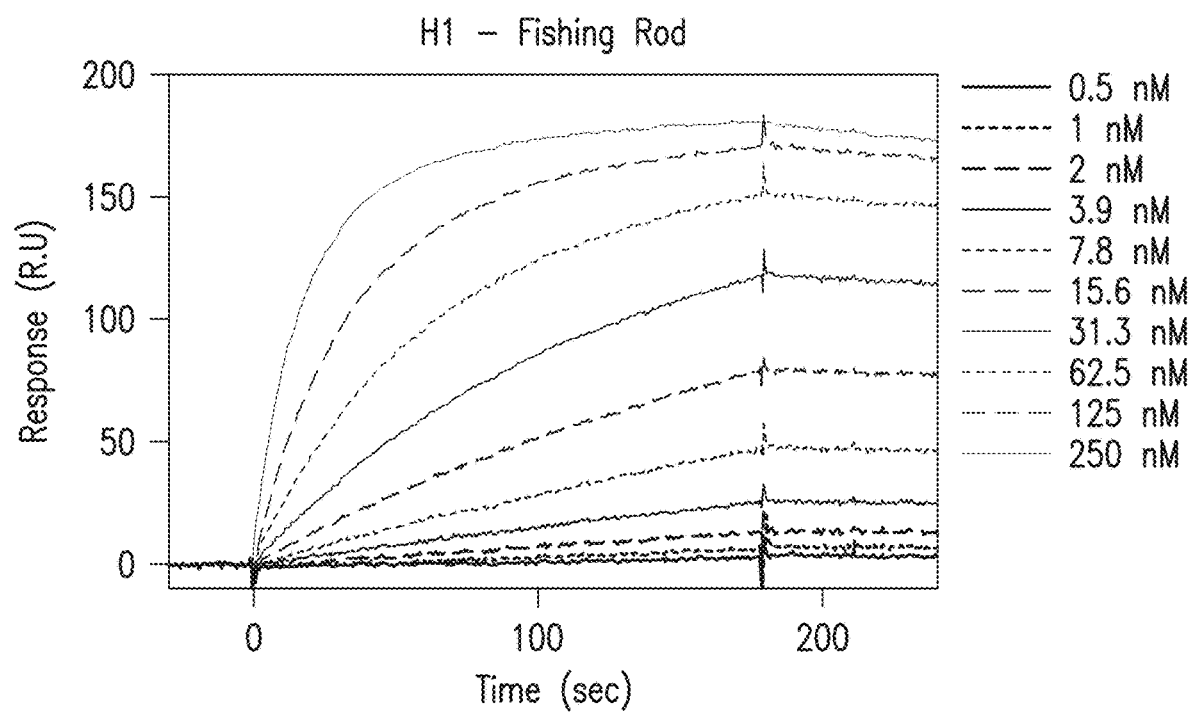
Figure 14D:
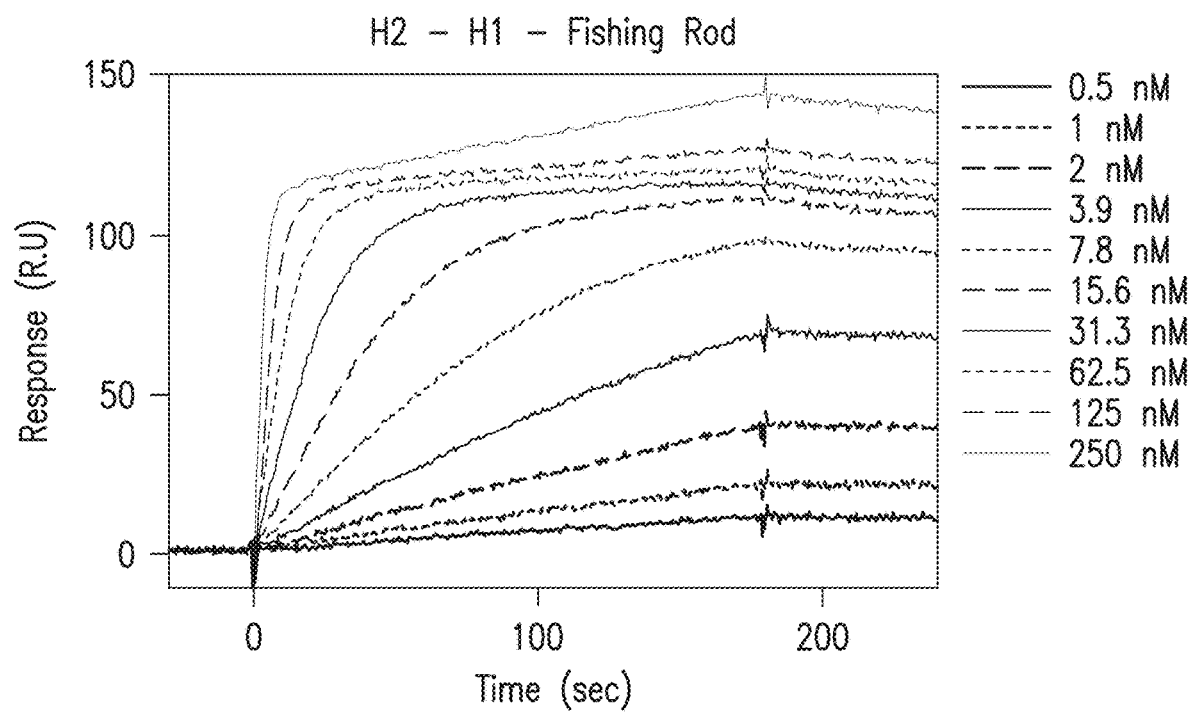

FIGS. 14A-14D show the progression of the HCR method, monitored by surface plasmon resonance. FIG. 14A: Titration series showing binding of the activator oligonucleotide to immobilised proximity hairpin 1. FIG. 14B: Subsequent binding of proximity hairpin 2 to proximity hairpin 1. FIG. 14C: Titration series showing binding of HCR monomer 1 to an immobilised 'fishing rod' sequence (mimicking the HCR initiator region). FIG. 14D: Subsequent binding to HCR monomer 2 to HCR monomer 1.

Figure 15A:
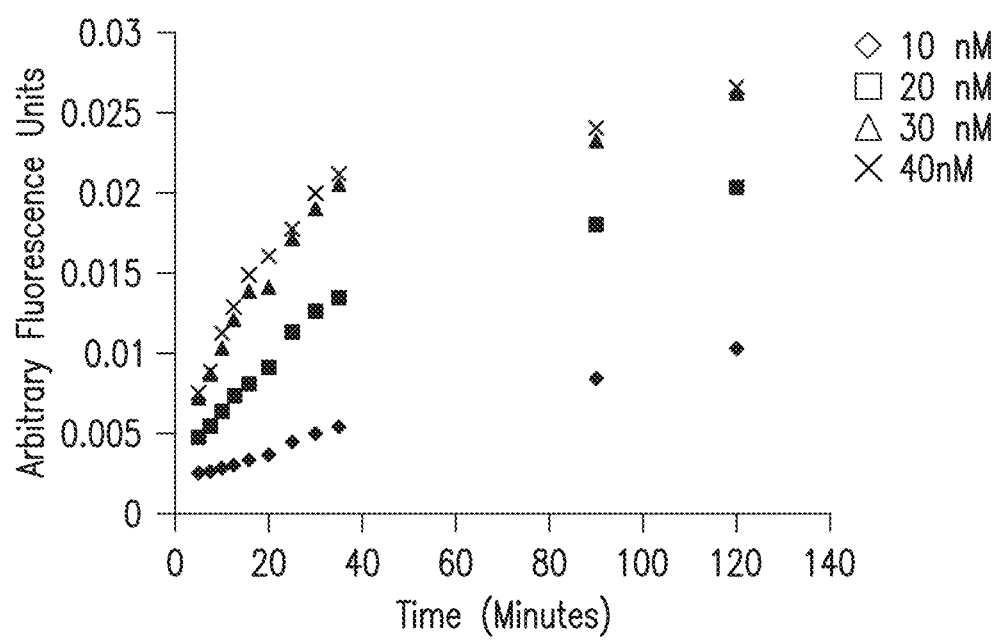
Figure 15B:
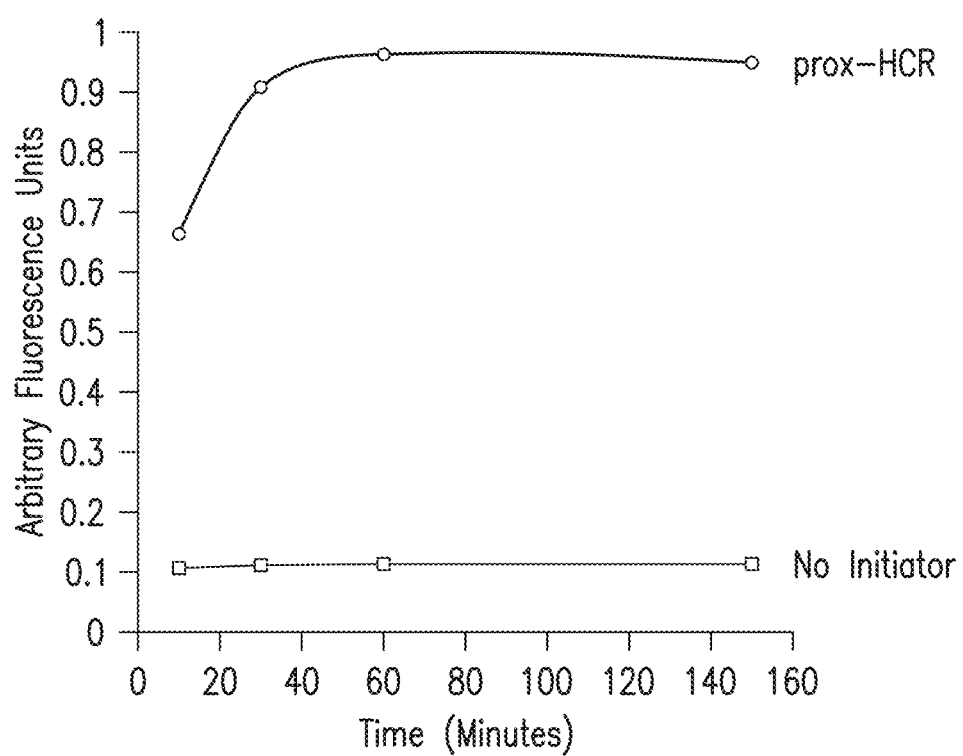
Figure 15C:
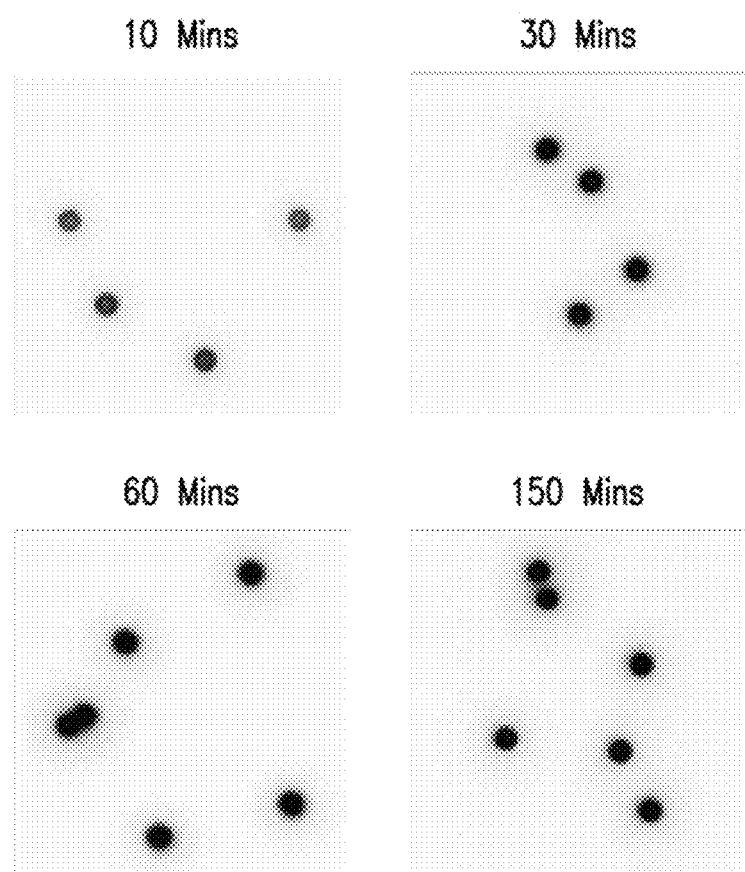

FIGS. 15A-15C show a time course experiment for the progression of the HCR reaction. FIG. 15A: Opera High Content Screening System to determine the build-up of fluorescence on beads at different concentrations. This shows a robust increase in fluorescence after only 30 min of incubation at 37° C. Even as early as 5 min incubation time was enough to see a dose-dependent (concentration of HCR oligonucleotides) increase in fluorescence. FIG. 15B: Epifluorescent microscopy images of beads incubated in the presence of 50 nM HCR oligonucleotides. Maximum fluorescence after 30 min and did not increase with longer incubation time. Signal was already distinguishable from the negative control after the earliest time point (10 min). Furthermore the negative control did not generate a visible amount of signal over the whole time period. FIG. 15C: Images of beads.

Figure 16A:
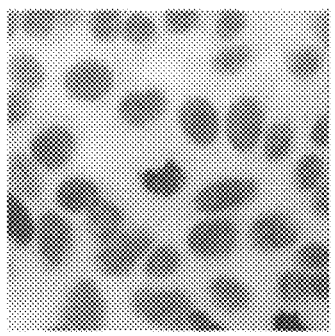
Figure 16B:
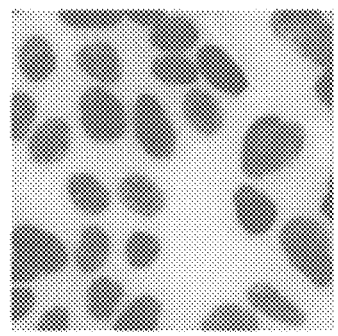
Figure 16C:
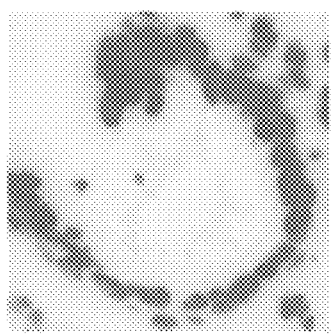
Figure 16D:
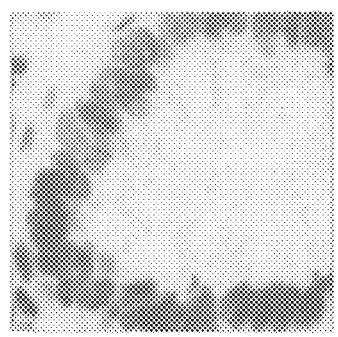
Figure 16E:
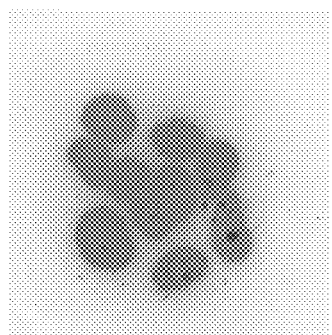
Figure 16F:
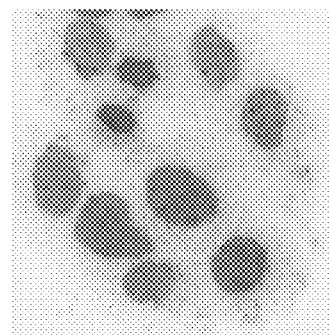
Figure 16G:
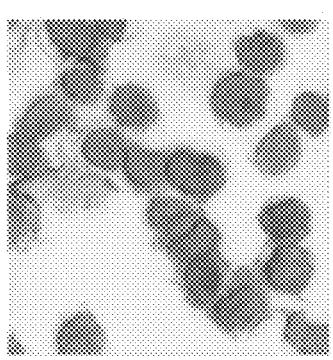
Figure 16H:
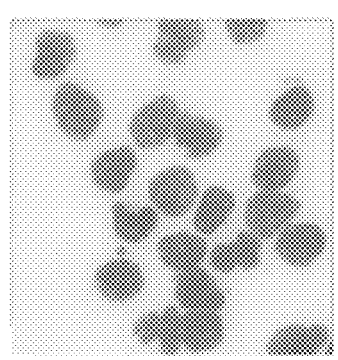

FIGS. 16A-16H show further in situ data for prox-HCR. FIGS. 16A-16D: A comparison of prox-HCR ((A) and (C)) and in situ PLA ((B) and (D)) for the detection of the interaction between E-cadherin and catenin in cell and tissue samples. A) and B) the pattern of the distribution is similar for prox-HCR and in situ PLA in DLD1 cells. C) and D) the pattern of the distribution is also similar in a colon tissue section. When looking at the actual number of generated signals it is clear that prox-HCR is more efficient than in situ PLA. On the other hand the signals that are generated in PLA are a lot stronger than those produced by prox-HCR. FIGS. 16E and 16F: Visualisation of the phosphorylation of PDGFR-ß in untreated cells and BjhTert cells stimulated with 100 ng mL-1 PDGF-BB. FIG. 16G: Visualisation of the phosphorylation of Syk in HG3 cells. FIG. 16H: Negative control (no primary antibodies). Both assays showed strong signal in the positive samples while fluorescence was low in the biological negative control and absent in the technical control.

Figure 17A:
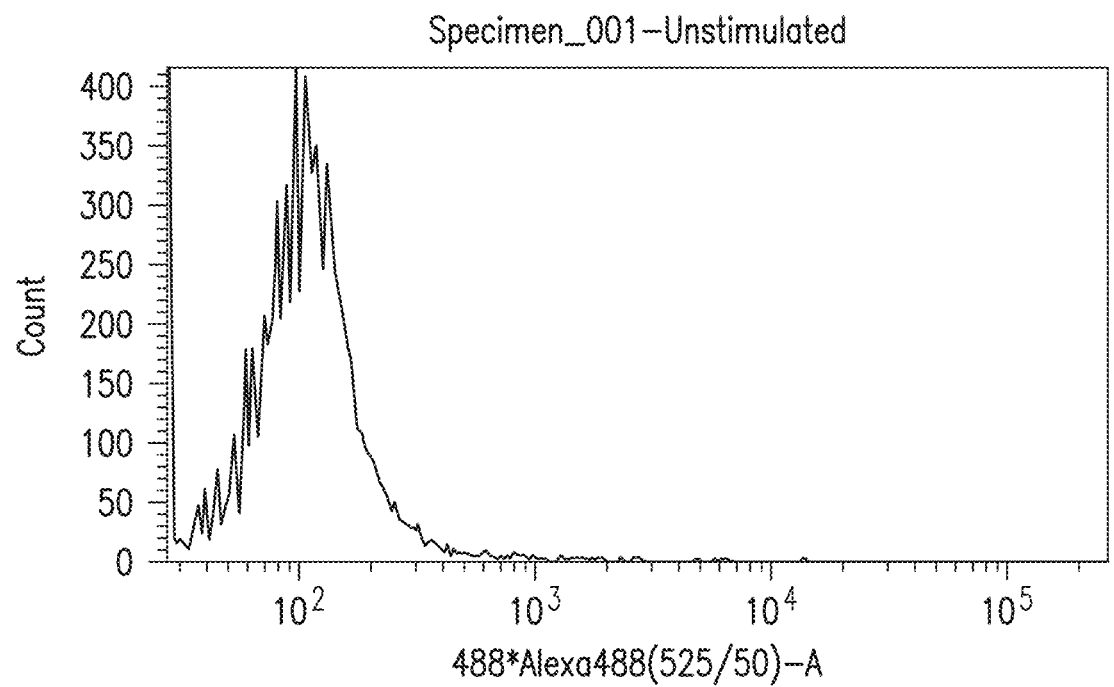
Figure 17B:
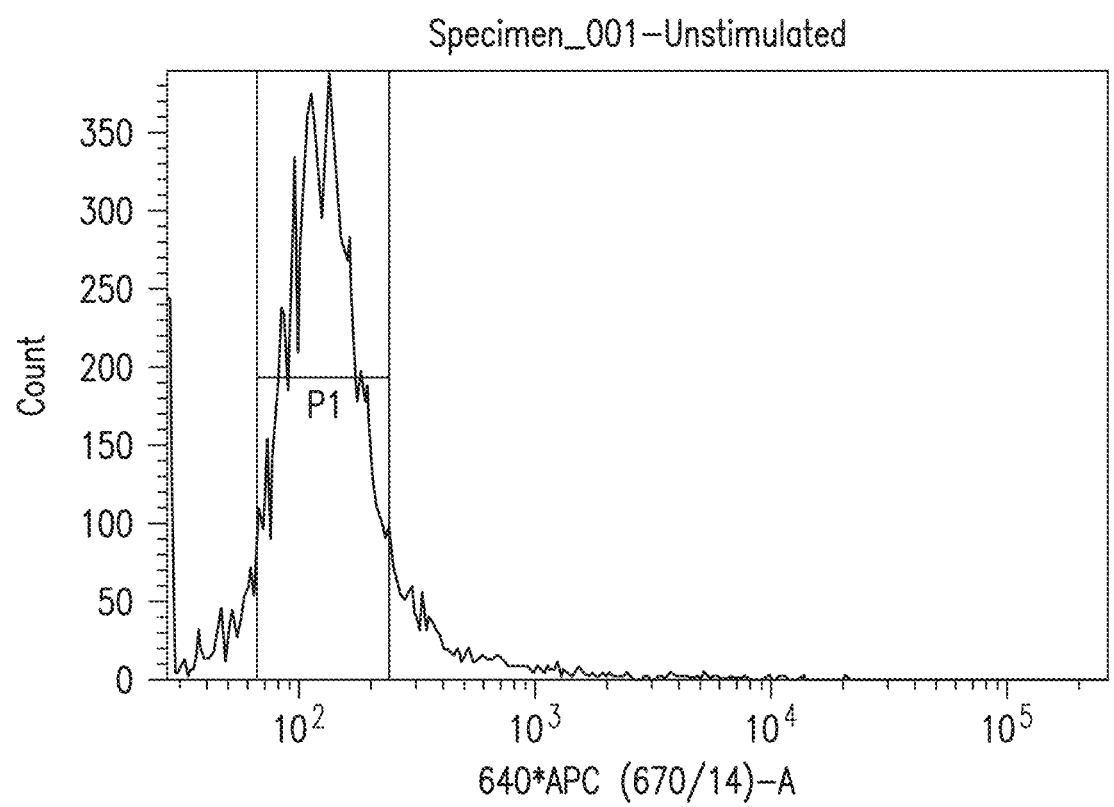
Figure 17C:
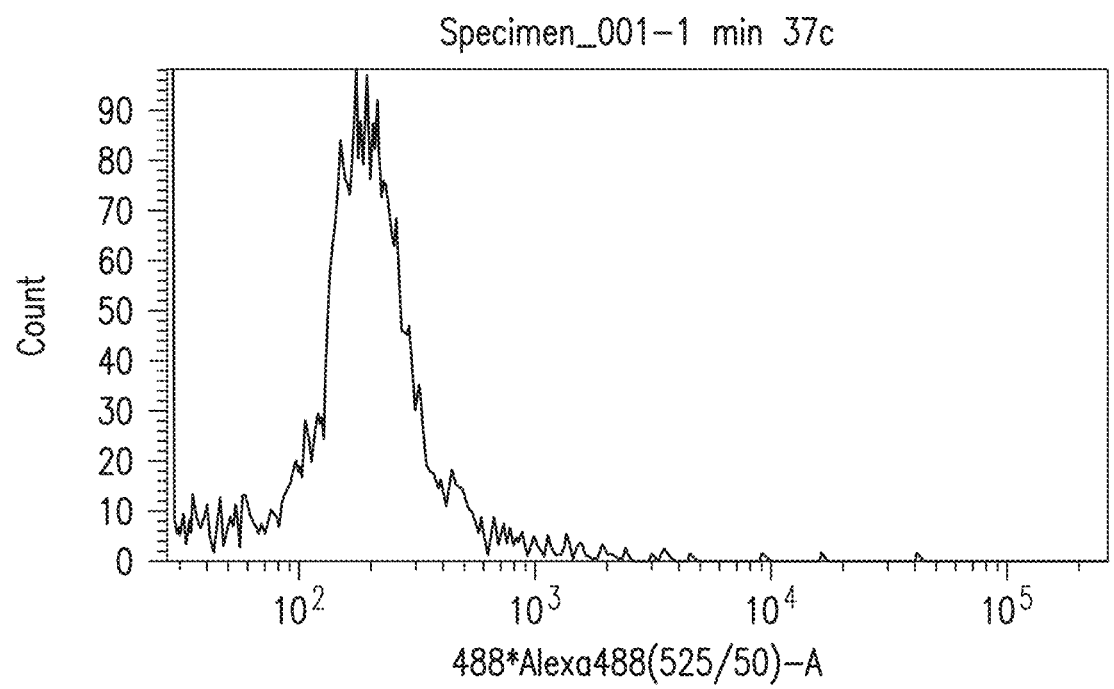
Figure 17D:
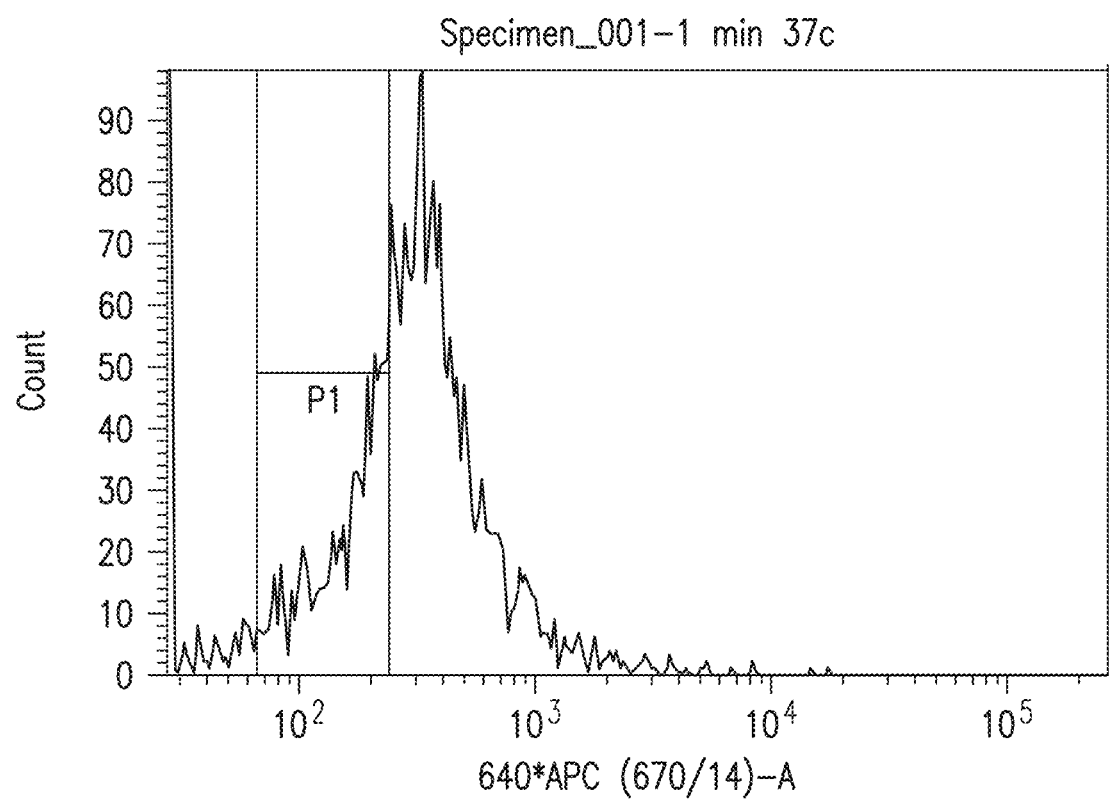
Figure 17E:
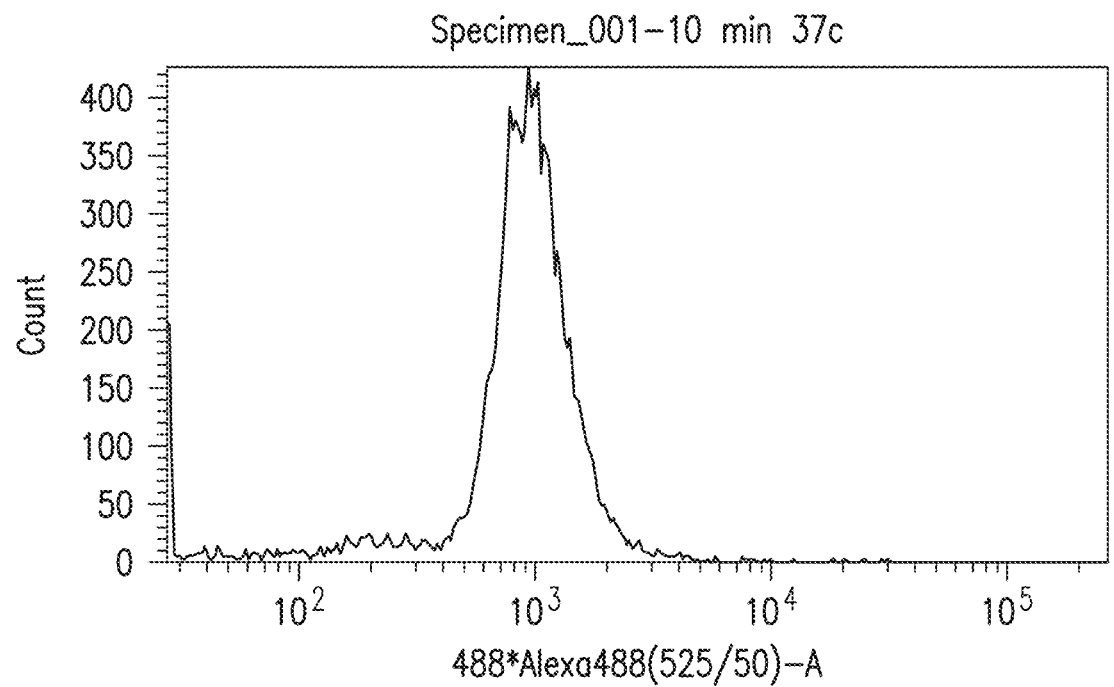
Figure 17F:
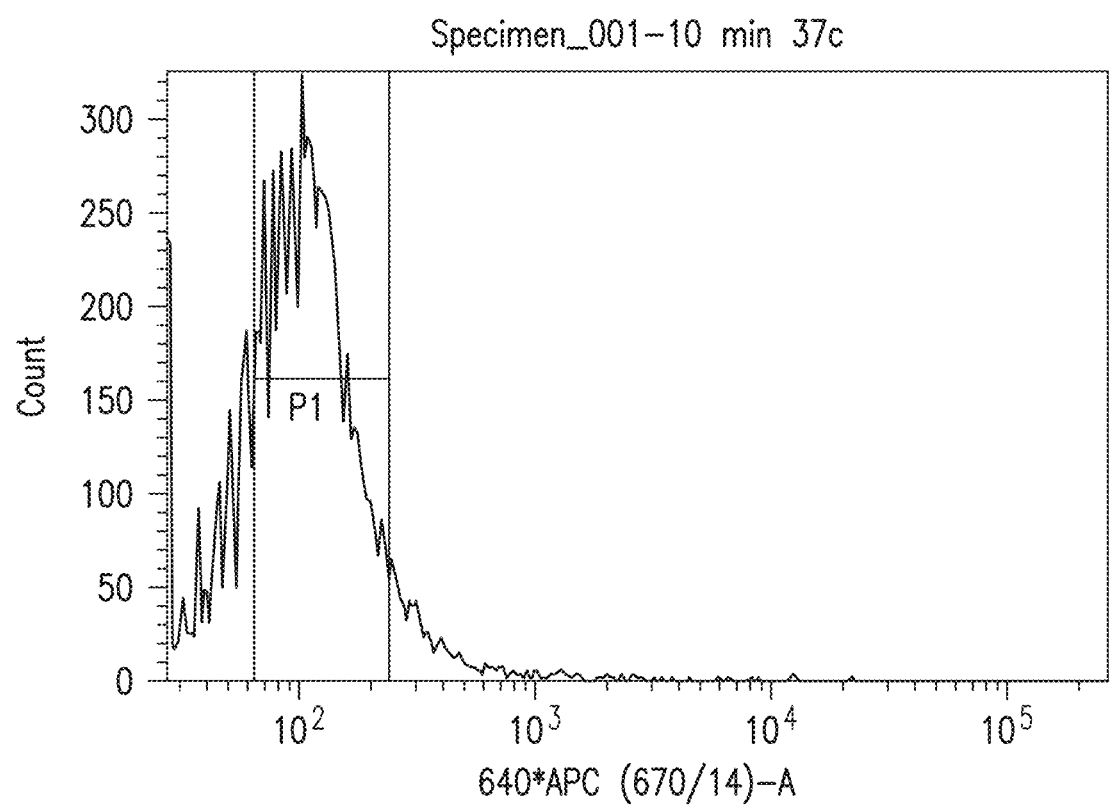

FIGS. 17A-17F show the results of flow cytometry readout of the internalization of AlexaFluor488-EGF/EGFR complex in A431 cells after stimulation. The prox-HCR assay was used to detect AlexaFluor488-EGF/EGFR at the cell membrane at 670 nm (Cy5) while the AlexaFluor488 was detected by itself. FIGS. 17A-17B: the flow cytometry data without stimulation. FIGS. 17C-17F show flow cytometry data with stimulation. Analysis of the flow cytometry data showed a small shift of fluorescence at 525 nm (AlexaFluor488) after stimulation with AlexaFluor488-EGF for 1 min at 37° C. (FIG. 17C) This shift increased after 10 min at 37° C. (FIG. 17E). In contrast we could see an increase of the Cy5 fluorescence after 1 min at 37° C. (FIG. 17D), which could not be observed after 10 min anymore (FIG. 17F). Neither, fluorescence at 525 nm nor at 670 nm changed considerably after 30 min of incubation with AlexaFluor488-EGF (data not shown).

EXAMPLE 1—IN SILICO ANALYSIS OF THE OLIGONUCLEOTIDE SYSTEM

An oligonucleotide system for proximity-dependent HCR (prox-HCR) was designed and carefully fine-tuned. Hairpins were designed for use as the nucleic acid domains of proximity probes (proximity hairpins).

The proximity hairpins were designed to be stable enough that they do not open spontaneously, whilst still being able to open once proximity binding has occurred to achieve good performance of the method. Therefore in this design the proximity hairpins did not contain sticky ends, a feature which is intrinsic to a regular HCR system, and we also considered and balanced length of the stems and loops of the hairpins, as well as the C/G ratio of the stems. A total of five oligonucleotides were designed for this method (see Table 1).

TABLE 1

Proximity HCR oligonucleotide system.

| | |
|---|---|
| Activator (SEQ ID NO: 1) | GACTCGCATTCACTGAATACAGC GGGCCTTCATGTTACAGACGA |
| Proximity hairpin 1 (SEQ ID NO: 2) | TCGTCTGTAACATGAAGGCCCGC TGTATTCAGTGAATGCGAGTCAG ACGAATACAGCGGGCCTTCATGT TACAGACGA |
| Proximity hairpin 2 (SEQ ID NO: 3) | CTGGGAGTCGTCTGTAACATGAA GGCCCGCTGTATTCGTCTTACTT CATGTTACAGACGACTCCCAG |
| HCR Hairpin 1 (SEQ ID NO: 4) | Fluorophore-ACAGACGACTC CCAGTACCTTCAGCTGGGAGTCG TCTGTAACATGAAGTA |
| HCR Hairpin 2 (SEQ ID NO: 5) | CTGAAGGTACTGGGAGTCGTCTG TTACTTCATGTTACAGACGACTC CCAG-Fluorophore |

Figure 1:
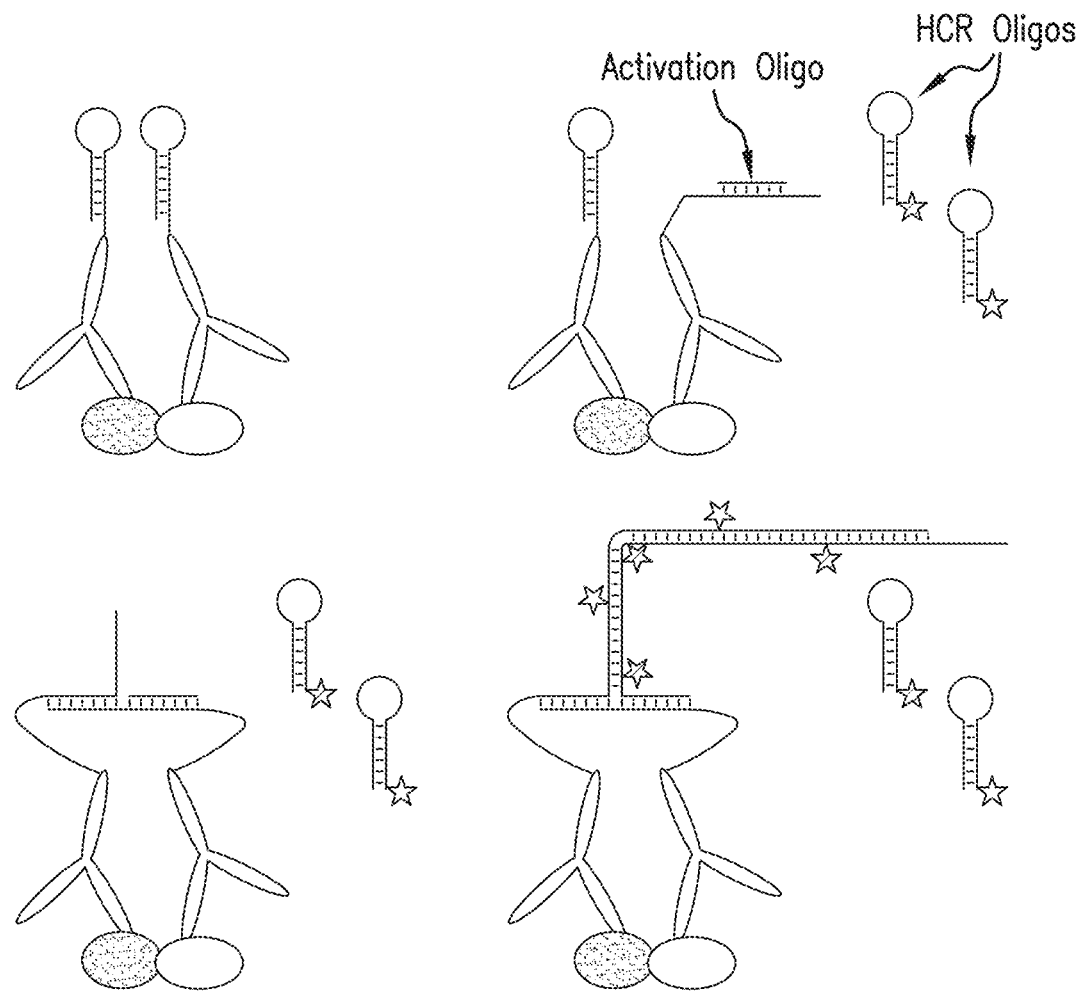
Figure 2A:
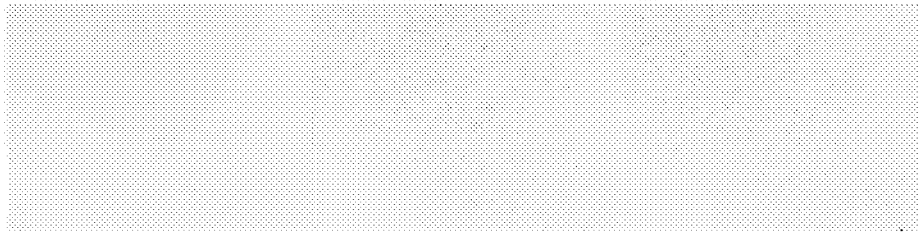
FIGS. 2A-2D show a proof-of-principle experiment, performed with biotinylated proximity hairpins on streptavidin-coated beads. This shows that HCR can proceed using 5 nM HCR oligonucleotides, and shows that at room temperature and at 37° C. addition of the activator oligonucleotide is essential for HCR to proceed.
Figure 2B:
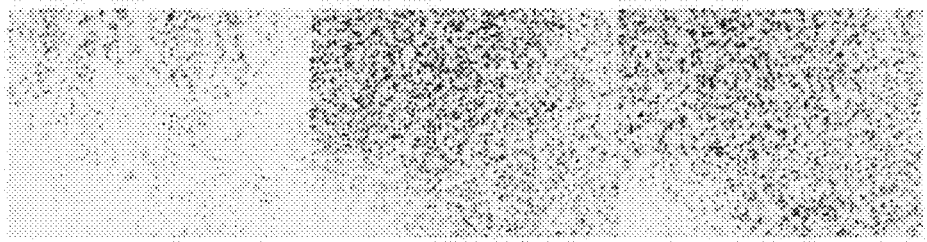
Figure 2C:
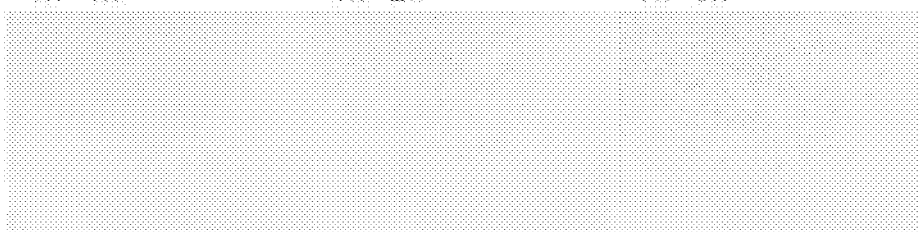
Figure 2D:
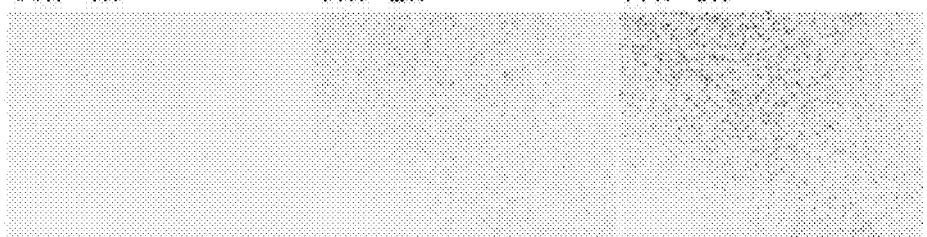
Figure 3A:
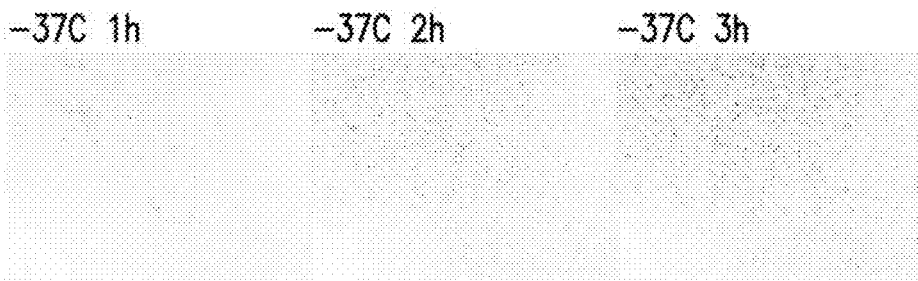
FIGS. 3A-3D show the same experimental procedure as in FIG. 2, but performed with 50 nM HCR oligonucleotides.
Figure 3B:
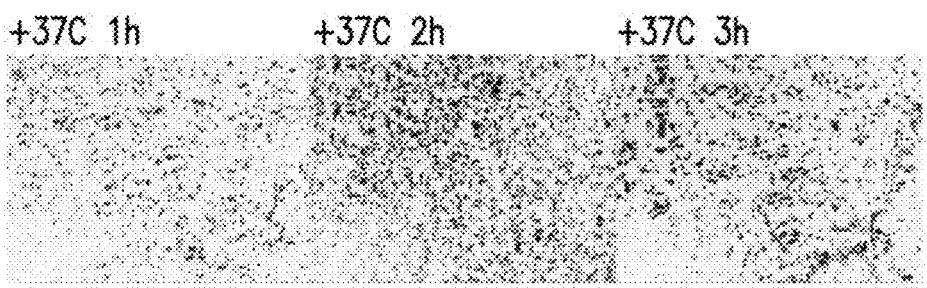
Figure 3C:
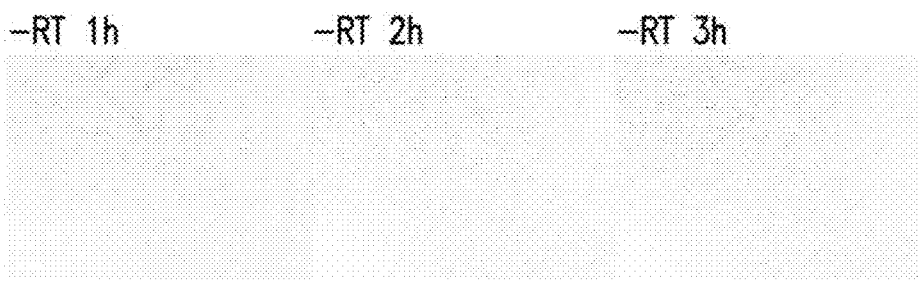
Figure 3D:
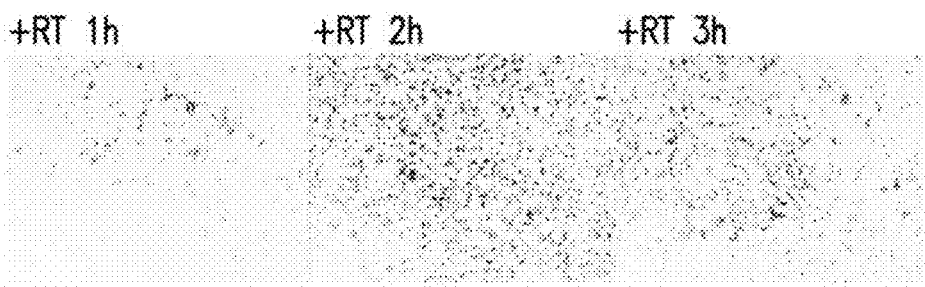

All oligonucleotides were first constructed in silico with NUPACK (www.nupack.org). The oligonucleotide system was designed in a way that an Initiator oligonucleotide ("activator") would invade the hairpin structure of the first proximity-hairpin, which upon proximity could invade the second proximity-hairpin. Both proximity-hairpins were designed to be kinetically trapped in their hairpin structure in the absence of an initiator oligonucleotide. The 3' end of the second proximity-hairpin in its opened form can invade HCR hairpin 1, the first of the two HCR-amplification oligonucleotides (HCR monomers). By invading each other the two HCR-hairpins will build up a fluorescently labelled detection molecule, in essence a nicked and fluorescently labelled double stranded DNA. Similarly to the proximity-hairpins the HCR hairpins are designed to be trapped in their hairpin structure in the absence of the initiating proximity-hairpin, thus avoiding self-initiation of the reaction (see FIG. 1).

A 44 nt Initiator oligonucleotide was designed. The first proximity hairpin was designed to contain a 30 bp hairpin and an 18 nt loop, whilst the second proximity hairpin contained a 24 bp hairpin and a 19 nt loop. The Gibbs free energy of the two hairpins is −144 kJ/mol and −105 kJ/mol respectively. Both HCR hairpins (HCR monomers) have similar structures (15 bp stem, 9 nt loop, 11 nt sticky end for HCR hairpin 1, and 15 bp stem, 11 nt loop, 9 nt sticky end for HCR hairpin 2), and had similar Gibbs free energy values (−70 kJ/mol and −75 kJ/mol respectively). All Energy calculations were performed at 37° C. in PBS supplemented with 10 mM $MgCl_2$ using NUPACK.

EXAMPLE 2—IN SOLUTION EXPERIMENTS

An assay was developed to demonstrate that the above method could be used to generate an HCR product, and to optimise the reaction conditions required for initiation and elongation to maximise the signal/noise ratio.

Biotinylated first and second proximity hairpins were mixed and conjugated to streptavidin-coated beads (Dynabeads MyOne, Invitrogen) by incubating for 30 minutes at room-temperature (RT) in reaction buffer (PBS+10 mM $MgCl_2$). After washing twice, the beads were incubated with 5 nM Initiator oligonucleotide for 15 minutes at 37° C. (+) or left in reaction buffer (−). After two further washing steps, each sample of beads was split and incubated with either 5 nM or 50 nM HCR oligonucleotides, and at either 37° C. or RT. Samples were taken after 1 hour, 2 hours and 3 hours, and after washing were immobilised on a poly prep slide to visualise the signal.

A Zeiss Axioplan 2 imaging microscope equipped with filters optimised for Texas Red and DAPI was used for image acquisition, using a 20× (0.8 NA) and a 40× (1.3 NA) objective and a Zeizz AxioCam Mrm camera. Exposure times were kept equivalent for all samples within each experiment. For all datasets the sites for acquisition were chosen randomly.

A measurement of fluorescence in images was performed using CellProfiler 2.1.0. Fluorescent beads were identified as primary objects, and a median intensity value for all pixels of the identified object was calculated and translated into a fluorescent units (FU) value (i.e. a normalisation of the intensity values recorded at 8 bit to a scale from 0 to 1). All statistical analysis was carried out using SPSS 22 (IBM; Release 22.0.0.0).

Figure 4:
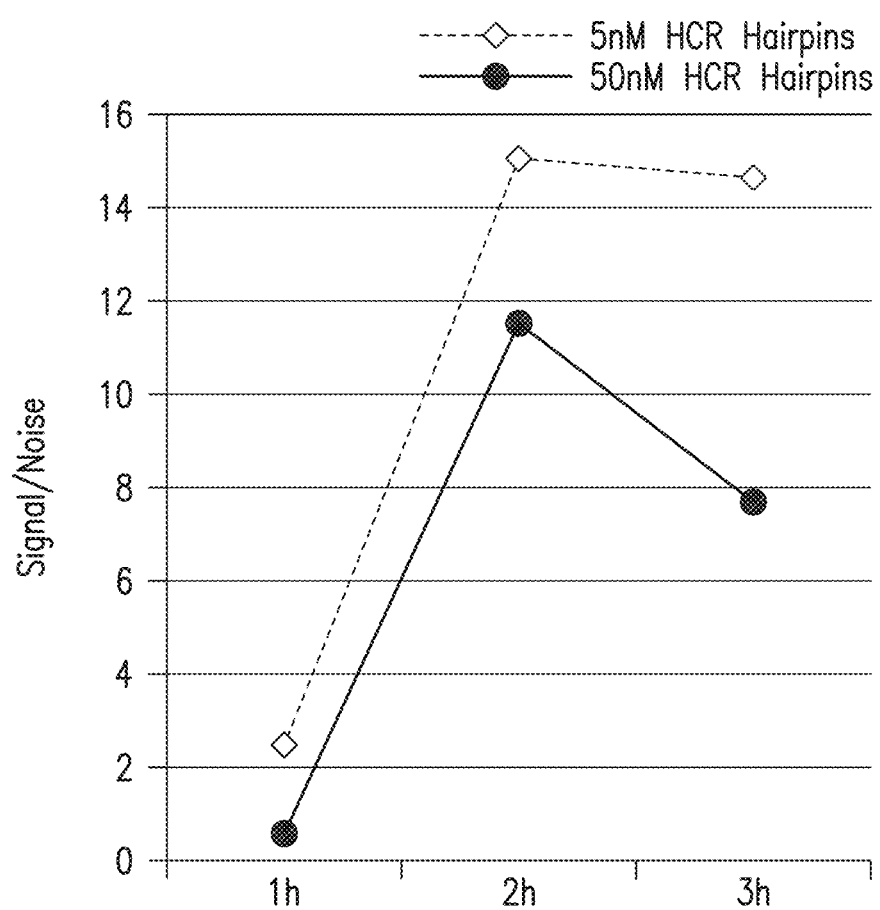
FIG. 4 shows the signal/noise ratios calculated at each of the time points in FIGS. 2 and 3.

A fluorescent signal was generated where beads were incubated in the presence of the Initiator Oligonucleotide, but not in the (−) samples (see FIGS. 2 and 3). Overall fluorescence was found to be higher and more robust at 37° C. than at room temperature (1.00 FU vs 0.32 FU for 50 nM, and 0.53 FU vs 0.08 FU for 5 nM after 2 hours of incubation) (see FIG. 2 D vs B and FIG. 3 D vs B). At 37° C. fluorescence peaked after 2 hours and did not increase further. Signal/noise ratios (defined by the ratio between samples with (+) and without (−) Initiator peaked at 2 hours (11.5 for 50 nM vs 15.1 for 5 nM) (see FIG. 4).

EXAMPLE 3—LONG-TERM STABILITY OF THE HCR CONSTRUCT

The long-term stability of the HCR product formed in the above assay was assessed by measuring the fluorescence intensity, and signal/noise ratio of the above reaction over time.

The biotinylated proximity hairpins were conjugated to the beads as outlined in Example 2. After washing away the residual unbound oligonucleotides, the beads were incubated with 5 nM Initiator oligonucleotide for 15 minutes at 37° C. (+) or left in reaction buffer (−). After two further washing steps, the beads were incubated with 5 nM HCR oligonucleotides in reaction buffer for 2, 5 and 24 hours at 37° C. Visualisation was performed as outlined in Example 2.

Testing showed that the four different hairpin species of Example 1 were stable for at least five hours. The fluorescent signal generated in the proximity HCR reaction remained for the duration of the experiment, but after 24 hours a low level of fluorescence was detectable in the (−) samples (see FIG. 5A), indicating a low level of non-specific formation of the HCR product. The fluorescent signal was found to increase over time, up to the end of the 24 hour period. However non-specific fluorescence in the (−) samples was also found to be highest after 24 hours (see FIG. 5B).

EXAMPLE 4—EFFECT OF IONIC STRENGTH AND SALT CONCENTRATION

The above assay was performed in different buffers to determine the effect of ionic strength on the assay. 2×SSC buffer, 1×PBS supplemented with 10 mM $MgCl_2$, 1×PBS supplemented with 10 mM $MgCl_2$ containing 20% formamide, and 50 mM $Na_2HPO_4$ supplemented with 1M NaCl were used.

5 nM biotinylated first and second proximity probes were incubated with streptavin-coated beads for 30 minutes at RT in each of the respective buffers. After washing twice, the beads were incubated with 5 nM Initiator oligonucleotide for 15 minutes at 37° C. (+) or left in reaction buffer (−). After two further washing steps, each sample of beads was split and incubated with 5 nM HCR oligonucleotides in their respective buffer at 37° C. After 2 hours, samples were washed twice and immobilised on a poly prep slide to visualise the signal.

Median fluorescence increased from 0.009 FU for 2×SSC buffer to 0.011 FU for 1×PBS supplemented with 10 mM $MgCl_2$ (p=0.035 [Oneway Anova with Bonferroni post hoc test]) and to 0.014 FU for 50 mM $Na_2HPO_4$+1M NaCl ($p<0.001$ [Oneway Anova with Bonferroni post hoc test]). The signal/noise ratios follow the monovalent ionic strengths of the buffers (1×PBS+10 mM $MgCl_2$:1.12; 2×SSC: 1.20; 50 mM $Na_2HPO_4$+1 M NaCl: 1.63) (see FIG. 6). Addition of formamide increased the median fluorescence signal in 1×PBS+10 mM $MgCl_2$ significantly (from 0.011 FU to 0.018 FU; p<0.001 [Oneway Anova with Bonferroni post hoc test]), leading to a signal/noise ratio of 2.124 which was not significantly different from 50 mM $Na_2HPO_4$+1 M NaCl (p=1.000 [Oneway Anova with Bonferroni post hoc test]), however signal/noise was significantly different from 1×PBS+10 mM $MgCl_2$ (p, 0.001 [Oneway Anova with Bonferroni post hoc test]).

EXAMPLE 5—SOLID-PHASE EXPERIMENT

The ability of the above reaction to detect molecules immobilised on a solid-phase surface was assessed by immobilising streptavidin on a slide, and detecting it using biotinylated proximity hairpins.

5 nM of biotinylated proximity hairpins were incubated on streptavidin-coated slides for 30 minutes at 37° C. Residual oligonucleotides were washed away with reaction buffer. Slides were incubated with Initiator oligonucleotide for 15 minutes at 37° C. (+) or left in reaction buffer (−). Upon washing, the slides were incubated with 5, 10, 20 or 50 nM HCR oligonucleotides for 2 hours at 37° C. Slides were washed again, dried in ethanol and mounted.

After 2 hours the slides were visualised and overall fluorescence was assessed for each concentration of HCR oligonucleotides (see FIG. 7A). Although a signal was detectable at each concentration of HCR oligonucleotides, higher concentrations lead to higher levels of fluorescence. A signal was detectable in the (−) samples for 50 nM oligonucleotides, indicating a low level of non-specific formation of the HCR product.

EXAMPLE 6—DETECTION OF DRIED-IN PRIMARY ANTIBODY

An assay was developed to assess whether antibody-conjugated proximity probes could be used to detect an analyte in an in-situ context. A rabbit antibody was immobilised on microscopy slides and detected using first and second proximity probes conjugated to anti-rabbit IgG.

Proximity hairpin oligonucleotides were covalently conjugated to IgG molecules. Antibody was activated using SANH for 2 hours at room temperature. Excess SANH was removed using a Zeba desalting column. Aldehyde-modified proximity hairpin was added in a threefold excess using 10 mM aniline as a catalyst, and incubated for 2 hours at room temperature before successfully conjugated proximity probes were purified by HPLC.

A 1:100 dilution of rabbit anti-HIF1 was incubated on SuperFrost slides at 37° C. overnight in a dry environment and residual antibody was washed away with PBS. Donkey anti-rabbit antibodies conjugated to first and second proximity probes were incubated on the slide for 1 hour at 37° C.; slides were incubated with Initiator oligonucleotide (+) or left in reaction buffer (−). Upon washing, the slides were incubated with 10 nM HCR oligonucleotides for 2 hours at 37° C. Slides were washed again, dried in ethanol and mounted.

In a further experiment, mouse antibody was immobilised on the slides and the detection procedure was repeated. Slides were prepared as above to estimate the non-specific binding of the HCR probes.

A fluorescent signal was generated in samples where the first and second proximity probes were conjugated to anti-rabbit IgG and incubated in the presence of the Initiator oligonucleotide. No signal was detected in the (−) samples (see FIG. 8A). No signal was detected in samples where a mouse antibody was immobilised on the slide, indicating that the proximity HCR system could detect specific analytes within a sample (see FIG. 8B).

EXAMPLE 7—IN-SITU EXPERIMENTS

The above method was adapted to test whether specific analytes (Histone H3, ribosomal protein L3a and hTert) within a cell sample could be detected via proximity HCR.

BjhTert cells were grown in Minimal Essential Medium (Gibco) supplemented with 10% v/v FCS, 2 mM glutamine and 100 U/ml Penicillin-Strepromycin. In a humidified incubator at 37° C. in a 5% $CO_2$ atmosphere. Cells were trypsinised prior to slide preparation, seeded into eight-well chamber slides (Lab-Tek, Nunc) and left to attach for 48 hours prior to preparation of microscopy slides. Medium was aspirated and cells were washed prior to fixation in 3.7% formaldehyde on ice for 30 minutes. After washing residual formaldehyde slides were dried in 96% EtOH and stored at −20° C. for further use.

BjhTert cells fixed on microscopy slides were rehydrated in PBS and permeabilised with 0.1% TritonX for 5 minutes. Cells were blocked for 30 minutes at 37° C. Cells were incubated with primary antibodies (rabbit anti-histone H3, ribosomal protein L3a and hTert respectively) overnight at 4° C. Upon washing twice with PBS at room temperature for 2 minutes, slides were incubated with the first and second proximity probes conjugated to anti-rabbig IgG for 1 hour at 37° C., as above. After two further washes, slides were incubated with 10 nM Initiator oligonucleotide for 30 minutes (+) or left in reaction buffer (−). After a quick wash, the cells were incubated with 20 nM HCR oligonucleotides for 2 hours at 37° C. in reaction buffer. Slides were washed twice with reaction buffer before nuclei were stained with Hoechst and slides were mounted with SlowFade. Cells were imaged as in Example 2, and 4 z-levels with 480 nm in between were acquired.

Histone H3, ribosomal protein L3a and hTert were each detected using the above-method (see FIG. 9 A-C). The right hand column shows the signal arising from the proximity HCR reaction, while the left hand column shows merged pictures with the DAPI channel. Upper panels in each section show the reaction without the Initiator oligonucleotide (−), while lower panels show the reaction with the Initiator oligonucleotide (+).

EXAMPLE 8—IN-SITU PROXIMITY-HCR

The above method was further adapted in order to assess whether proximity-HCR was capable of detecting a specific protein-protein interaction (PPI) in an in-situ setting. The interaction between HIF-1α and HIF-1b was chosen as a model system. Whilst HIF-1b/ARNT is constitutively expressed in DLD1 cells, the expression of HIF-1α, and thus the formation of the HIF-1α/HIF-1b complex, is inducible by $CoCl_2$.

DLD1 cells were grown in McCoy's 5a (Modified) Medium (Gibco) supplemented with 10% v/v FCS, 2 mM glutamine and 100 U/ml Penicillin-Strepromycin as above. Cells were seeded at a density of $6 \times 10^4$ cells/$cm^2$ into eight-well chamber slides and left to attach for 24 hours. HIF-1α expression was induced by treating cells with 150 µM $CoCl_2$ (Sigma-Aldrich) dissolved in PBS for 4 hours before cells were washed and fixed as described above.

DLD1 cells were rehydrated and permeabilised as above. Cells were blocked with DuoLink (Olink) for 1 hour at 37° C. Cells were incubated with mouse anti-HIF-1α (Abcam) and rabbit anti-HIF-1b (Santa Cruz Biotechnology Inc.) overnight at 4° C. Upon washing twice with TBS-0.05% TWEEN®-20 (polysorbate 20), cells were blocked for an additional 15 minutes and incubated with proximity probes conjugated to rabbit and mouse IgG for 1 hour at 37° C. Initiation and amplification of the HCR product and imaging of the cells was performed as above.

The HIF-1α/HIF-1b complex can be detected using the proximity HCR assay (see FIG. 10). The left side of the picture shows the image acquired after the cells had been treated with CoCl2, inducing the expression of HIF-1α. The interaction between HIF-1α and HIF-1b is visualised with a strong signal, while on the right side, in the absence of CoCl2 (i.e. no HIF-1α is expressed), no signal is observed—only the signal from the DAPI channel was detectable.

EXAMPLE 9—ALTERNATIVE OLIGONUCLEOTIDE DESIGNS

Four further oligonucleotide sets for proximity-dependent HCR (prox-HCR) were designed as in Example 1 (see Tables 2-5). An oligo-A linker sequence was designed for the two proximity hairpin sequences (SEQ ID NOs: 6 and 7). An alternative, shorter activator sequence was designed (SEQ ID NO:8). An oligonucleotide set with mismatches between the activator oligonucleotide (SEQ ID NO:11) and the second region of complementarity in PH2 (SEQ ID NO:7) (and thus between the first region of complementarity in PH1 (SEQ ID NO:12) and the second region of complementarity in PH2) was also designed (Tables 4 and 5). A shorter activator sequence was also designed for use in this system (SEQ ID NO:13). Mismatches are shown in bold in Tables 4 and 5.

TABLE 2

Proximity HCR oligonucleotide system—no mismatch, long activator, oligo-A

| | |
|---|---|
| Activator (SEQ ID NO: 1) | GACTCGCATTCACTGAATACAGC GGGCCTTCATGTTACAGACGA |
| Proximity-hairpin 1 (SEQ ID NO: 6) | AAAAATCGTCTGTAACATGAAGG CCCGCTGTATTCAGTGAATGCGA GTCAGACGAATACAGCGGGCCTT CATGTTACAGACGA |
| Proximity-hairpin 2 (SEQ ID NO: 7) | AAAAAGTGGGAGTCGTCTGTAAC ATGAAGGCCCGCTGTATTCGTCT TACTTCATGTTACAGACGACTCC CAC |
| HCR hairpin 1 (SEQ ID NO: 8) | Fluorophore-ACAGACGACTC CCACATTCTCCAGGTGGGAGTCG TCTGTAACATGAAGTA |
| HCR hairpin 2 (SEQ ID NO: 9) | CTGGAGAATGTGGGAGTCGTCTG TTACTTCATGTTACAGACGACTC CCAC-Fluorophore |

TABLE 3

Proximity HCR oligonucleotide system—no mismatch, short activator, oligo-A

| | |
|---|---|
| Activator SEQ ID NO: 10) | GACTCGCATTCACTGAATACAGC GGGCCTTCATGTTAC |
| Proximity hairpin 1 (SEQ ID NO: 6) | AAAAATCGTCTGTAACATGAAGG CCCGCTGTATTCAGTGAATGCGA GTCAGACGAATACAGCGGGCCTT CATGTTACAGACGA |
| Proximity hairpin 2 (SEQ ID NO: 7) | AAAAAGTGGGAGTCGTCTGTAAC ATGAAGGCCCGCTGTATTCGTCTT ACTTCATGTTACAGACGACTCCC AC |
| HCR Hairpin 1 (SEQ ID NO: 8) | Fluorophore-ACAGACGACTC CCACATTCTCCAGGTGGGAGTCG TCTGTAACATGAAGTA |
| HCR Hairpin 2 (SEQ ID NO: 9) | CTGGAGAATGTGGGAGTCGTCTG TTACTTCATGTTACAGACGACTC CCAC-Fluorophore |

TABLE 4

Proximity HCR oligonucleotide system—mismatch, long activator, oligo-A.

| | |
|---|---|
| Activator (SEQ ID NO: 11) | GACTCGCATTCACTGAATACAGC GGGCCTTCATGCCACAGACGA |
| Proximity hairpin 1 (SEQ ID NO: 12) | AAAAATCGTCTGTGGCATGAAGG CCCGCTGTATTCAGTGAATGCGA GTCAGACGAATACAGCGGGCCTT CATGCCACAGACGA |
| Proximity hairpin 2 (SEQ ID NO: 7) | AAAAAGTGGGAGTCGTCTGTAAC ATGAAGGCCCGCTGTATTCGTCT TACTTCATGTTACAGACGACTCC CAC |
| HCR Hairpin 1 (SEQ ID NO: 8) | Fluorophore-ACAGACGACTC CCACATTCTCCAGGTGGGAGTCG TCTGTAACATGAAGTA |
| HCR Hairpin 2 (SEQ ID NO: 9) | CTGGAGAATGTGGGAGTCGTCTG TTACTTCATGTTACAGACGACTC CCAC-Fluorophore |

TABLE 5

Proximity HCR oligonucleotide system—mismatch, short activator, oligo-A.

| | |
|---|---|
| Activator (SEQ ID NO: 13) | GACTCGCATTCACTGAATACAGC GGGCCTTCATGCCAC |
| Proximity-hairpin 1 (SEQ ID NO: 12) | AAAAATCGTCTGTGGCATGAAGG CCCGCTGTATTCAGTGAATGCGA GTCAGACGAATACAGCGGGCCTT CATGCCACAGACGA |
| Proximity-hairpin 2 (SEQ ID NO: 7) | AAAAAGTGGGAGTCGTCTGTAAC ATGAAGGCCCGCTGTATTCGTCT TACTTCATGTTACAGAGACTCCC AC |
| HCR hairpin 1 (SEQ ID NO: 8) | Fluorophore-ACAGACGACTC CCACATTCTCCAGGTGGGAGTGT CTGTAACATGAAGTA |
| HCR hairpin 2 (SEQ ID NO: 9) | CTGGAGAATGTGGGAGTCGTCTG TTACTTCATGTTACAGACGACTC CCAC-Fluorophore |

NUPACK simulations indicate that reducing the length of the initiator oligonucleotide by 6 nt should not impact signal generation, whilst significantly reducing the hybridisation of the activator oligonucleotide to PH2. This was also found when a mismatch was introduced into the system.

The mismatch decreases the hybridisation efficiency between PH1 and PH2, but is intended to suppress hybridisation of the activator oligonucleotide to PH2. NUPACK analysis suggests that non-specific activation is reduced.

The effect of the mismatch on non-specific activation was tested using a bead-based assay. PH2 corresponding to SEQ ID NO:7 was immobilised on a bead. After incubation with the activator oligonucleotides (either without the mismatch (SEQ ID NO:1) or with the mismatch (SEQ ID NO:11)), the HCR reaction was carried out using 100 nM HCR monomers. As this assay was performed in the absence of a PH1 oligonucleotide, any activation represents non-specific activation by the activator oligonucleotide. Where there was a mismatch between the activator oligonucleotide and the second region of complementarity in PH2, the degree of non-specific activation was significantly lower than where there was no mismatch (compare FIG. 11 parts (B) (mismatch) and (A) (no mismatch)).

EXAMPLE 10—FURTHER DEVELOPMENTS USING PROX-HCR

Results

In the following experiments, the oligonucleotides shown in Table 4 are used.

The prox-HCR system requires four hairpin species and an activator instead of just two hairpin species. Two proximity probes bind to a target analyte (FIG. 12 A). In the first step of our design an activator oligonucleotide needs to invade the first proximity-hairpin (PH1) (FIG. 12 B). The liberated first proximity-hairpin will invade the second proximity-hairpin (PH2) (FIG. 12 C), thereby liberating the initiator sequence for HCR amplification. HCR amplification occurs by alternate binding of HCR monomers 1 and 2 (FIGS. 12 D-12L).

The two proximity probes comprise nucleic acid domains (with metastable secondary structures—hairpins). The hairpins comprise long stems (30 bp and 24 bp for PH1 and PH2 respectively) and relatively big loops (18 nt and 19 nt for the two proximity hairpins respectively (FIG. 13 A-B)). The negative free Gibbs energy (-ΔG) for both secondary structures is estimated to be quite high (39.51 kcal mol$^{-1}$ and 27.35 kcal mol$^{-1}$ at 37° C. in 1M NaCl). The HCR hairpins have similar structures to commonly used HCR oligonucleotides, namely a short sticky end (9 nt 5' for H1 and 11 nt 3' for H2), the stem is 15 bp for both oligonucleotides and the loops consist of 11 nt for H1 and 9 nt for H2 (FIG. 13 C-D).

Optimization of Experimental Parameters

The first round of experiments was performed using surface plasmon resonance in order to test the kinetic properties of the oligonucleotide system.

The experiments showed an efficient binding of the activator oligonucleotide to immobilized PH1 (FIG. 14 A) in a gradient of concentrations. Furthermore the subsequent binding of the opened PH1 to the PH2 also occurs efficiently without any measurable dissociation (FIG. 14 B). Due to inherent properties of prox-HCR the sensorgrams could not be fitted to obtain quantitative data for association or dissociation constants.

A 'fishing rod' sequence, (an identical to the HCR initiator region that sticks out of the activator-PH1-PH2 complex and acts as an initiating oligonucleotide for the hybridization chain reaction) was immobilised and tested for binding to HCR monomer 1 (FIG. 14 C). The results showed fast association of H1 with the fishing rod while again almost no dissociation could be observed. The subsequent binding of the opened H1 to the H2 also occurs efficiently without any measurable dissociation (FIG. 14 D). Both reactions could not be fitted so that no quantitative data could be obtained.

Our data furthermore showed no visible association between PH2 alone and H1 or H2. Also the PH1-activator complex alone did not react with H1 or H2 (data not shown).

To further characterize the behavior of the amplification reaction we used an Opera High Content Screening System to determine the buildup of fluorescence on beads during short reaction times. Our data showed a robust increase in fluorescence after only 30 min of incubation at 37° C. Even as early as 5 min incubation time was enough to see a dose-dependent (concentration of HCR oligonucleotides) increase in fluorescence (FIG. 15 A).

Based on these experiments and the kinetic calculations from the Biacore we decided to use a concentration of 50 nM for each of the HCR oligonucleotides for subsequent experiments on beads.

Using epifluorescent microscopes we could show that the reaction of 50 nM HCR oligonucleotides reached its maximum fluorescence after 30 min and did not increase with longer incubation time. Signal was already distinguishable from the negative control after the earliest time point (10 min) (FIG. 15 B). Furthermore the negative control did not generate a visible amount of signal over the whole time period. Images showing the development of a fluorescent signal are shown for illustrative purposes (FIG. 15 C).

In Situ Analysis of Protein Interactions Using Prox-HCR

The interaction between E-cadherin and β catenin in DLD1 cells and in colon tissue was used as a model system to show the feasibility of prox-HCR when compared to in situ PLA (FIG. 16).

The results show the same specific pattern of signal localization for prox-HCR (FIG. 16 A) and in situ PLA (FIG. 16 B) in cells. Similarly the application of prox-HCR in fresh frozen colon tissue showed comparable results to in situ PLA (FIG. 16 C-D). When looking at the actual number of generated signals it is clear that prox-HCR is more efficient than in situ PLA. On the other hand the signals that are generated in in situ PLA are a lot stronger than those produced by prox-HCR.

The specificity of the prox-HCR reaction can be evaluated in (FIG. 16 E-F). We visualized the phosphorylation of PDGFR-ß in untreated cells (FIG. 16 E) and BjhTert cells stimulated with 100 ng mL$^{-1}$ PDGF-BB (FIG. 16 F). Furthermore we detected the phosphorylation of Syk in HG3 cells (FIG. 16 G) and compared the results to a technical negative control (no primary antibodies) (FIG. 16 H). Both assays showed strong signal in the positive samples while fluorescence was low in the biological negative control and absent in the technical control.

Internalization of the EGF-EGFR Complex in Flow Cytometry

FIG. 17 shows the results of the flow cytometry read-out of the internalization of AlexaFluor488-EGF/EGFR complex in A431 cells after stimulation. The prox-HCR assay was used to detect the AlexaFluor488-EGF/EGFR complex at the cell surface at 670 nm (Cy5) while the AlexaFluor488 was detected by itself. Analysis of the flow cytometry data showed a small shift of fluorescence at 525 nm (AlexaFluor488) after stimulation with AlexaFluor488-EGF for 1 min at 37° C. compared to unstimulated cells (FIG. 17 A-B, left hand histogram). This shift increased after 10 min at 37° C. (FIG. 17 C, left hand histogram). In contrast we could see an increase of the Cy5 fluorescence after 1 min at 37° C. (FIG. 17 A-B, right hand histograms), which could not be observed after 10 min anymore (FIG. 17 C, right hand histogram). Neither, fluorescence at 525 nm nor at 670 nm changed considerably after 30 min of incubation with AlexaFluor488-EGF (data not shown).

Discussion

In this study we present a technique for detection of protein interactions and PTMs in an enzyme free assay based on HCR. We could show its feasibility for in situ reactions on slides as well as its use in flow cytometry.

Our prox-HCR oligonucleotide system underwent several optimization steps in order to yield a system that shows a reasonably fast amplification rate without generating false positive signal. One of the features included is a two base mismatch between PH1 and PH2. This mismatch decreases the stability of the PH1-PH2 complex, which in turn makes the system less efficient. However the mismatch reduces the ability of the activator oligonucleotide to bind to PH2 and to prevent the H1 and H2 from binding to the I-PH1 complex, both of which might lead to unspecific signal.

Upon comparison of our method with classical HCR one of the major differences in the oligonucleotide system is the different stem/loop lengths. Dirks and Pierce propose in their initial paper a 18 bp stem and 6 nt loop system (Dirks, R. M. and Pierce, N. A. 2004. PNAS 101, 15275-15278), which differs from our system utilizing 15 bp/9 nt and 15 bp/11 nt for the HCR hairpins, and 24 bp/18 nt and 29 bp/18 nt for the proximity-hairpins. When evaluating the stem to loop ratios we can see considerable differences between the two systems (regular HCR: 3 versus prox-HCR: 1.4 and 1.7).

Dirks and Pierce tested a series of hairpins with different stem to loop ratios. All their hairpin variations were either unstable or too slow in starting the reaction. The system we present however is stable for a long time and provides a reasonable amplification rate.

This amplification rate could however not be quantitatively determined. Our Biacore data could not be fitted, probably because of a conformational change when the displaced part is liberated. However we could estimate the association constants to be in the region of $10^6$ $M^{-1}s^{-1}$ and the dissociation constants to be in the region of $10^{-16}$ $s^{-1}$. Even though we cannot provide exact values we can conclude that the amplification reaction occurs at a reasonable speed and that no visible dissociation occurs. This is also in accordance with the experiments we conducted on magnetic beads. Because of the lack of return reaction we can assume that the amplification commences until one or both of the HCR oligonucleotides are exhausted which is a hallmark for hybridization chain reaction.

The gold standard for visualizing protein interactions in situ right now is the proximity ligation assay (Soderberg, O. et al. 2006. Nature methods 3, 995-1000). In in situ PLA two oligonucleotides are hybridized to two proximity probes and then ligated to form a circle. This circle is then amplified in a process called rolling circle amplification to form a sub µm structure called rolling circle product (RCP). The RCPs can be visualized by hybridizing fluorophore-coupled detection oligonucleotides. In this way in situ PLA generates bright and big signals than can be digitally quantified which together with its high specificity and sensitivity is one of the main advantages of PLA. On the other hand, since PLA relies heavily on enzymatic steps (i.e. ligation and enzymatic polymerization) it is expensive to run. Also the possible generation of non-circular ligation products may be a reason for the low efficiency of in situ PLA.

Prox-HCR behaves similarly to in situ PLA when it comes to the localization of signal which speaks to specificity of the method compared with in situ PLA. Furthermore the biological negative control as well as the technical control show no or little generation of unspecific signal. When it comes to signal strength of the individual signals it becomes clear that the enzyme assisted amplification reaction of in situ PLA generates bigger and brighter signals while prox-HCR only creates very small dots of fluorescence. This is an advantage of the PLA technique because it allows for digital quantification of its results. However because of the higher efficiency of prox-HCR (a lot more fluorescent signals are generated) the signal produced resembles much more a uniform diffuse staining which still makes it possible to visualize the interaction.

In addition to cells and tissues fixed on slides we could show the feasibility of prox-HCR in FACS. Not only could we distinguish between stimulated and unstimulated cells via flow cytometry but also visualize the internalization of EGFR into the cell. In particular we could show that while the AlexaFluor488-EGF/EGFR complex is detectable on the cell surface after 1 min of stimulation it is not any more after 10 min. At the same time the AlexaFluor488 signal rises from 1 min to 10 min indicating that most of the AlexaFluor488-EGF/EGFR complex has been internalized after 10 min.

The independence from enzymatic steps while retaining the specificity of PLA is the greatest advantage of the prox-HCR method. This reduces costs of the assay considerably making the method better suited for high throughput screening of protein interactions. Furthermore it provides advantages by eliminating concerns of enzyme quality and storage. Maybe the largest impact of prox-HCR will be as a method in point of care devices. This is because the enzyme free environment of the assay has only little demands on storage (i.e. a device could be stored at room temperature for a long time) and handling (i.e. a device could completely be run at 37° C. without the need of cycling the temperatures). In addition to this prox-HCR is in theory amenable to other variations of HCR, such as the real time HCR for absolute quantification or the branched HCR amplification that might provide better signal to noise ratios due to its exponential signal growth. Furthermore the very nature of the proximity probes, i.e. the fact that they have secondary structures, makes them very sensitive to changes in oligonucleotide sequence. This hints to the idea that prox-HCR may be suitable to multiplex, which would be another advantage of the technique.

To conclude: We have herein described a method that combines dual recognition, for increased selectivity or detection of PPIs and PTMs, with a non-enzymatic process of generating a localized signal.

Methods

Design of the Oligonucleotide System

We first constructed all oligonucleotides in silico with NUPACK (www.nupack.org). We designed the oligonucleotide system in a way that an activator oligonucleotide would invade the hairpin structure of the first proximity-hairpin which upon proximity could invade the second proximity-hairpin. Regarding both proximity-hairpins, we designed them to be kinetically trapped in their hairpin structure in the absence of an activator oligonucleotide. The 3' end of the second proximity-hairpin in its opened form serves as a fishing rod and can invade the first of the two HCR-amplification oligonucleotides (HCR-hairpins H1 and H2). By invading each other H1 and H2 will build up a fluorescently labeled detection molecule, in essence nicked and fluorescently labelled double stranded DNA. Similarly to the proximity-hairpins the HCR-hairpins are designed to be trapped in their hairpin structure in the absence of the initiating proximity-hairpin, thus avoiding self-initiation of the reaction.

Cell Culture

Cells were grown in a humidified incubator at 37° C., 5% $CO_2$ atmosphere. BjhTert cells were grown in Gibco Minimum Essential Medium supplemented with 10% (v/v) fetal bovine serum, 2 mM glutamine, 100 U $mL^{-1}$ Penicillin-Streptomycin. For slide preparation, cells were trypsinized and seeded into eight-well chamber slides (Lab-Tek, Nunc), before being allowed to adhere for 48 h. At the second day the medium was exchanged for starvation medium (DMEM with 2 mM glutamine and 100 U $mL^{-1}$ Penicillin-Streptomycin) and cells were incubated for 24 h. For stimulation 100 ng $mL^{-1}$ PDGF-BB was added to the cells and cells were incubated for 5 min at 37° C. Medium was then aspirated and cells were fixed in 3.7% formaldehyde solution for 30 min on ice. After washing away residual formaldehyde the slides were dried in 96% Ethanol and stored at −20° C. until further use.

DLD1 cells were maintained in McCoy's 5A (Modified) Medium (Gibco) supplemented with 10% (v/v) fetal bovine serum, 2 mM glutamine, 100 U $mL^{-1}$ Penicillin-Streptomycin. For visualization of E-cadherin/ß-catenin interaction cells were seeded into eight-well chamber slides to reach near confluency after adherence. Cells were incubated for 24 h before aspirating the medium, washing with PBS and fixing for 30 min on ice with 3.7% formaldehyde solution. As described above, cells were dried and stored at −20° C. until further use.

HG3 cells were kept in RMPI 1640 medium supplemented with 10% (v/v) fetal bovine serum, 2 mM glutamine, 100 U mL$^{-1}$ Penicillin-Streptomycin. To prepare the slides cells were spun down (280 g for 10 min) and washed with PBS. 150,000 cells were transferred into each cell funnel in PBS and cytospins were created using the Cellspin 1 from Tharmac. Cells were fixed with 3.7% formaldehyde, washed and dried as described above. They were stored at −20° C. until further use.

A431 cells were grown in DMEM supplemented with 10% (v/v) FBS, 2 mM glutamine, 100 U mL$^{-1}$ Penicillin-Streptomycin, before being seeded into 6 well plates and left to adhere overnight. The next day cells were starved in starvation medium as described for BjhTert cells above. For flow cytometry analysis cells were detached using accutase (Sigma) at 37° C. for 10 min. Cells were washed twice with PBSB (1×PBS supplemented with 0.5% BSA) and stimulated with 40 ng mL$^{-1}$ AlexaFluor488-EGF for 1 min, 10 min and 30 min at 37° C. The reaction was stopped by adding 1% formaldehyde solution. Cells were washed and subsequently fixed with 1% formaldehyde solution for 10 min on ice. Residual formaldehyde was washed away after which cells were immediately used for prox-HCR.

Conjugation of Antibodies—Generation of Proximity Probes

Conjugation of the secondary antibodies was performed as previously described (Jarvius, M. et al. 2007. Molecular & cellular proteomics 6, 1500-1509). Briefly, anti-rabbit and anti-mouse antibodies were activated (catalog number: 711-005-152 and 715-005-150 respectively, Jackson ImmunoResearch Laboratories, West Grove, Pa.) with SANH (VWR) for 2 h at room temperature (RT). SANH was removed using Zeba desalting column (Thermo Scientific) and each batch was mixed separately with one of the aldehyde modified proximity-hairpins in a threefold excess. Proximity hairpins they were heated up to 95° C. for 2 min prior to addition in order to destroy any quaternary structures that may have formed. Using 10 mM aniline as a catalyst, the reaction was left at RT for an additional 2 h, before the generated proximity-probes were purified by high pressure liquid chromatography. All conjugates were verified on a SDS gel.

Solid Phase Experiments

Hybridization Kinetics Using Surface Plasmon Resonance Experiments

All experiments were performed using Biacore 2000 or Biacore S51 instruments. All buffers used in experiments were 0.22 µm filtered and degassed. To start with streptavidin was immobilised on CM5 sensor-chips via amine coupling with a immobilization level of 1000-1500 RU. One flow cell on each sensor-chip was activated and deactivated without protein immobilization as a reference. The streptavidin-coated surface was preconditioned with pulse injections of 50 mM NaOH, 1M NaCl to establish a stable baseline. In order to analyze the different interactions, 150-200 or 50-100 RU of biotinylated oligonucleotides (fishing rod, PH1 or PH2) were captured onto the streptavidin coated surface. We performed all kinetic assays at 37° C. in HCR buffer (50 mM Na$_2$HPO$_4$, 1M NaCl, pH=7.4) supplemented with 0.05% (v/v) TWEEN®-20 (polysorbate 20). After immobilization a concentration series of 0.5-250 nM of the corresponding oligonucleotides (Activator, PH2, H1 or H2) were injected over the surface with a flow rate of 45 uL min$^{-1}$. For ternary complex studies (PH2-PH1-I and H2-H1-Fishing rod), we captured the ligand prior to the sample injection. All associations were monitored for 3 min, while dissociations were evaluated for 1 min. At the end of each cycle the surface was regenerated with a 30-sec pulse injection of 10 mM NaOH. Surface decay was less than 1% per cycle. The sensorgrams for all experiments were double referenced using Biaevaluation v. 3.0 software (GE Healthcare, UK).

Imaging of Fluorescence Build-Up on Magnetic Beads Using the Opera High Content Screening System Streptavidin coated magnetic beads (Dynabeads M-280 Streptavidin, Invitrogen) were loaded with 2 nM biotinylated fishing rod and incubated them for 30 min at RT. In the meantime H1 and H2 were thawed and separately left to adjust to room temperature for 30 min. The beads were washed twice and incubated with increasing concentrations of H1 and H2 at 37° C. Beads were transferred to a 384 well plate (Molecular Machines and Industries AG, MMI, Switzerland) and imaged in the Opera High Content Screening System (Perkin Elmer). 16 images of each condition were taken using a 488 nm laser at 2 mW to excite the samples through a 60×UPLSAPO water immersion objective with NA1.2. The exposure time of the images was 160 ms and exposure height was set to 1.5 µm above the bottom of the well. Images were captured using a cooled CCD camera with a 520 (+/−35) band pass filter.

Validation of Opera HCSS by Epifluorescence Microscopy

Streptavidin coated magnetic beads were loaded with 10 nM biotinylated PH1 and PH2. After washing away the residual unbound hairpins, the reaction was split one half was incubated with 10 nM Activator oligonucleotide for 30 min at 37° C. while the other half was left in the reaction buffer. After two additional washing steps both samples were incubated with 50 nM of amplification oligonucleotides. After predefined periods of time (10 min, 30 min, 60 min and 150 min) samples were taken, washed, immobilized on a poly L-lysine coated glass slide (Sigma) and visualized under the microscope (Axioplan, Zeiss).

In Situ Experiments in Fixed Cells

Prox-HCR Experiments

BjhTert slides were rehydrated in PBS, permeabilized them with 0.1% TritonX-100 for 5 min and washed in PBS again. The cells were blocked using DuoLink blocking reagent (Olink Bioscience) for 45 min at 37° C. Thereafter the cells were incubated with primary antibodies against PDGFR (1:100, #3169S, Cell Signaling) and total phosphotyrosine (1:100, pY-100, #9411S, Cell Signaling) overnight at 4° C. Upon washing twice with PBS at RT for 2 min and once with HCR buffer for 2 min, the slides were incubated with 10 µg mL$^{-1}$ proximity-probes directed against rabbit IgG and mouse IgG for 1 h at 37° C. in HCR buffer. After two more washing steps with HCR buffer the slides were incubated with 10 nM of activator oligonucleotide for 30 min. After a quick wash, the cells were incubated with 20 nM HCR hairpins for 1 h at 37° C. in HCR buffer. Subsequently, the slides were washed twice before the nuclei were stained with Hoechst (in PBS) and the slides were mounted with SlowFade and a coverslip.

Regarding the DLD1 and HG3 cells, cells were rehydrated and permeabilised as described above. Nonspecific binding sites were blocked with DuoLink blocking reagent for 1 h at 37° C., after which cells were incubated with antibodies directed against E-cadherin (1:100, 610182, BD Biosciences) and ß-catenin (1:300, Sc7199, Santa-Cruz) for DLD1 cells and primary antibodies directed against total Syk (1:100, Sc1240, Santa-Cruz) and p-Syk (1:200, AP3271a, Abgent) for HG3 cells overnight at 4° C. Upon washing 5 min with TBS 0.05% TWEEN®-20 (polysorbate 20), nonspecific binding sites were blocked again for 15 min and the slides were incubated with 10 µg mL$^{-1}$ proximity-probes directed against rabbit and mouse IgG for 1 h at 37°

C. Lastly, the initiation and amplification of prox-HCR was performed as described above.

In Situ PLA Experiments

For in situ PLA experiments the DuoLink kit (Olink Bioscience) was used according to manufacturer recommendations. Briefly DLD1 cells were rehydrated and permeabilized as described for prox-HCR. Upon blocking of nonspecific binding sites with DuoLink blocking reagent for 1 h at 37° C. cells were incubated with primary antibodies directed against E-cadherin (1:100) and ß-catenin (1:300) overnight at 4° C. Cells were washed with DuoLink Wash buffer A two time for 5 min and incubated with proximity probes (PLUS and MINUS, Olink Bioscience) in antibody diluent (Olink Bioscience) for 1 h at 37° C. After a new round of washing steps ligation mix was applied to the cells and incubated for 30 min at 37° C. Additional washing was followed by RCA and fluorescent detection of the rolling circle products. Cells were counterstained with Hoechst and mounted as described above.

Tissue Experiments

Fresh frozen healthy colon tissue was fixed using 3.7% formaldehyde solution at RT for 15 min. Slides were washed with PBS twice and then blocked using Duolink blocking reagent for 60 min at 37° C. Subsequent to blocking the slides were incubated with primary antibodies against E-cadherin (1:100) and β-catenin (1:300) in PBS over night at 4° C. The next day the slides were washed with PBS 3×2 min and blocked again for 30 min. The slides were incubated with proximity-probes directed against mouse and rabbit IgG for 1 h at 37° C. in HCR buffer. After two more washes with HCR buffer the slides were incubated with activator oligonucleotides for 30 min at 37° C. Slides were washed again twice with HCR buffer and slides were incubated with 20 nM HCR hairpins in HCR buffer for 1 h at 37° C. Slides were subsequently washed with HCR buffer and once with PBS before nuclei were counterstained with Hoechst. Slides were mounted with SlowFade.

For epifluorescence image acquisition of assays run on cells and tissue a Zeiss Axioplan 2 imaging microscope equipped with filters optimized for Texas Red, AlexaFluor 488, Cy5 and DAPI, a 40× (1.3 NA) objective and a Zeiss AxioCam MRm camera were used. Exposure times were kept the same for all samples within each experiment. For the in situ experiments we acquired 10 z-levels with 330 nm in between. For all datasets we chose the sites for acquisition randomly.

Flow Cytometry

Cells were blocked using Olink block for 45 min before they were incubated with primary antibodies directed against EGFR (1:500, M723901, Dako) and Alexa Fluor 488 (1:500, A-11094, life technologies) at 4° C. over night. After washing the prox-HCR protocol was carried out as described above and fluorescence was read out using the LSR-II (BD Bioscience).

Image Analysis

In order to achieve a measurement of the fluorescence of the magnetic beads in the images, which translates to signal production via HCR, we used CellProfiler 2.1.0. Fluorescent beads were identified as primary objects. Then we measured the median intensity value for all pixels of the identified objects, which are translated into fluorescence units (FU) (i.e. a normalization of the intensity values recorded at 8 bit to a scale from 0 to 1).

The invention claimed is:

1. A method for detecting an analyte in a sample, said method comprising:
   a. contacting said sample with a set of proximity probes comprising first and second proximity probes, which probes each comprise an analyte-binding domain capable of binding directly or indirectly to said analyte and a nucleic acid domain, such that the proximity probes can simultaneously bind, directly or indirectly, to the analyte, wherein
   i. the nucleic acid domain of the first probe comprises a first region of complementarity to a cognate second region of complementarity in the nucleic acid domain of the second probe, wherein said first region of complementarity is protected (i)(a) by a blocking nucleotide sequence, or (i)(b) within a secondary structure, to prevent the first and second complementary regions from hybridising to one another, and the first and second regions of complementarity are capable of hybridising to each other when the blocking nucleotide sequence is removed or the secondary structure is disrupted; and
  ii. the nucleic acid domain of the second probe comprises a hybridization chain reaction (HCR) initiator region comprised within a metastable secondary structure, wherein the HCR initiator region is unable to initiate an HCR reaction when comprised within the metastable secondary structure and wherein the metastable secondary structure is capable of being unfolded to release a single stranded HCR initiator region from the HCR initiator region when said metastable secondary structure is unfolded, and wherein the single stranded HCR initiator region is capable of initiating an HCR reaction;
 b. removing the blocking nucleotide sequence or disrupting the secondary structure to deprotect the first complementary region and allow the first and second complementary regions of the nucleic acid domains of said first and second probes to hybridize to each other when said probes have both bound directly or indirectly to the analyte, wherein said hybridization results in unfolding of the metastable secondary structure of the nucleic acid domain of the second probe and release of the single-stranded HCR initiator region;
 c. performing an HCR reaction using at least two HCR monomers, wherein the first HCR monomer comprises a region of complementarity to the single stranded HCR initiator region and hybridisation of the single stranded HCR initiator region to the first HCR polymer begins the HCR reaction to form a polymer; and
 d. detecting the polymer thereby to detect the analyte.

2. The method of claim 1, wherein one or more mismatches are present when the first region of complementarity of the nucleic acid domain of the first proximity probe is hybridised to the second region of complementarity of the nucleic acid domain of the second proximity probe.

3. The method of claim 1, wherein in step (a) the first region of complementarity of the first probe is protected by the blocking nucleotide sequence, wherein prior to step (a), said blocking nucleotide sequence is pre-hybridised to the nucleic acid domain of the first probe before the first probe is contacted with the sample, and in step (b), said blocking nucleotide sequence is removed to deprotect the first complementary region.

4. The method of claim 3, wherein the blocking nucleotide sequence is removed by degrading the blocking nucleotide sequence.

5. The method of claim 1, wherein the first region of complementarity of the first probe is protected by the secondary structure, which secondary structure is disruptable by unfolding to deprotect the first complementary region.

6. The method of claim 5, wherein the secondary structure protecting the first region of complementarity is a metastable secondary structure.

7. The method of claim 6, wherein the metastable secondary structure protecting the first region of complementarity comprises a hairpin structure.

8. The method of claim 5, wherein the secondary structure protecting the first region of complementarity comprises a hairpin structure and is cross-linked via a reversible covalent bond, and following binding of the proximity probes, said covalent bond is broken, unfolding the hairpin structure and exposing the first region of complementarity.

9. The method of claim 8, wherein the reversible covalent bond is a disulphide bond, and wherein the disulphide bond is reduced to break the reversible covalent bond.

10. The method of claim 1, wherein the metastable secondary structure of the nucleic domains of the second proximity probe comprises a hairpin structure.

11. The method of claim 1, wherein the first region of complementarity of the nucleic acid domain of the first proximity probe is protected within the secondary structure, which secondary structure is disruptable by unfolding to deprotect the first region of complementarity of the nucleic acid domain of the first proximity probe, and wherein following direct or indirect binding of the proximity probes to the analyte, an activator nucleotide sequence is introduced, said activator nucleotide sequence comprising a region of complementarity to a cognate region of complementarity which is accessible in the nucleic acid domain of the first proximity probe, and wherein the activator nucleotide sequence hybridises to the nucleic acid domain of the first proximity probe, unfolding the secondary structure and exposing said first region of complementarity of the nucleic acid domain of the first proximity probe.

12. The method of claim 11, wherein the cognate region of complementarity to the activator nucleotide sequence lies in the loop of a hairpin structure in the first nucleic acid domain.

13. The method of claim 1, wherein the first region of complementarity is protected within the secondary structure when the analyte-binding domain of the first probe is unbound, and binding of the first proximity probe induces a conformational change in the nucleic acid domain of the first proximity probe to disrupt the secondary structure, exposing the first region of complementarity.

14. The method of claim 1, wherein the analyte-binding domain of at least one of the proximity probes
  (i) is or comprises a protein; or
  (ii) is an antibody; or
  (iii) is or comprises a nucleic acid molecule.

15. The method of claim 14, wherein the nucleic acid molecule (iii) comprises a complementary sequence capable of hybridising to a nucleic acid analyte or is an aptamer.

16. The method of claim 1, wherein the analyte is or comprises a protein and/or a nucleic acid, or wherein the analyte is or comprises a protein-protein complex or a protein-nucleic acid complex.

17. The method of claim 1, wherein two or more different target analytes are detected.

18. The method of claim 1, wherein the HCR monomers comprise hairpin structures.

19. The method of claim 1, wherein 3 or more HCR monomers are used and greater than linear amplification is achieved in the HCR reaction.

20. The method of claim 1, wherein the polymer product is detected using a detection probe which hybridises to the polymer, and/or wherein at least one HCR monomer is provided with a detectable label.

21. The method of claim 20, wherein said label is fluorescent, or colorimetrically detectable, or comprises at least one member of a Förster resonance energy transfer (FRET) pair.

22. The method of claim 1, wherein one or both strands of the HCR polymer are ligated, or wherein said method comprises a further signal generation step based on the HCR polymer.

23. The method of claim 22, wherein said further signal generation step comprises a RCA reaction.

24. A kit, said kit comprising:
 a. at least one set of proximity probes comprising first and second proximity probes, which probes each comprise an analyte-binding domain capable of simultaneously binding directly or indirectly to said analyte and a nucleic acid domain, wherein i. the nucleic acid domain of the first probe comprises a first region of complementarity to a cognate second region of complementarity in the nucleic acid domain of the second probe, wherein said first region of complementarity is protected (i)(a) by a blocking nucleotide sequence, or (i)(b) within a secondary structure, to prevent the first and second complementary regions from hybridising to one another, and the first and second regions of complementarity are capable of hybridising to each other when the blocking nucleotide sequence is removed or the secondary structure is disrupted, and ii. the nucleic acid domain of the second probe comprises a hybridization chain reaction (HCR) initiator region comprised within a metastable secondary structure, wherein the HCR initiator region is unable to initiate an HCR reaction when comprised within the metastable secondary structure and wherein the metastable secondary structure is capable of being unfolded to release a single stranded HCR initiator region from the HCR initiator region when said metastable secondary structure is unfolded, wherein hybridisation of the first and second regions of complementarity results in unfolding of the metastable secondary structure, and wherein the single stranded HCR initiator region is capable of initiating an HCR reaction; and b. at least two HCR monomers capable of performing an HCR reaction, wherein the first HCR monomer comprises a region of complementarity to the single stranded HCR initiator region.

25. The kit of claim 24, wherein the kit further comprises means for removing the blocking nucleotide sequence or disrupting the secondary structure to allow the first and second complementary regions of the nucleic acid domains of said first and second probes to hybridise to each other when said probes have both bound directly or indirectly to the analyte, wherein said hybridisation results in unfolding of the metastable secondary structure of the nucleic acid domain of the second probe to release the single-stranded HCR initiator region.

26. The kit of claim 25, wherein said kit further comprises means for detecting the polymer.

27. The kit of claim 25 wherein the means for disrupting the secondary structure to allow the first and second complementary regions of the nucleic acid domains of said first and second probes to hybridise to each other is an activator nucleotide sequence.

* * * * *

UNITED STATES PATENT AND TRADEMARK OFFICE
CERTIFICATE OF CORRECTION

PATENT NO. : 11,034,995 B2
APPLICATION NO. : 15/116267
DATED : June 15, 2021
INVENTOR(S) : Ola Söderberg et al.

Page 1 of 1

It is certified that error appears in the above-identified patent and that said Letters Patent is hereby corrected as shown below:

On the Title Page

Item [30], delete "1401885" and insert --1401885.7--.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 13

<210> SEQ ID NO 1
<211> LENGTH: 44
<212> TYPE: DNA
<213> ORGANISM: Artificial Sequence
<220> FEATURE:
<223> OTHER INFORMATION: Activator_oligo

<400> SEQUENCE: 1
gactcgcatt cactgaatac agcgggcctt catgttacag acga                 44

<210> SEQ ID NO 2
<211> LENGTH: 78
<212> TYPE: DNA
<213> ORGANISM: Artificial Sequence
<220> FEATURE:
<223> OTHER INFORMATION: Proximity hairpin 1

<400> SEQUENCE: 2
tcgtctgtaa catgaaggcc cgctgtattc agtgaatgcg agtcagacga atacagcggg     60
ccttcatgtt acagacga                                                   78

<210> SEQ ID NO 3
<211> LENGTH: 67
<212> TYPE: DNA
<213> ORGANISM: Artificial Sequence
<220> FEATURE:
<223> OTHER INFORMATION: Proximity hairpin 2

<400> SEQUENCE: 3

```
ctgggagtcg tctgtaacat gaaggcccgc tgtattcgtc ttacttcatg ttacagacga    60
ctcccag                                                              67

<210> SEQ ID NO 4
<211> LENGTH: 50
<212> TYPE: DNA
<213> ORGANISM: Artificial Sequence
<220> FEATURE:
<223> OTHER INFORMATION: HCR monomer 1
<220> FEATURE:
<221> NAME/KEY: modified_base
<222> LOCATION: (1)..(1)
<223> OTHER INFORMATION: Labelled with fluorophore

<400> SEQUENCE: 4
acagacgact cccagtacct tcagctggga gtcgtctgta acatgaagta               50

<210> SEQ ID NO 5
<211> LENGTH: 50
<212> TYPE: DNA
<213> ORGANISM: Artificial Sequence
<220> FEATURE:
<223> OTHER INFORMATION: HCR monomer 2
<220> FEATURE:
<221> NAME/KEY: misc_feature
<222> LOCATION: (50)..(50)
<223> OTHER INFORMATION: Labelled with fluorophore

<400> SEQUENCE: 5
ctgaaggtac tgggagtcgt ctgttacttc atgttacaga cgactcccag               50

<210> SEQ ID NO 6
<211> LENGTH: 83
<212> TYPE: DNA
<213> ORGANISM: Artificial Sequence
<220> FEATURE:
<223> OTHER INFORMATION: Proximity hairpin 1 oligo-A

<400> SEQUENCE: 6
aaaaatcgtc tgtaacatga aggcccgctg tattcagtga atgcgagtca gacgaataca    60
gcgggccttc atgttacaga cga                                            83

<210> SEQ ID NO 7
<211> LENGTH: 72
<212> TYPE: DNA
<213> ORGANISM: Artificial Sequence
<220> FEATURE:
<223> OTHER INFORMATION: Proximity hairpin 2 oligo-A

<400> SEQUENCE: 7
aaaaagtggg agtcgtctgt aacatgaagg cccgctgtat tcgtcttact tcatgttaca    60
gacgactccc ac                                                        72

<210> SEQ ID NO 8
<211> LENGTH: 50
<212> TYPE: DNA
<213> ORGANISM: Artificial Sequence
<220> FEATURE:
<223> OTHER INFORMATION: HCR_monomer 1
<220> FEATURE:
<221> NAME/KEY: misc_feature
<222> LOCATION: (1)..(1)
<223> OTHER INFORMATION: Labelled with fluorophore

<400> SEQUENCE: 8
acagacgact cccacattct ccaggtggga gtcgtctgta acatgaagta               50
```

```
<210> SEQ ID NO 9
<211> LENGTH: 50
<212> TYPE: DNA
<213> ORGANISM: Artificial Sequence
<220> FEATURE:
<223> OTHER INFORMATION: HCR_monomer 2
<220> FEATURE:
<221> NAME/KEY: misc_feature
<222> LOCATION: (50)..(50)
<223> OTHER INFORMATION: Labelled with fluorophore

<400> SEQUENCE: 9
ctggagaatg tgggagtcgt ctgttacttc atgttacaga cgactcccac        50

<210> SEQ ID NO 10
<211> LENGTH: 38
<212> TYPE: DNA
<213> ORGANISM: Artificial Sequence
<220> FEATURE:
<223> OTHER INFORMATION: Activator oligo short

<400> SEQUENCE: 10
gactcgcatt cactgaatac agcgggcctt catgttac                     38

<210> SEQ ID NO 11
<211> LENGTH: 44
<212> TYPE: DNA
<213> ORGANISM: Artificial Sequence
<220> FEATURE:
<223> OTHER INFORMATION: Activator oligo mismatch

<400> SEQUENCE: 11
gactcgcatt cactgaatac agcgggcctt catgccacag acga              44

<210> SEQ ID NO 12
<211> LENGTH: 83
<212> TYPE: DNA
<213> ORGANISM: Artificial Sequence
<220> FEATURE:
<223> OTHER INFORMATION: Proximity hairpin 1 mismatch

<400> SEQUENCE: 12
aaaaatcgtc tgtggcatga aggcccgctg tattcagtga atgcgagtca gacgaataca    60
gcgggccttc atgccacaga cga                                           83

<210> SEQ ID NO 13
<211> LENGTH: 38
<212> TYPE: DNA
<213> ORGANISM: Artificial Sequence
<220> FEATURE:
<223> OTHER INFORMATION: Activator oligo short mismatch

<400> SEQUENCE: 13
gactcgcatt cactgaatac agcgggcctt catgccac                     38
```